(12) United States Patent
Paradis et al.

(10) Patent No.: US 10,626,163 B2
(45) Date of Patent: Apr. 21, 2020

(54) METHODS OF MODULATING GABAERGIC INHIBITORY SYNAPSE FORMATION AND FUNCTION

(71) Applicants: Suzanne Paradis, Lexington, MA (US); Anna R. Moore, Newton, MA (US); Marissa S. Kuzirian, Waltham, MA (US)

(72) Inventors: Suzanne Paradis, Lexington, MA (US); Anna R. Moore, Newton, MA (US); Marissa S. Kuzirian, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 14/761,983

(22) PCT Filed: Jan. 24, 2014

(86) PCT No.: PCT/US2014/012997
§ 371 (c)(1),
(2) Date: Jul. 20, 2015

(87) PCT Pub. No.: WO2014/116982
PCT Pub. Date: Jul. 31, 2014

(65) Prior Publication Data
US 2015/0361156 A1  Dec. 17, 2015

Related U.S. Application Data

(60) Provisional application No. 61/756,809, filed on Jan. 25, 2013.

(51) Int. Cl.
C07K 14/705 (2006.01)
A61K 38/17 (2006.01)
A61K 48/00 (2006.01)
C12N 15/113 (2010.01)

(52) U.S. Cl.
CPC ........ *C07K 14/70596* (2013.01); *A61K 38/17* (2013.01); *A61K 38/177* (2013.01); *A61K 48/00* (2013.01); *C12N 15/1138* (2013.01); *C07K 2319/30* (2013.01); *C12N 2310/14* (2013.01); *C12N 2320/30* (2013.01)

(58) Field of Classification Search
CPC ...... A61K 38/177; A61K 48/00; A61K 38/17; C07K 2319/30; C07K 14/70596; C12N 15/1138; C12N 2310/14; C12N 2320/30
See application file for complete search history.

(56) References Cited

U.S. PATENT DOCUMENTS 9,249,227 B2 * 2/2016 Smith ............. A61K 39/3955
9,598,495 B2 * 3/2017 Smith ............. A61K 39/3955
2011/0269764 A1 11/2011 Cohen et al.
2012/0270268 A1 10/2012 Smith et al.

OTHER PUBLICATIONS

McDermott et al. Class 4 Semaphorins and Plexin-B receptors regulate GABAergic and glutamatergic synapse development in the mammalian hippocampus. Mol Cell Neurosci. Oct. 2018;92:50-66. doi: 10.1016/j.mcn.2018.06.008. Epub Jul. 4, 2018.*
Vickers. A vaccine against Alzheimer's disease: developments to date. Drugs Aging 2002; 19(7):487-94.*
Perrin et al. Multimodal techniques for diagnosis and prognosis of Alzheimer's disease. Nature Oct. 15, 2009;461(7266):916-22, Published online Oct. 14, 2009.*
Hampel et al. The future of Alzheimer's disease: the next 10 years. Prog Neurobiol. Dec. 2011;95(4):718-28. Epub Nov. 22, 2011.*
Hsiung et al. Pharmacological treatment in moderate-to-severe Alzheimer's disease. Expert Opin Pharmacother. Oct. 2008;9(15): 2575-82. doi: 10.1517/14656566.9.15.2575.*
Kuzirian et al. Emerging themes in GABAergic synapse development. Prog Neurobiol. Sep. 15, 2011;95(1):68-87. doi: 10.1016/j. pneurobio.2011.07.002. Epub Jul. 20, 2011.*
Lin et al., "Sema4D-plexin-B1 Implicated in Regulation of Dendritic Spine Density Through RhoA/ROCK Pathway," Neuroscience Letters 428:1-6 (2007).
Paradis et al, "An RNAi-Based Approach Identifies Molecules Required for Glutamatergic and GABAergic Synapse Development," Neuron 53:217-232 (2007).
International Search Report and Written Opinion for corresponding application No. PCT/US14/12997 dated Jul. 29, 2014.
Acker et al., "Semaphorin 4D Promotes Inhibitory Synapse Formation and Suppresses Seizures in vivo," Epilepsia 59 (6):1257-1268 (2018).
Fischer et al., "Rapid Actin-Based Plasticity in Dendritic Spines," Neuron 20:847-854 (1998).
Yuste, "Dendritic Spines and Distributed Circuits," Neuron 71:772-781 (2011).

* cited by examiner

*Primary Examiner* — Gregory S Emch
(74) *Attorney, Agent, or Firm* — Pepper Hamilton LLP

(57) ABSTRACT

The present technology relates to methods of modulating the number of GABAergic synapses between at least two neurons. These methods include contacting at least one of the neurons with a PlexinB agonist or a nucleic acid molecule encoding a PlexinB agonist, such as a composition including a Sema4D polypeptide or an extracellular fragment thereof, or a nucleic acid molecule encoding the Sema4D polypeptide or extracellular fragment thereof. The present technology also relates to methods of modulating neuronal activity in the central nervous system or peripheral nervous system of a subject in need thereof by modulating the number of GABAergic synapses between at least two neurons. The present technology further relates to methods of treating a neurological disorder that would benefit from modulating neuronal activity in the central nervous system or peripheral nervous system of a subject in need thereof.

12 Claims, 8 Drawing Sheets

Specification includes a Sequence Listing.

METHODS OF MODULATING GABAERGIC INHIBITORY SYNAPSE FORMATION AND FUNCTION

This application is a national stage application under 35 U.S.C. § 371 of PCT Application No. PCT/US2014/012997, filed Jan. 24, 2014, which claims benefit of U.S. Provisional Patent Application Ser. No. 61/756,809, filed Jan. 25, 2013, which is hereby incorporated by reference in its entirety.

This technology relates to methods of modulating the number of GABAergic synapses between at least two neurons. Certain of these methods include contacting at least one of the neurons with a PlexinB receptor agonist or a nucleic acid molecule encoding a PlexinB agonist or a PlexinB polypeptide. Others of these methods include administering an agent that inhibits the level of expression or activity of a PlexinB agonist or an active peptide fragment or derivative thereof or an agent that inhibits the level of expression or activity of a PlexinB polypeptide.

This invention was made with government support under NS065856 awarded by the National Institutes of Health. The government has certain rights in the invention.

BACKGROUND OF THE INVENTION

Biochemical and candidate gene approaches over the past four decades have led to the identification of molecules that function to regulate excitatory, glutamatergic synapse formation and synaptic transmission. In contrast, far less is known about inhibitory, GABAergic synapse formation and function. It has previously been determined that knockdown of the transmembrane class 4 Semaphorin Sema4D in the postsynaptic neuron leads to a decrease in the density of GABAergic synapses formed onto that neuron, without an effect on glutamatergic synapse density (Paradis et al., "An RNAi-Based Approach Identifies Molecules Required for Glutamatergic and GABAergic Synapse Development," *Neuron.*, 53:217-232 (2007)). Further, immunohistochemical analysis of hippocampi isolated from mice in which the Sema4D gene was constitutively deleted (Shi et al., "The Class IV Semaphorin CD100 Plays Nonredundant Roles in the Immune System: Defective B and T Cell Activation in CD100-Deficient Mice," *Immunity*, 13:633-642 (2000)) revealed a decrease in intensity of GABA-synthesizing enzyme GAD67 immunoreactivity in the neuropil (Paradis et al., "An RNAi-Based Approach Identifies Molecules Required for Glutamatergic and GABAergic Synapse Development," *Neuron.*, 53:217-232 (2007)). This result is consistent with a deficit in GABAergic synapse development in the absence of Sema4D in vivo (Paradis et al., "An RNAi-Based Approach Identifies Molecules Required for Glutamatergic and GABAergic Synapse Development," *Neuron.*, 53:217-232 (2007)). Thus, these experiments identify Sema4D as one of only a few molecules described thus far that preferentially regulate GABAergic synapse formation.

The mammalian Semaphorin family of proteins consists of 20 secreted and membrane-bound molecules grouped into five different classes based on their sequence homology and protein domain structures (Tran et al., "Semaphorin Regulation of Cellular Morphology," *Ann. Rev. Cell Dev. Biol.*, 23:263-292 (2007); Yazdani et al., "The Semaphorins," *Genome Biol.*, 7:211 (2006); Zhou et al., "Semaphorin Signaling: Progress Made and Promises Ahead," *Trends Biochem. Sci.*, 33:161-170 (2008)). Sema4D signaling is required for the proper development and function of a variety of organ systems including the immune system, cardiovascular system, and CNS (Ch'ng et al., "Roles of Sema4D and Plexin-B1 in Tumor Progression," *Mol. Cancer*, 9:251 (2010); Kruger et al., "Semaphorins Command Cells to Move," *Nat. Rev. Mol. Cell Biol.*, 6:789-800 (2005); Pasterkamp et al., "Semaphorin Function in Neural Plasticity and Disease," *Curr. Opin. Neurobiol.*, 19:263-274 (2009); Takamatsu et al., "Diverse Roles for Semaphorin-Plexin Signaling in the Immune System," *Trend Immunol.*, 33:127-135 (2012); Yazdani et al., "The Semaphorins," *Genome Biol.*, 7:211 (2006)). The hallmark of a Semaphorin family member is the extracellular Semaphorin (Sema) domain: a conserved, cysteine-rich region of about 500 amino acids at the N-terminus of the protein (Yazdani et al., "The Semaphorins," *Genome Biol.*, 7:211 (2006)). Sema4D is a transmembrane protein with a short intracellular domain in addition to its extracellular Sema domain. Currently, identifiable protein motifs in the intracellular domain of Sema4D have not been described and a function for this region has yet to be determined (Ch'ng et al., "Roles of Sema4D and Plexin-B1 in Tumor Progression," *Mol. Cancer*, 9:251 (2010); Pasterkamp et al., "Semaphorin Function in Neural Plasticity and Disease," *Curr. Opin. Neurobiol.*, 19:263-274 (2009); Takamatsu et al., "Diverse Roles for Semaphorin-Plexin Signaling in the Immune System," *Trend Immunol.*, 33:127-135 (2012)). Therefore, all of the biological functions ascribed thus far to Sema4D can be attributed to the extracellular region, containing the conserved Sema domain through which Sema4D binds to its putative receptors: PlexinB family members and CD72 (Takamatsu et al., "Diverse Roles for Semaphorin-Plexin Signaling in the Immune System," *Trend Immunol.*, 33:127-135 (2012); Tamagnone et al., "Plexins are a Large Family of Receptors for Transmembrane, Secreted, and GPI-Anchored Semaphorins in Vertebrates," *Cell*, 99:71-80 (1999); Yazdani et al., "The Semaphorins," *Genome Biol.*, 7:211 (2006)).

Recently, time-lapse imaging studies over the course of several hours have provided some insight into the cell biology of GABAergic synapse development (Dobie et al., "Inhibitory Synapse Dynamics: Coordinated Presynaptic and Postsynaptic Mobility and the Major Contribution of Recycled Vesicles to New Synapse Formation," *J. Neurosci.*, 31:10481-10493 (2011); Wierenga et al., "GABAergic Synapses are Formed Without the Involvement of Dendritic Protrusions," *Nat. Neurosci.*, 11:1044-1052 (2008)). For example, live-imaging of GABAergic synapse formation in hippocampal slices revealed that, in contrast to glutamatergic synapse development, GABAergic synapses form at pre-existing axodendritic crossings without the involvement of axonal or dendritic protrusions (Wierenga et al., "GABAergic Synapses are Formed Without the Involvement of Dendritic Protrusions," *Nat. Neurosci.*, 11:1044-1052 (2008)). In addition, time-lapse imaging in maturing neuronal cultures of labeled components of GABAergic synapses, such as $GABA_A$ receptors and Gephyrin, has revealed that synaptic components are transported in mobile packets to synaptic sites along dendrites (Dobie et al., "Inhibitory Synapse Dynamics: Coordinated Presynaptic and Postsynaptic Mobility and the Major Contribution of Recycled Vesicles to New Synapse Formation," *J. Neurosci.*, 31:10481-10493 (2011); Maas et al., "Neuronal Cotransport of Glycine Receptor and the Scaffold Protein Gephyrin," *J. Cell Biol.*, 172:441-451 (2006); Twelvetrees et al., "Delivery of GABAARs to Synapses is Mediated by HAP1-KIF5 and Disrupted by Mutant Huntingtin," *Neuron*, 65:53-65 (2010)). However, these previous studies have not addressed either the mechanism or time frame of assembly of GABAergic synapses in response to a specific synaptogenic signal.

While the underlying cause of epileptogenesis remains largely unknown, the major phenotype of epileptic seizures is an increase in neuronal activity either in a specific focal region or globally (Morimoto et al., "Kindling and Status Epilepticus Models of Epilepsy: Rewiring the Brain," *Prog. Neurobiol.*, 73:1-60 (2004)). Studies of temporal lobe epilepsy reveal an increase in reorganization of neuronal connections including increased excitatory axon sprouting and synaptogenesis (Morimoto et al., "Kindling and Status Epilepticus Models of Epilepsy: Rewiring the Brain," *Prog. Neurobiol.*, 73:1-60 (2004)). Additionally, animal studies suggest that seizure activity can be facilitated by a loss of inhibitory control on neighboring neurons (Cossart et al., "Dendritic but not Somatic GABAergic Inhibition is Decreased in Experimental Epilepsy," *Nat. Neurosci.*, 4:52-62 (2001); Depaulis et al., "Quiescence and Hyporeactivity Evoked by Activation of Cell Bodies in the Ventrolateral Midbrain Periaqueductal Gray of the Rat," *Exp. Brain Res.*, 99:75-83 (1994); Kobayashi et al., "Reduced Inhibition of Dentate Granule Cells in a Model of Temporal Lobe Epilepsy," *J. Neurosci.*, 23:2440-2452 (2003)), illustrating the importance of precise regulation of inhibition and excitation within neural networks. However, the molecular mechanisms and time course of the development of inhibition in neuronal circuits are not well understood and biological targets affecting such inhibitory synapses, as well as agents for modulating such targets, are not known. Thus, there is a great need in the art to elucidate such molecular mechanisms, biological targets, and agents for treating, diagnosing, prognosing, and preventing neurological disorders that could benefit from increasing inhibitory synapse formation and activity.

The present invention is directed to overcoming these and other deficiencies in the art.

SUMMARY OF THE INVENTION

This technology relates to a method of modulating the number of GABAergic synapses between at least two neurons. The method includes contacting at least one of the neurons with a PlexinB agonist or a nucleic acid molecule encoding a PlexinB agonist to promote GABAergic synapse formation.

This technology also relates to a method of modulating the number of GABAergic synapses between at least two neurons which includes contacting at least one of the neurons with a Sema4D polypeptide or an extracellular fragment thereof, or a nucleic acid molecule encoding the Sema4D polypeptide or extracellular fragment thereof to promote GABAergic synapse formation.

This technology also relates to a method of modulating neuronal activity in the central nervous system or peripheral nervous system of a subject in need thereof by modulating the number of GABAergic synapses between at least two neurons. The method includes administering to the subject a therapeutic agent that is a PlexinB agonist or a nucleic acid molecule encoding a PlexinB agonist. Administration of the therapeutic agent is effective to modulate the neuronal activity of the subject in need thereof.

This technology further relates to a method of modulating neuronal activity in the central nervous system or peripheral nervous system of a subject in need thereof by modulating the number of GABAergic synapses between at least two neurons including administering to the subject a composition including a Sema4D polypeptide or an extracellular fragment thereof, or a nucleic acid molecule encoding said Sema4D polypeptide or extracellular fragment thereof, to thereby modulate the neuronal activity of the subject in need thereof.

This technology also relates to a method of treating a neurological disorder of a subject in need thereof. The method includes administering to the subject a therapeutic agent that is a PlexinB agonist or a nucleic acid molecule encoding a PlexinB agonist. Administration of the therapeutic agent is effective to treat the neurological disorder.

This technology further relates to a method of treating a neurological disorder of a subject in need thereof. The method includes administering to the subject a composition including a Sema4D polypeptide or an extracellular fragment thereof, or a nucleic acid molecule encoding said Sema4D polypeptide or extracellular fragment thereof, thereby treating the neurological disorder of the subject in need thereof.

This technology also relates to a method of treating a neurological disorder of a subject in need thereof. The method includes administering to the subject an agent that inhibits the level of expression or activity of a PlexinB agonist or an active peptide fragment or derivative thereof. Administration of the agent is effective to treat the neurological disorder.

This technology further relates to a method of treating a neurological disorder of a subject in need thereof. The method includes administering to the subject an agent that inhibits the level of expression or activity of a Sema4D polypeptide or extracellular fragment thereof, thereby treating the neurological disorder of the subject in need thereof.

This technology also relates to a method of treating a neurological disorder of a subject in need thereof. The method includes administering to the subject an agent that inhibits the level of expression or activity of a PlexinB polypeptide or an active peptide fragment or derivative thereof. Administration of the agent is effective to treat the neurological disorder.

In accordance with the present technology, methods have been developed for treating, diagnosing, prognosing, and preventing neurological disorders based on the discovery described herein that molecules that bind to and activate a PlexinB receptor, such as Sema4D, and/or PlexinB polypeptide can modulate the number of GABAergic synapses between neurons and thereby regulate neuronal activity. Although prior research has been conducted to investigate whether a deficit in GABAergic synapse development occurs in the absence of Sema4D, whether administration of a molecule that binds to and activates a PlexinB receptor, such as Sema4D, would increase GABAergic synapses between neurons and thereby regulate neuronal activity is previously unknown and has unexpectedly been discovered as described herein. The methods of the present technology are widely applicable to neurological disorders. In particular, this approach has the benefit of addressing and potentially reversing the development and progression of epilepsy in, for example, infants and children with seizure disorders, as opposed to symptomatic treatment with pharmacological agents such as benzodiazepines.

BRIEF DESCRIPTION OF THE DRAWINGS

FIGS. 2A-B show representative images of growth cones from cultured hippocampal neurons treated with Fc control (10 nM, FIG. 2A) or Sema4D-Fc treated (10 nM, FIG. 2B). FIG. 2C shows a quantification of the percent collapsed growth cones (n>84 growth cones per treatment; *p<0.05 student's t-test). All data are plotted as mean±S.E.M. Scale bar=5 μm.

FIGS. 3A-B show stretches of dendrites and the quantification of synapse density on dendrites from cultured hippocampal neurons isolated from PlxnB1−/− or wildtype littermates (11 days in vitro (DIV)), treated with AP control (AP alone) or Sema4D-AP (1 nM, 4 hours). Neurons were immunostained for GAD65, GABA$_A$Rγ2, and MAP2 (n>34, 2 experiments normalized to AP alone; *p<0.05, two-way ANOVA). FIGS. 3A and 3C show inhibitory synapses (GAD65/GABA$_A$Rγ2) on the somas of neurons treated AP control or Sema4D-AP, as analyzed by tracing somas (white dashed lines). Synapse density was quantified within such regions of interest (n>20, 2 experiments; *p<0.05, two-way ANOVA). All data shown in FIGS. 3A-3C are plotted as mean±S.E.M.

FIG. 4A shows representative mIPSCs recorded from hippocampal rat cultures in the absence (Fc control, left panel) or presence (Sema4D-Fc, right panel) of Sema4D-Fc treatment for 0.5, 1, 2, and 4 hours of treatment. Quantification of mIPSC frequency (FIG. 4B) and amplitude (FIG. 4B) is also provided (*p<0.05, student's t-test compared to corresponding Fc control). The data are plotted as mean±S.E.M. Cumulative distribution plots of mIPSC interevent intervals (FIG. 4C) and mIPSC amplitude (FIG. 4D) at 0.5, 1, 2, and 4 hours of Sema4D-Fc treatment (*p<0.02, Kolmogorov-Smirnov test) are provided. The results shown in FIGS. 4A-D were derived from analyzing 14 neurons for all conditions in each experiment of three experiments.

FIG. 5A shows representative stretches of dendrite from neurons (wildtype, top panel or PlxnB1−/−, bottom panel) treated with Fc control (left panel) or Sema4D-Fc (right panel) immunostained for the presynaptic protein GAD65, the postsynaptic protein GABA$_A$Rγ2, and MAP2 to visualize dendrites. Scale bars=2 μm. FIG. 5B shows a quantification of inhibitory synapse density (n>58 neurons for each condition, 3 experiments; *p<0.05, two-way ANOVA). FIG. 5C shows representative mIPSCs recorded from wildtype (top panel) or PlxnB1−/− (bottom panel) CA1 neurons in acute hippocampal slice treated with or without Sema4D-Fc for 2 hours. A quantification of mIPSC frequency (FIG. 5D) and mIPSC amplitude (FIG. 5E) (n=29 neurons per condition; *p<0.05 compared to wildtype Fc control treatment, student's t-test) is also provided. For FIGS. 5A-5E, all data are plotted as mean±S.E.M. In addition, cumulative distribution plots of mIPSC interevent intervals (FIG. 5F) and amplitude (FIG. 5G) in wildtype and PlxnB1−/− mice in the absence (Fc Control) or presence of Sema4D-Fc (n=29 neurons each condition, N=4 total experiments; *p<0.02, Kolmogorov-Smirnov test) are shown.

FIG. 6A shows stretches of dendrite from cultured rat hippocampal neurons expressing GFP-Gephyrin and treated with Fc control (left panel) or Sema4D-Fc (right panel). Scale bars=2 μm. Below each dendrite is a kymograph of the region highlighted by the box above that visualizes the movement of puncta over time (B=before treatment, 10=0-10 minutes after treatment, 20=10-20 minutes after treatment, 30=20-30 minutes after treatment; white arrows=puncta splitting event). FIG. 6B shows additional representative kymographs from sample stretches of different dendrites from the same neurons as in FIG. 6A. Scale bars: y-axis=3 min, x-axis=3 μm. The top panel of FIG. 6C shows the number of puncta added (average per neuron) during each imaging session in either Fc control (light grey) or Sema4D treated neurons (dark grey) (*p<0.05, student's t-test). The bottom panel of FIG. 6C shows the average number of GFP-Gephyrin puncta added normalized to the total number of GFP-Gephyrin puncta per neuron (*p<0.05, student's t-test. The top panel of FIG. 6D shows the number of GFP-Gephyrin puncta removed (average per neuron) during the imaging session in either Fc control (light grey) or Sema4D treated neurons (dark grey). FIG. 6D shows the average number of GFP-Gephyrin puncta removed normalized to the total number of GFP-Gephyrin puncta per neuron. The average number of GFP-Gephyrin puncta was not different between conditions. Sema4D-Fc: n=5 neurons, 1025 puncta, average 205 puncta/neuron (±22.75). Fc control: n=3 neurons, 446 puncta, average 148.67 puncta/neuron (±33.9). All data shown are plotted as mean±S.E.M.

FIG. 7A shows representative traces of spontaneous activity observed in untreated (left panel) or TTX-treated slices (TTX-EA, right panel) with either Fc control (top panel) or Sema4D-Fc treatment (bottom panel). FIG. 7B shows quantification of average spike frequency (top panel) and total area (bottom panel) measured from baseline (dashed line) for each condition (n>12 neurons for each condition; *p<0.05, student's t-test). Representative traces of spontaneous inhibitory postsynaptic currents (sIPSCs) (FIG. 7C, left panel) or spontaneous excitatory postsynaptic currents (sEPSCs) (FIG. 7D left panel) observed in untreated (left panel) or TTX-EA slices (1 µM, right panel) with either Fc control (1 nM, top panel) or Sema4D-Fc treatment (1 nM, bottom panel) are shown. A quantification of total inhibitory synaptic charge (FIG. 7C, right panel) or total excitatory synaptic charge (FIG. 7D, right panel) measured from the same cell for each experimental condition are also shown (n=19 neurons for each condition; *p<0.05, student's t-test for the experiments underlying FIGS. 7C and 7D). All data are plotted as mean±S.E.M.

DETAILED DESCRIPTION OF THE INVENTION

Figure 1:
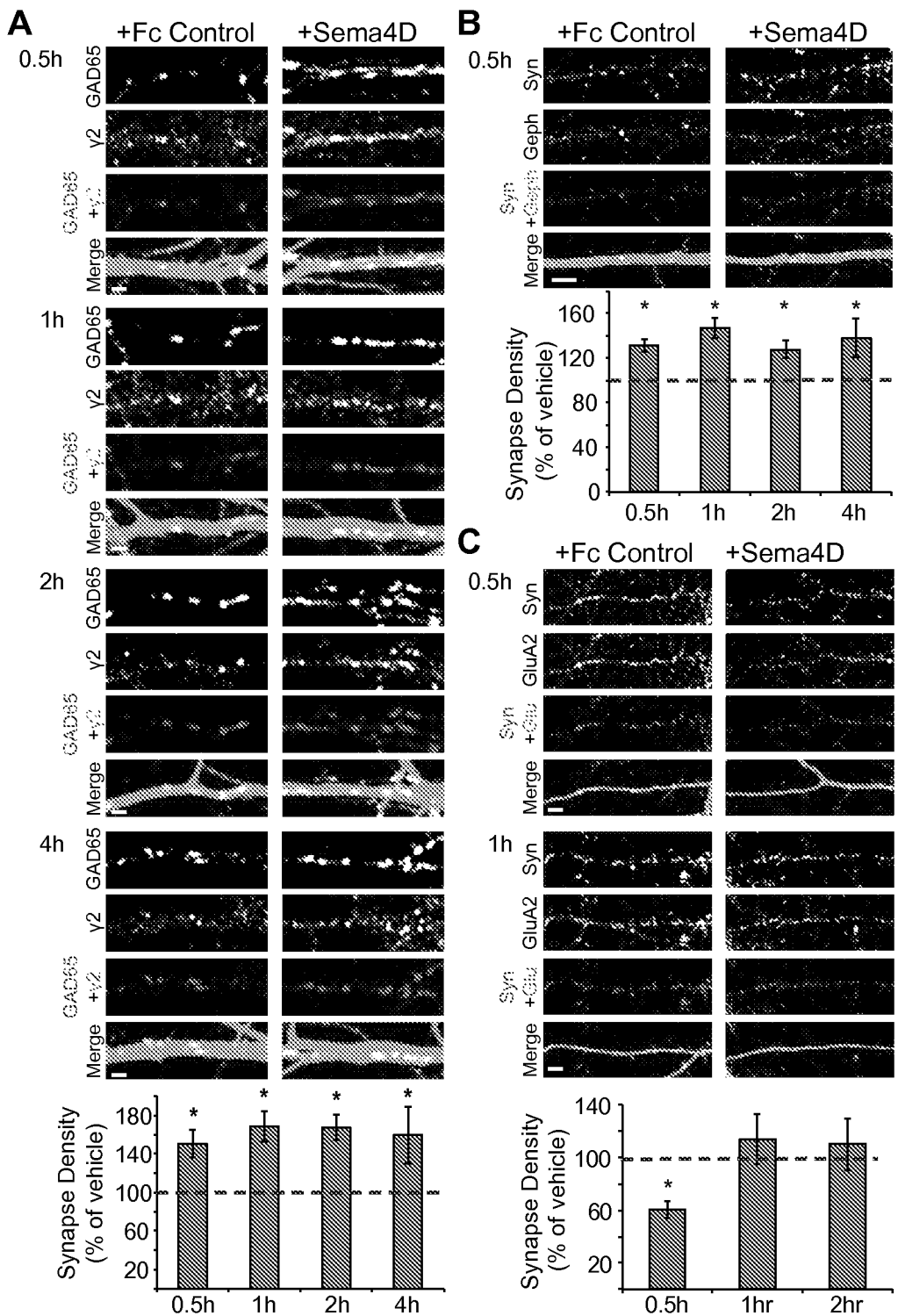
FIGS. 1A-C show that soluble Sema4D-Fc treatment rapidly increases the density of inhibitory synapses. The top panel of FIG. 1A shows representative stretches of dendrite from neurons treated with either Fc control (1 nM) or Sema4D-Fc (1 nM) and immunostained for GAD65, GABA$_A$Rγ2, and MAP2 to visualize dendrites at 0.5, 1, 2, and 4 hours of treatment. Scale bars=2 μm. The bottom panel of FIG. 1A shows a quantification of inhibitory synapse density (GAD65/γ2) at each time point in representative images shown in FIG. 1A as a percentage of synapse density of Fc control treated neurons (100%, represented by dashed line; n>50 neurons in each condition, 3+ experiments). The top panel of FIG. 1B shows representative stretches of dendrite from neurons treated with either Fc control or Sema4D-Fc (1 nM) for 0.5 hours and immunostained for Synapsin I, Gephyrin, and MAP2. Scale bars=5 μm. The bottom panel of FIG. 1B shows a quantification of inhibitory (Gephyrin/Synapsin) synapse density of neurons treated with Sema4D-Fc (1 nM) for 0.5, 1, 2, and 4 hours plotted as percent of Fc control treated neurons (100% represented by dashed line; n>40 neurons in each condition, 2+ experiments). The top panel of FIG. 1C shows representative stretches of dendrite from neurons treated with either Fc control or Sema4D-Fc (1 nM) for 0.5 and 1 hour and immunostained for Synapsin I, GluA2, and MAP2. Scale bars=5 μm. The bottom panel of FIG. 1C shows a quantification of excitatory synapse density of neurons treated 0.5, 1, and 2 hours plotted as a percentage of Fc control treated neurons (100% represented by dashed line; n>45 neurons in each condition, 3+ experiments). For the results of experiments shown in FIGS. 1A-1C, Fc controls at each time point were not significantly different from each other (*p<0.05, two-way ANOVA).

This technology relates to a method of modulating the number of GABAergic synapses between at least two neurons. This method includes contacting at least one of the neurons with a PlexinB agonist or a nucleic acid molecule encoding a PlexinB agonist to promote GABAergic synapse formation.

As used herein, a PlexinB agonist is any compound that stimulates or activates the PlexinB signaling pathway. In one embodiment of the present technology, the PlexinB agonist is a PlexinB1, a PlexinB2, and/or a PlexinB3 agonist. The PlexinB agonist can be a polypeptide or an active peptide fragment or derivative thereof. In yet a further embodiment, the PlexinB agonist binds to and activates the PlexinB1, PlexinB2, and/or PlexinB3 receptor. In one particular embodiment, the PlexinB agonist is a PlexinB1 agonist. In one further particular embodiment, the PlexinB agonist is a Sema4D polypeptide or an active peptide fragment or derivative thereof that binds to and activates the PlexinB1 receptor, such as an extracellular fragment thereof. Other suitable PlexinB agonists include, but are not limited to, members of the Semaphorin protein family or peptides derived from Semaphorins that bind to and activate a PlexinB receptor. Suitable Semaphorins include Semaphorin proteins or peptides that include the extracellular Sema domain. Examples include, but are not limited to, the vertebrate Semaphorins including Sema3A, Sema3B, Sema3C, Sema3D, Sema3E, Sema3F, Sema3G, Sema4A, Sema4B, Sema4C, Sema4D, Sema4E, Sema4F, Sema4G, Sema5A, Sema5B, Sema5C, Sema6A, Sema6B, Sema6C, Sema6D, and Sema7A.

In another embodiment, a nucleic acid molecule encoding a PlexinB agonist or an active peptide fragment or derivative thereof is contacted with at least one of the neurons.

As used herein, "nucleic acid" refers to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

In a further embodiment, the method relates to increasing the number of GABAergic synapses between the at least two neurons. In one particular embodiment, the number of GABAergic synapses formed between the two neurons increases without increasing the number glutamatergic synapses between the two neurons.

In yet another embodiment, at least one of the neurons is an inhibitory neuron, such as an interneuron.

In a further embodiment, the method includes contacting at least one of the neurons with a PlexinB polypeptide or a nucleic acid molecule encoding PlexinB polypeptide. In one embodiment, the PlexinB polypeptide is a PlexinB1 polypeptide.

The PlexinB agonist and the PlexinB polypeptide of the present technology may be any species of origin. For example, Sema4D and PlexinB1 gene sequences and gene product sequences from many species are known, including the native human, non-human primates, rodents and other mammalian, and avian nucleotide sequences, as well as, nucleotide sequences of Sema4D and PlexinB1 variants and analogs, and have been described, for example, in the NCBI Gene database (http://www.ncbi.nlm.nih.gov/gene/?term=plxnb1). Examples include the following sequences:

```
Human Sema4D isoform 1 cDNA nucleic acid sequence (GenBank
Acc. Num. NM_006378; SEQ ID NO: 1):
atgaggatgt gcaccccat taggggctg ctcatggccc ttgcagtgat gtttgggaca      60
gcgatggcat ttgcacccat accccggatc acctgggagc acagagaggt gcacctggtg    120
cagtttcatg agccagacat ctacaactac tcagccttgc tgctgagcga ggacaaggac   180
accttgtaca taggtgcccg ggaggcggtc ttcgctgtga acgcactcaa catctccgag   240
aagcagcatg aggtgtattg gaaggtctca gaagacaaaa aagcaaaatg tgcagaaaag   300
gggaaatcaa aacagacaga gtgcctcaac tacatccggg tgctgcagcc actcagcgcc   360
acttcccttt acgtgtgtgg gaccaacgca ttccagccgg cctgtgacca cctgaactta   420
acatccttta agtttctggg gaaaaatgaa gatggcaaag gaagatgtcc ctttgaccca   480
gcacacagct acacatccgt catggttgat ggagaacttt attcggggac gtcgtataat   540 ttttgggaa gtgaacccat catctcccga aattcttccc acagtcctct gaggacagaa   600
```

-continued

```
tatgcaatcc cttggctgaa cgagcctagt ttcgtgtttg ctgacgtgat ccgaaaaagc    660
ccagacagcc ccgacggcga ggatgacagg gtctacttct tcttcacgga ggtgtctgtg    720
gagtatgagt ttgtgttcag ggtgctgatc ccacggatag caagagtgtg caaggggac     780 cagggcggcc tgaggacctt gcagaagaaa tggacctcct tcctgaaagc ccgactcatc    840
tgctcccggc cagacagcgg cttggtcttc aatgtgctgc gggatgtctt cgtgctcagg    900
tccccgggcc tgaaggtgcc tgtgttctat gcactcttca ccccacagct gaacaacgtg    960
gggctgtcgg cagtgtgcgc ctacaacctg tccacagccg aggaggtctt ctcccacggg   1020
aagtacatgc agagcaccac agtggagcag tcccacacca gtgggtgcg ctataatggc    1080 ccggtaccca agccgcggcc tggagcgtgc atcgacagcg aggcacgggc cgccaactac   1140
accagctcct tgaatttgcc agacaagacg ctgcagttcg ttaaagacca ccctttgatg   1200
gatgactcgg taaccccaat agacaacagg cccaggttaa tcaagaaaga tgtgaactac   1260
acccagatcg tggtggaccg gacccaggcc ctggatggga ctgtctatga tgtcatgttt   1320
gtcagcacag accggggagc tctgcacaaa gccatcagcc tcgagcacgc tgttcacatc   1380
atcgaggaga cccagctctt ccaggacttt gagccagtcc agaccctgct gctgtcttca   1440
aagaagggca acaggtttgt ctatgctggc tctaactcgg gcgtggtcca ggccccgctg   1500
gccttctgtg ggaagcacgg cacctgcgag gactgtgtgc tggcgcggga cccctactgc   1560
gcctggagcc cgcccacagc gacctgcgtg gctctgcacc agaccgagag ccccagcagg   1620
ggtttgattc aggagatgag cggcgatgct tctgtgtgcc cggataaaag taaaggaagt   1680
taccggcagc attttttcaa gcacggtggc acagcggaac tgaaatgctc ccaaaaatcc   1740
aacctggccc gggtcttttg gaagttccag aatggcgtgt tgaaggccga gagccccaag   1800
tacggtctta tgggcagaaa aaacttgctc atcttcaact tgtcagaagg agacagtggg   1860
gtgtaccagt gcctgtcaga ggagagggtt aagaacaaaa cggtcttcca agtggtcgcc   1920
aagcacgtcc tggaagtgaa ggtggttcca aagcccgtag tggcccccac cttgtcagtt   1980
gttcagacag aaggtagtag gattgccacc aaagtgttgg tggcatccac ccaagggtct   2040
tctcccccaa ccccagccgt gcaggccacc tcctccgggg ccatcaccct tcctcccaag   2100
cctgcgccca ccggcacatc ctgcgaacca agatcgtca tcaacacggt cccccagctc    2160
cactcggaga aaaccatgta tcttaagtcc agcgacaacc gcctcctcat gtccctcttc   2220
ctcttcttct ttgttctctt cctctgcctc ttttttctaca actgctataa gggatacctg   2280
cccagacagt gcttgaaatt ccgctcggcc ctactaattg ggaagaagaa gcccaagtca   2340
gatttctgtg accgtgagca gagcctgaag gagacgttag tagagccagg gagcttctcc   2400
cagcagaatg gggagcaccc caagccagcc ctggacaccg gctatgagac cgagcaagac   2460
accatcacca gcaaagtccc cacggatagg gaggactcac agaggatcga cgacctttct   2520
gccagggaca gcccctttga cgtcaagtgt gagctgaagt tcgctgactc agacgcagat   2580
ggagactga                                                          2589
```

Human Sema4D isoform 2 amino acid sequence (GenBank Acc. Num. NP_006369.3; SEQ ID NO: 2):

```
Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60
```

-continued

```
Gly Ala Arg Glu Ala Val Phe Ala Val Asn Ala Leu Asn Ile Ser Glu
 65                  70                  75                  80

Lys Gln His Glu Val Tyr Trp Lys Val Ser Glu Asp Lys Lys Ala Lys
                 85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125

Asn Ala Phe Gln Pro Ala Cys Asp His Leu Asn Leu Thr Ser Phe Lys
    130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
    210                 215                 220

Asp Gly Glu Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Arg Pro Asp Ser Gly Leu
        275                 280                 285

Val Phe Asn Val Leu Arg Asp Val Phe Val Leu Arg Ser Pro Gly Leu
    290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Val Glu Gln Ser His
        340                 345                 350

Thr Lys Trp Val Arg Tyr Asn Gly Pro Val Pro Lys Pro Arg Pro Gly
        355                 360                 365

Ala Cys Ile Asp Ser Glu Ala Arg Ala Ala Asn Tyr Thr Ser Ser Leu
    370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
            420                 425                 430

Gly Thr Val Tyr Asp Val Met Phe Val Ser Thr Asp Arg Gly Ala Leu
        435                 440                 445

His Lys Ala Ile Ser Leu Glu His Ala Val His Ile Ile Glu Glu Thr
    450                 455                 460

Gln Leu Phe Gln Asp Phe Glu Pro Val Gln Thr Leu Leu Leu Ser Ser
465                 470                 475                 480

Lys Lys Gly Asn Arg Phe Val Tyr Ala Gly Ser Asn Ser Gly Val Val
                485                 490                 495
```

```
Gln Ala Pro Leu Ala Phe Cys Gly Lys His Gly Thr Cys Glu Asp Cys
            500                 505                 510
Val Leu Ala Arg Asp Pro Tyr Cys Ala Trp Ser Pro Thr Ala Thr
            515                 520                 525
Cys Val Ala Leu His Gln Thr Glu Ser Pro Ser Arg Gly Leu Ile Gln
            530                 535                 540
Glu Met Ser Gly Asp Ala Ser Val Cys Pro Asp Lys Ser Lys Gly Ser
545                 550                 555                 560
Tyr Arg Gln His Phe Phe Lys His Gly Gly Thr Ala Glu Leu Lys Cys
                565                 570                 575
Ser Gln Lys Ser Asn Leu Ala Arg Val Phe Trp Lys Phe Gln Asn Gly
            580                 585                 590
Val Leu Lys Ala Glu Ser Pro Lys Tyr Gly Leu Met Gly Arg Lys Asn
            595                 600                 605
Leu Leu Ile Phe Asn Leu Ser Glu Gly Asp Ser Gly Val Tyr Gln Cys
            610                 615                 620
Leu Ser Glu Glu Arg Val Lys Asn Lys Thr Val Phe Gln Val Val Ala
625                 630                 635                 640
Lys His Val Leu Glu Val Lys Val Val Pro Lys Pro Val Ala Pro
                645                 650                 655
Thr Leu Ser Val Val Gln Thr Glu Gly Ser Arg Ile Ala Thr Lys Val
            660                 665                 670
Leu Val Ala Ser Thr Gln Gly Ser Ser Pro Pro Thr Pro Ala Val Gln
            675                 680                 685
Ala Thr Ser Ser Gly Ala Ile Thr Leu Pro Pro Lys Pro Ala Pro Thr
            690                 695                 700
Gly Thr Ser Cys Glu Pro Lys Ile Val Ile Asn Thr Val Pro Gln Leu
705                 710                 715                 720
His Ser Glu Lys Thr Met Tyr Leu Lys Ser Ser Asp Asn Arg Leu Leu
                725                 730                 735
Met Ser Leu Phe Leu Phe Phe Val Leu Phe Leu Cys Leu Phe Phe
            740                 745                 750
Tyr Asn Cys Tyr Lys Gly Tyr Leu Pro Arg Gln Cys Leu Lys Phe Arg
            755                 760                 765
Ser Ala Leu Leu Ile Gly Lys Lys Pro Lys Ser Asp Phe Cys Asp
            770                 775                 780
Arg Glu Gln Ser Leu Lys Glu Thr Leu Val Glu Pro Gly Ser Phe Ser
785                 790                 795                 800
Gln Gln Asn Gly Glu His Pro Lys Pro Ala Leu Asp Thr Gly Tyr Glu
                805                 810                 815
Thr Glu Gln Asp Thr Ile Thr Ser Lys Val Pro Thr Asp Arg Glu Asp
            820                 825                 830
Ser Gln Arg Ile Asp Asp Leu Ser Ala Arg Asp Lys Pro Phe Asp Val
            835                 840                 845
Lys Cys Glu Leu Lys Phe Ala Asp Ser Asp Ala Asp Gly Asp
            850                 855                 860

Human Sema4D isoform 2 cDNA nucleic acid sequence (GenBank
Acc. Num. NM_001142287.1; SEQ ID NO: 3):
atgaggatgt gcaccccccat taggggggctg ctcatggccc ttgcagtgat gtttgggaca      60
gcgatggcat ttgcacccat accccggatc acctgggagc acagagaggt gcacctggtg     120
cagtttcatg agccagacat ctacaactac tcagccttgc tgctgagcga ggacaaggac     180
accttgtaca taggtgcccg ggaggcggtc ttcgctgtga acgcactcaa catctccgag     240
aagcagcatg aggtgtattg gaaggtctca gaagacaaaa agcaaaatg tgcagaaaag     300
```

-continued

```
gggaaatcaa aacagacaga gtgcctcaac tacatccggg tgctgcagcc actcagcgcc    360
acttcccttt acgtgtgtgg gaccaacgca ttccagccgg cctgtgacca cctgaactta    420 acatcccttta agtttctggg gaaaaatgaa gatggcaaag gaagatgtcc ctttgaccca    480
gcacacagct acacatccgt catggttgat ggagaacttt attcggggac gtcgtataat    540
tttttgggaa gtgaacccat catctcccga aattcttccc acagtcctct gaggacagaa    600
tatgcaatcc cttggctgaa cgagcctagt ttcgtgtttg ctgacgtgat ccgaaaaagc    660
ccagacagcc ccgacggcga ggatgacagg gtctacttct tcttcacgga ggtgtctgtg    720
gagtatgagt ttgtgttcag ggtgctgatc ccacggatag caagagtgtg caagggggac    780
cagggcggcc tgaggacctt gcagaagaaa tggacctcct tcctgaaagc ccgactcatc    840
tgctcccggc cagacagcgg cttggtcttc aatgtgctgc gggatgtctt cgtgctcagg    900
tccccgggcc tgaaggtgcc tgtgttctat gcactcttca ccccacagct gaacaacgtg    960
gggctgtcgg cagtgtgcgc ctacaacctg tccacagccg aggaggtctt ctcccacggg   1020
aagtacatgc agagcaccac agtggagcag tcccacacca gtgggtgcg ctataatggc   1080 ccggtaccca agccgcggcc tggagcgtgc atcgacagcg aggcacgggc cgccaactac   1140
accagctcct tgaatttgcc agacaagacg ctgcagttcg ttaaagacca ccctttgatg   1200
gatgactcgg taaccccaat agacaacagg cccaggttaa tcaagaaaga tgtgaactac    1260
acccagatcg tggtggaccg gacccaggcc ctggatggga ctgtctatga tgtcatgttt   1320
gtcagcacag accggggagc tctgcacaaa gccatcagcc tcgagcacgc tgttcacatc   1380
atcgaggaga cccagctctt ccaggacttt gagccagtcc agaccctgct gctgtcttca   1440
aagaagggca acaggtttgt ctatgctggc tctaactcgg gcgtggtcca ggccccgctg   1500
gccttctgtg ggaagcacgg cacctgcgag gactgtgtgc tggcgcggga cccctactgc   1560
gcctggagcc cgcccacagc gacctgcgtg gctctgcacc agaccgagag ccccagcagg   1620
ggtttgattc aggagatgag cggcgatgct tctgtgtgcc cggcctcgtc tcctaagccc   1680
ctccctcctc ctggctcctc ttccctgtcc tgtctgggcc atgtggggga caggaggctt   1740
tcctctccct ggacccctg gccagcctcg ggtgcggggc ccgacagcag ctcgagggtc   1800
tccttgctgc cgcccttcct gagtgaccag gcacagcacg tgcacgccct ggggaacttc   1860
tacctcttct gccaggccac aggtcctgca gacattcgct ttgtctggga agaatggg    1920 cgagctctgg agacctgtgt ccctgtgcag acccatgcac tgcccgatgg cagggcccat   1980
gcactcagct ggctgcagga cgccatcagg gaaagcgctg agtatcgctg ctctgtcctc   2040
tcctcagcag ggaacaagac ttcgaaggtg caggttgctg tgatgagacc tgaagtgacc   2100
caccaggaga ggtggaccag agagctctct gcctggaggg ctgtggctgg ggagcacgac   2160
cggatgatgc agagctggag gaaggcgtgg gaaagctgta gcaaggacac cctgtag     2217
```

Human Sema4D isoform 2 amino acid sequence (GenBank Acc. Num. NP_001142287.1; SEQ ID NO: 4):

```
Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
                20                  25                  30

Glu His Arg Glu Val His Leu Val Gln Phe His Glu Pro Asp Ile Tyr
            35                  40                  45

Asn Tyr Ser Ala Leu Leu Leu Ser Glu Asp Lys Asp Thr Leu Tyr Ile
        50                  55                  60

Gly Ala Arg Glu Ala Val Phe Ala Val Asn Ala Leu Asn Ile Ser Glu
65                  70                  75                  80
```

```
Lys Gln His Glu Val Tyr Trp Lys Val Ser Glu Asp Lys Lys Ala Lys
                85                  90                  95
Cys Ala Glu Lys Gly Lys Ser Lys Gln Thr Glu Cys Leu Asn Tyr Ile
            100                 105                 110
Arg Val Leu Gln Pro Leu Ser Ala Thr Ser Leu Tyr Val Cys Gly Thr
        115                 120                 125
Asn Ala Phe Gln Pro Ala Cys Asp His Leu Asn Leu Thr Ser Phe Lys
130                 135                 140
Phe Leu Gly Lys Asn Glu Asp Gly Lys Gly Arg Cys Pro Phe Asp Pro
145                 150                 155                 160
Ala His Ser Tyr Thr Ser Val Met Val Asp Gly Glu Leu Tyr Ser Gly
                165                 170                 175
Thr Ser Tyr Asn Phe Leu Gly Ser Glu Pro Ile Ile Ser Arg Asn Ser
            180                 185                 190
Ser His Ser Pro Leu Arg Thr Glu Tyr Ala Ile Pro Trp Leu Asn Glu
        195                 200                 205
Pro Ser Phe Val Phe Ala Asp Val Ile Arg Lys Ser Pro Asp Ser Pro
    210                 215                 220
Asp Gly Glu Asp Asp Arg Val Tyr Phe Phe Thr Glu Val Ser Val
225                 230                 235                 240
Glu Tyr Glu Phe Val Phe Arg Val Leu Ile Pro Arg Ile Ala Arg Val
                245                 250                 255
Cys Lys Gly Asp Gln Gly Gly Leu Arg Thr Leu Gln Lys Lys Trp Thr
            260                 265                 270
Ser Phe Leu Lys Ala Arg Leu Ile Cys Ser Arg Pro Asp Ser Gly Leu
        275                 280                 285
Val Phe Asn Val Leu Arg Asp Val Phe Val Leu Arg Ser Pro Gly Leu
    290                 295                 300
Lys Val Pro Val Phe Tyr Ala Leu Phe Thr Pro Gln Leu Asn Asn Val
305                 310                 315                 320
Gly Leu Ser Ala Val Cys Ala Tyr Asn Leu Ser Thr Ala Glu Glu Val
                325                 330                 335
Phe Ser His Gly Lys Tyr Met Gln Ser Thr Thr Val Glu Gln Ser His
            340                 345                 350
Thr Lys Trp Val Arg Tyr Asn Gly Pro Val Pro Lys Pro Arg Pro Gly
        355                 360                 365
Ala Cys Ile Asp Ser Glu Ala Arg Ala Ala Asn Tyr Thr Ser Ser Leu
    370                 375                 380
Asn Leu Pro Asp Lys Thr Leu Gln Phe Val Lys Asp His Pro Leu Met
385                 390                 395                 400
Asp Asp Ser Val Thr Pro Ile Asp Asn Arg Pro Arg Leu Ile Lys Lys
                405                 410                 415
Asp Val Asn Tyr Thr Gln Ile Val Val Asp Arg Thr Gln Ala Leu Asp
            420                 425                 430
Gly Thr Val Tyr Asp Val Met Phe Val Ser Thr Asp Arg Gly Ala Leu
        435                 440                 445
His Lys Ala Ile Ser Leu Glu His Ala Val His Ile Ile Glu Glu Thr
    450                 455                 460
Gln Leu Phe Gln Asp Phe Glu Pro Val Gln Thr Leu Leu Leu Ser Ser
465                 470                 475                 480
Lys Lys Gly Asn Arg Phe Val Tyr Ala Gly Ser Asn Ser Gly Val Val
                485                 490                 495
Gln Ala Pro Leu Ala Phe Cys Gly Lys His Gly Thr Cys Glu Asp Cys
            500                 505                 510
```

-continued

```
Val Leu Ala Arg Asp Pro Tyr Cys Ala Trp Ser Pro Pro Thr Ala Thr
            515                 520                 525

Cys Val Ala Leu His Gln Thr Glu Ser Pro Ser Arg Gly Leu Ile Gln
    530                 535                 540

Glu Met Ser Gly Asp Ala Ser Val Cys Pro Ala Ser Ser Pro Lys Pro
545                 550                 555                 560

Leu Pro Pro Pro Gly Ser Ser Leu Ser Cys Leu Gly His Val Gly
                565                 570                 575

Asp Arg Arg Leu Ser Ser Pro Trp Thr Pro Trp Pro Ala Ser Gly Ala
                580                 585                 590

Gly Pro Asp Ser Ser Ser Arg Val Ser Leu Leu Pro Pro Phe Leu Ser
            595                 600                 605

Asp Gln Ala Gln His Val His Ala Leu Gly Asn Phe Tyr Leu Phe Cys
            610                 615                 620

Gln Ala Thr Gly Pro Ala Asp Ile Arg Phe Val Trp Glu Lys Asn Gly
625                 630                 635                 640

Arg Ala Leu Glu Thr Cys Val Pro Val Gln Thr His Ala Leu Pro Asp
                645                 650                 655

Gly Arg Ala His Ala Leu Ser Trp Leu Gln Asp Ala Ile Arg Glu Ser
            660                 665                 670

Ala Glu Tyr Arg Cys Ser Val Leu Ser Ser Ala Gly Asn Lys Thr Ser
            675                 680                 685

Lys Val Gln Val Ala Val Met Arg Pro Glu Val Thr His Gln Glu Arg
            690                 695                 700

Trp Thr Arg Glu Leu Ser Ala Trp Arg Ala Val Ala Gly Glu His Asp
705                 710                 715                 720

Arg Met Met Gln Ser Trp Arg Lys Ala Trp Glu Ser Cys Ser Lys Asp
                725                 730                 735

Thr Leu
```

Mouse Sema4D cDNA nucleic acid sequence (GenBank Acc. Num. NM_013660.3; SEQ ID NO: 5):

```
atgaggatgt gtgcccccgt taggggggctg ttcttggccc tggtggtagt gttgagaacc    60
gcggtggcat tgcacctgt gcctcggctc acctgggaac atggagaggt aggtctggtg    120
cagtttcaca agccaggcat ctttaactac tcggccttgc tgatgagtga ggacaaagac    180
actctgtatg taggcgcccg ggaagcagtc tttgcagtga atgcgctgaa catctctgag    240
aagcaacatg aggtatattg gaaggtctct gaagacaaaa atccaagtg tgcagagaag    300
gggaaatcaa agcagacgga atgcctaaac tacattcgag tactacagcc actaagcagc    360
acttccctct atgtgtgtgg gaccaatgcg ttccagccca cctgtgacca cctgaacttg    420
acatccttca gtttctggg gaaaagtgaa gatggcaaag aagatgcccc cttcgacccc    480
gcccacagct acacatcagt catggttggg ggcgagctct actctgggac gtcctataat    540
ttcttgggca gtgaacccat catctctcga aactcttccc acagtccctt gaggacggag    600
tatgccatcc gtggctgaa cgagcctagc ttcgtctttg ctgacgtgat ccagaaaagc    660
ccagatggtc cggagggtga agatgacaag gtctacttct tttttacgga ggtatccgtg    720
gagtacgaat tcgtcttcaa gttgatgatc ccgcgagttg ccagggtgtg caagggcgac    780
cagggcggcc tgcggacttt gcaaaaaaag tggacctcct tcctaaaggc caggctgatc    840
tgctccaagc cagacagtgg cctggtcttc aacatacttc aggatgtgtt tgtgctgagg    900
gccccgggcc tcaaggagcc tgtgttctat gcggtcttca ccccacagct gaacaatgtg    960
ggtctgtcag cggtgtgcgc ctacacactg gccacggtgg aggcagtctt ctcccgtgga    1020
aagtacatgc agagtgccac agtggagcag tctcacacca gtgggtgcg ctacaatgcc    1080
```

-continued

```
ccagtgccca ctccccgacc tggagcgtgt atcgacagtg aggcccgggc agccaactac   1140
accagctcct tgaatctccc agacaaaaca ctgcagtttg taaaagacca cccttttgatg  1200
gatgactcag tgaccccgat agacaacaga cccaagctga tcaaaaaaga tgtaaactac   1260
acccagatag tggtagacag gacccaggcc ctggatggga ctttctacga cgtcatgttc   1320
atcagcacag accggggagc tctgcataaa gcagtcatcc tcacaaaaga ggtgcatgtc   1380
atcgaggaga cccaactctt ccgggactct gaaccggtcc taactctgct gctatcgtca   1440
aagaagggga ggaagtttgt ctatgcaggc tccaactctg gagtggtcca agcgccctg    1500
gcattctgcg aaaagcacgg tagctgtgaa gactgtgtgt tagcacggga ccctactgt    1560
gcctggagcc cagccatcaa ggcctgtgtt accctgcacc aggaagaggc ctccagcagg   1620
ggctggattc aggacatgag cggtgacaca tcctcatgcc tggataagag taaagaaagt   1680
ttcaaccagc attttttcaa gcacggcggc acagcggaac tcaaatgttt ccaaaagtcc   1740
aacctagccc gggtggtatg gaagttccag aatggcgagt tgaaggccgc aagtcccaag   1800
tacggctttg tgggcaggaa gcacctgctc atcttcaacc tgtcggacgg agacagcggc   1860
gtgtaccagt gcctgtcaga ggaaaggggtg aggaataaaa cggtctccca gctgctggcc  1920
aagcacgttc tggaagtgaa gatggtacct cggacccccc cctcacctac ctcagaggat   1980
gctcagacag aaggtagtaa gatcacatcc aaaatgccgg ttgcatctac ccaggggtcc   2040
tctccccta ccccggctct gtgggcaacc tcccccagag ccgccaccct acctcccaag    2100
tcctcctccg gcacatcctg tgaaccaaag atggtcatca acacggtccc ccagctccac   2160
tcagagaaga cggtgtatct caagtccagt gacaaccgcc tgctcatgtc tctcctcctc   2220
ttcatctttg tcctcttcct ctgcctcttt tcctacaact gctacaaggg ctacctgccc   2280
ggacagtgct taaaattccg ctcagccctg ctgcttggaa agaaaacacc caagtcagac   2340
ttctctgacc tggagcagag tgtgaaggag acactggtcg agcctgggag cttctcccag   2400
cagaacggcg accaccccaa gccagccctg gatacgggct atgaaacgga gcaggacacc   2460
atcaccagca aagtccccac ggatcgtgag gactcgcaac ggatcgatga actctctgcc   2520
cgggacaaaac cgtttgatgt caagtgtgaa ctgaagtttg cagattcgga tgctgacggg   2580
gactga                                                              2586
```

Mouse Sema4D amino acid sequence (GenBank Acc. Num. NP_038688.2; SEQ ID NO: 6):

```
Met Arg Met Cys Ala Pro Val Arg Gly Leu Phe Leu Ala Leu Val Val
1               5                   10                  15

Val Leu Arg Thr Ala Val Ala Phe Ala Pro Val Pro Arg Leu Thr Trp
            20                  25                  30

Glu His Gly Glu Val Gly Leu Val Gln Phe His Lys Pro Gly Ile Phe
        35                  40                  45

Asn Tyr Ser Ala Leu Leu Met Ser Glu Asp Lys Asp Thr Leu Tyr Val
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ser Lys
                85                  90                  95

Cys Ala Glu Lys Gly Lys Ser Gln Thr Glu Cys Leu Asn Tyr Ile
            100                 105                 110

Arg Val Leu Gln Pro Leu Ser Ser Thr Ser Leu Tyr Val Cys Gly Thr
        115                 120                 125

Asn Ala Phe Gln Pro Thr Cys Asp His Leu Asn Leu Ser Phe Lys
    130                 135                 140
```

```
Phe Leu Gly Lys Ser Glu Asp Gly Lys Gly Arg Cys Pro Phe Asp Pro
145                 150                 155                 160

Ala His Ser Tyr Thr Ser Val Met Val Gly Gly Glu Leu Tyr Ser Gly
            165                 170                 175

Thr Ser Tyr Asn Phe Leu Gly Ser Glu Pro Ile Ile Ser Arg Asn Ser
        180                 185                 190

Ser His Ser Pro Leu Arg Thr Glu Tyr Ala Ile Pro Trp Leu Asn Glu
    195                 200                 205

Pro Ser Phe Val Phe Ala Asp Val Ile Gln Lys Ser Pro Asp Gly Pro
210                 215                 220

Glu Gly Glu Asp Asp Lys Val Tyr Phe Phe Thr Glu Val Ser Val
225                 230                 235                 240

Glu Tyr Glu Phe Val Phe Lys Leu Met Ile Pro Arg Val Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Lys Pro Asp Ser Gly Leu
        275                 280                 285

Val Phe Asn Ile Leu Gln Asp Val Phe Val Leu Arg Ala Pro Gly Leu
    290                 295                 300

Lys Glu Pro Val Phe Tyr Ala Val Phe Thr Pro Gln Leu Asn Asn Val
305                 310                 315                 320

Gly Leu Ser Ala Val Cys Ala Tyr Thr Leu Ala Thr Val Glu Ala Val
                325                 330                 335

Phe Ser Arg Gly Lys Tyr Met Gln Ser Ala Thr Val Glu Gln Ser His
            340                 345                 350

Thr Lys Trp Val Arg Tyr Asn Gly Pro Val Pro Thr Pro Arg Pro Gly
        355                 360                 365

Ala Cys Ile Asp Ser Glu Ala Arg Ala Ala Asn Tyr Thr Ser Ser Leu
    370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Lys Leu Ile Lys Lys
                405                 410                 415

Asp Val Asn Tyr Thr Gln Ile Val Val Asp Arg Thr Gln Ala Leu Asp
            420                 425                 430

Gly Thr Phe Tyr Asp Val Met Phe Ile Ser Thr Asp Arg Gly Ala Leu
        435                 440                 445

His Lys Ala Val Ile Leu Thr Lys Glu Val His Val Ile Glu Glu Thr
    450                 455                 460

Gln Leu Phe Arg Asp Ser Glu Pro Val Leu Thr Leu Leu Ser Ser
465                 470                 475                 480

Lys Lys Gly Arg Lys Phe Val Tyr Ala Gly Ser Asn Ser Gly Val Val
                485                 490                 495

Gln Ala Pro Leu Ala Phe Cys Glu Lys His Gly Ser Cys Glu Asp Cys
            500                 505                 510

Val Leu Ala Arg Asp Pro Tyr Cys Ala Trp Ser Pro Ala Ile Lys Ala
        515                 520                 525

Cys Val Thr Leu His Gln Glu Ala Ser Ser Arg Gly Trp Ile Gln
    530                 535                 540

Asp Met Ser Gly Asp Thr Ser Ser Cys Leu Asp Lys Ser Lys Glu Ser
545                 550                 555                 560

Phe Asn Gln His Phe Phe Lys His Gly Gly Thr Ala Glu Leu Lys Cys
                565                 570                 575
```

-continued

```
Phe Gln Lys Ser Asn Leu Ala Arg Val Val Trp Lys Phe Gln Asn Gly
            580                 585                 590

Glu Leu Lys Ala Ala Ser Pro Lys Tyr Gly Phe Val Gly Arg Lys His
        595                 600                 605

Leu Leu Ile Phe Asn Leu Ser Asp Gly Asp Ser Gly Val Tyr Gln Cys
    610                 615                 620

Leu Ser Glu Glu Arg Val Arg Asn Lys Thr Val Ser Gln Leu Leu Ala
625                 630                 635                 640

Lys His Val Leu Glu Val Lys Met Val Pro Arg Thr Pro Ser Pro
                645                 650                 655

Thr Ser Glu Asp Ala Gln Thr Glu Gly Ser Lys Ile Thr Ser Lys Met
            660                 665                 670

Pro Val Ala Ser Thr Gln Gly Ser Ser Pro Pro Thr Pro Ala Leu Trp
        675                 680                 685

Ala Thr Ser Pro Arg Ala Ala Thr Leu Pro Pro Lys Ser Ser Ser Gly
    690                 695                 700

Thr Ser Cys Glu Pro Lys Met Val Ile Asn Thr Val Pro Gln Leu His
705                 710                 715                 720

Ser Glu Lys Thr Val Tyr Leu Lys Ser Ser Asp Asn Arg Leu Leu Met
                725                 730                 735

Ser Leu Leu Leu Phe Ile Phe Val Leu Phe Leu Cys Leu Phe Ser Tyr
            740                 745                 750

Asn Cys Tyr Lys Gly Tyr Leu Pro Gly Gln Cys Leu Lys Phe Arg Ser
        755                 760                 765

Ala Leu Leu Leu Gly Lys Lys Thr Pro Lys Ser Asp Phe Ser Asp Leu
    770                 775                 780

Glu Gln Ser Val Lys Glu Thr Leu Val Glu Pro Gly Ser Phe Ser Gln
785                 790                 795                 800

Gln Asn Gly Asp His Pro Lys Pro Ala Leu Asp Thr Gly Tyr Glu Thr
                805                 810                 815

Glu Gln Asp Thr Ile Thr Ser Lys Val Pro Thr Asp Arg Glu Asp Ser
            820                 825                 830

Gln Arg Ile Asp Glu Leu Ser Ala Arg Asp Lys Pro Phe Asp Val Lys
        835                 840                 845

Cys Glu Leu Lys Phe Ala Asp Ser Asp Ala Asp Gly Asp
    850                 855                 860
```

Rat Sema4D cDNA nucleic acid sequence (GenBank Acc. Num. XM_225215.4; SEQ ID NO: 7):

```
atgaagatgt gtgccccccgt caggggggctg ttcttggccc tggtggctgt gtggaggacc    60
gcggtggcat tcgcccctgt gcctcggatc acctgggagc acggagaggt aggtctggtg   120
aaccttcacg agccaggcat ctttaactac tcttccttgc tgatgacaag ccacaaggat   180
cctcctgtct ctgcctcccc aattggggct gcagtgaacc ggctctgaca tgttcccccc   240
tcacaggtat actggaaggt ctctgaagac aaaaaatcca agtgcgcaga gaaggggaaa   300
tcaaagcaga cggagtgcct taactacatc cgagtgctgc aaccgcttag cagcacttcc   360
ctctacgtgt gtgggaccaa tgcgttccag cccacctgtg accacctgaa cttgacctct   420
ttcaagtttc tggggaaaag cgaagatggc aaaggaagat gccccttcga ccccgcccat   480
agctacacat ccgtcatggt cggggagag ctctactctg ggacttcata taatttcttg   540
ggcagcgaac ccatcatctc tcgaaactct cccacagtc ccctgaggac agagtacgcc   600
atcccttggc taaacgagcc tagcttcgtc tttgctgacg tgatccacaa gagcccagat   660
ggtacagagg ctgaggatga caaggtctac ttcttcttta cggaggtgtc cgtggagtac   720
```

-continued

```
gagttcgtct tcaagttgat gatcccgcga gttgccaggg tgtgcaaggg cgaccagggc    780
ggcctgcgga cttgcaaaa aaagtggacc tccttcctaa aggccagact gatctgctcc    840
aggccagaca gtggcctggt cttcaacatt cttcaagatg tgtttgtgct gagggccccg    900
ggcctcaagg aacctgtgtt ctatgcggtc ttcaccccac agctgaacaa cgtgggtctg    960
tcagcggtct gtgcctacac gctgtccacg gtggaggccg tcttctcccg aggaaagtac   1020
atgcagagtg ccacagtgga gcagtctcac accaagtggg tacgctacaa tggcccagtg   1080
cccactcccc ggcctggagc gtgtatcgac agtgaggccc gggcagccaa ctacaccagc   1140
tccttgaatc tcccagacaa aacgctgcag tttgtcaaag accacccttt gatggacgac   1200
tcggtgacgc aatagacaa caggccgaaa ctgatcaaaa agatgtcaa ctacacccag    1260
atagtggtag acaggaccca ggccctggat gggaccttct acgacgtcat gttcctcagc   1320
acagaccggg gcgctctgca taaagctgtc atccttgcaa aagaggtaca cgtggttgag   1380
gagacccaac tcttccagga cttcgaaccg gtcctgtctc tgctgctatc atcaaagaag   1440
gggaggaagt ttgtctatgc tggctccaac tcaggagtgg tccaagctcc cctggccttc   1500
tgcggaaagc acagtagctg tgaagactgt gtgctagcac gggacccta ctgcgcctgg   1560
agcccagcca tcaaggcctg tgttaccttg caccaggcag agggctctag caggggctgg   1620
attcaggaca tgagtggcga cacgtcctcg tgcctggata gagtaaaga agtttccat    1680
cagcattttt tcaagcacgg cggcacagca gaactcaagt gtttccaaaa gtccaacctg   1740
gcccgggtgg tgtggaagtt ccagaacggc gagttgaagg ctgtgagtcc caagtatggc   1800
tttgtgggca ggaagcacct gctcatcttt aacctgtcag acggagacag cggtgtgtac   1860
cagtgcctgt cagaggaaag ggtcaggaat aaaacggtct cccagctgct cgccaagcac   1920
atcctggaag tgaaaatggt agctcggatc cccccatcac ctacctcaca gactgctcag   1980
acagaaggta gtaggatcac atccaaaatg cctgtggcgt ctacccaggg gtcctctccc   2040
cctaccccgg ctctgtgggc aacctccccc agggctgcca ccctacctcc caagtcctcc   2100
tccaccggca cgtcctgtga accaaaaatg gtcatcaaca cggtcccaca gctccactcg   2160
gagaagacag tgtatctcaa gtccagtgac aaccgcctgc tcatgtctct cctcctcttc   2220
ctctttgtcc tcttcctctg cctctttttcc tacaactgct acaagggcta cctgcccgga   2280
cagtgcttaa agttccgctc agccctgctg ctcgcaaaga aaaacccaa gtcagagttc   2340
tctgacctgg agcagagtgt gaaggagacg ctggtagaac tgggagctt ctcgcagcag   2400
aacggcgacc agcccaagcc agccttggat accggctatg aaaccgagca ggacactatc   2460
accagcaagg tccccaccga tcgagaggac tcgcaacgta tcgacgagct ctccgccagg   2520
gacaaaccgt tgatgtcaa gtgtgaactc aagtttgcag actcggatgc cgacggggac   2580
tga                                                                2583
```

Rat Sema4D amino acid sequence (GenBank Acc. Num.
XP_ 225215.4; SEQ ID NO: 8):

```
Met Lys Met Cys Ala Pro Val Arg Gly Leu Phe Leu Ala Leu Val Ala
1               5                   10                  15

Val Trp Arg Thr Ala Val Ala Phe Ala Pro Val Pro Arg Ile Thr Trp
            20                  25                  30

Glu His Gly Glu Val Gly Leu Val Asn Leu His Glu Pro Gly Ile Phe
        35                  40                  45

Asn Tyr Ser Ser Leu Leu Met Thr Ser His Lys Asp Pro Pro Val Ser
    50                  55                  60

Ala Ser Pro Ile Gly Ala Ala Val Asn Arg Leu Xaa His Val Pro Pro
65                  70                  75                  80
```

```
Ser Gln Val Tyr Trp Lys Val Ser Glu Asp Lys Lys Ser Lys Cys Ala
                 85                  90                  95

Glu Lys Gly Lys Ser Lys Gln Thr Glu Cys Leu Asn Tyr Ile Arg Val
            100                 105                 110

Leu Gln Pro Leu Ser Ser Thr Ser Leu Tyr Val Cys Gly Thr Asn Ala
        115                 120                 125

Phe Gln Pro Thr Cys Asp His Leu Asn Leu Thr Ser Phe Lys Phe Leu
    130                 135                 140

Gly Lys Ser Glu Asp Gly Lys Gly Arg Cys Pro Phe Asp Pro Ala His
145                 150                 155                 160

Ser Tyr Thr Ser Val Met Val Gly Gly Glu Leu Tyr Ser Gly Thr Ser
                165                 170                 175

Tyr Asn Phe Leu Gly Ser Glu Pro Ile Ile Ser Arg Asn Ser Ser His
            180                 185                 190

Ser Pro Leu Arg Thr Glu Tyr Ala Ile Pro Trp Leu Asn Glu Pro Ser
        195                 200                 205

Phe Val Phe Ala Asp Val Ile His Lys Ser Pro Asp Gly Thr Glu Ala
    210                 215                 220

Glu Asp Asp Lys Val Tyr Phe Phe Thr Glu Val Ser Val Glu Tyr
225                 230                 235                 240

Glu Phe Val Phe Lys Leu Met Ile Pro Arg Val Ala Arg Val Cys Lys
                245                 250                 255

Gly Asp Gln Gly Gly Leu Arg Thr Leu Gln Lys Lys Trp Thr Ser Phe
            260                 265                 270

Leu Lys Ala Arg Leu Ile Cys Ser Arg Pro Asp Ser Gly Leu Val Phe
        275                 280                 285

Asn Ile Leu Gln Asp Val Phe Val Leu Arg Ala Pro Gly Leu Lys Glu
    290                 295                 300

Pro Val Phe Tyr Ala Val Phe Thr Pro Gln Leu Asn Asn Val Gly Leu
305                 310                 315                 320

Ser Ala Val Cys Ala Tyr Thr Leu Ser Thr Val Glu Ala Val Phe Ser
                325                 330                 335

Arg Gly Lys Tyr Met Gln Ser Ala Thr Val Glu Gln Ser His Thr Lys
            340                 345                 350

Trp Val Arg Tyr Asn Gly Pro Val Pro Thr Pro Arg Pro Gly Ala Cys
        355                 360                 365

Ile Asp Ser Glu Ala Arg Ala Ala Asn Tyr Thr Ser Ser Leu Asn Leu
    370                 375                 380

Pro Asp Lys Thr Leu Gln Phe Val Lys Asp His Pro Leu Met Asp Asp
385                 390                 395                 400

Ser Val Thr Pro Ile Asp Asn Arg Pro Lys Leu Ile Lys Lys Asp Val
                405                 410                 415

Asn Tyr Thr Gln Ile Val Val Asp Arg Thr Gln Ala Leu Asp Gly Thr
            420                 425                 430

Phe Tyr Asp Val Met Phe Leu Ser Thr Asp Arg Gly Ala Leu His Lys
        435                 440                 445

Ala Val Ile Leu Ala Lys Glu Val His Val Val Glu Glu Thr Gln Leu
    450                 455                 460

Phe Gln Asp Phe Glu Pro Val Leu Ser Leu Leu Leu Ser Ser Lys Lys
465                 470                 475                 480

Gly Arg Lys Phe Val Tyr Ala Gly Ser Asn Ser Gly Val Val Gln Ala
                485                 490                 495

Pro Leu Ala Phe Cys Gly Lys His Ser Ser Cys Glu Asp Cys Val Leu
            500                 505                 510
```

```
Ala Arg Asp Pro Tyr Cys Ala Trp Ser Pro Ala Ile Lys Ala Cys Val
    515                 520                 525

Thr Leu His Gln Ala Glu Gly Ser Ser Arg Gly Trp Ile Gln Asp Met
530                 535                 540

Ser Gly Asp Thr Ser Ser Cys Leu Asp Lys Ser Lys Glu Ser Phe His
545                 550                 555                 560

Gln His Phe Phe Lys His Gly Thr Ala Glu Leu Lys Cys Phe Gln
                565                 570                 575

Lys Ser Asn Leu Ala Arg Val Val Trp Lys Phe Gln Asn Gly Glu Leu
            580                 585                 590

Lys Ala Val Ser Pro Lys Tyr Gly Phe Val Gly Arg Lys His Leu Leu
        595                 600                 605

Ile Phe Asn Leu Ser Asp Gly Asp Ser Gly Val Tyr Gln Cys Leu Ser
    610                 615                 620

Glu Glu Arg Val Arg Asn Lys Thr Val Ser Gln Leu Leu Ala Lys His
625                 630                 635                 640

Ile Leu Glu Val Lys Met Val Ala Arg Ile Pro Pro Ser Pro Thr Ser
                645                 650                 655

Gln Thr Ala Gln Thr Glu Gly Ser Arg Ile Thr Ser Lys Met Pro Val
                660                 665                 670

Ala Ser Thr Gln Gly Ser Ser Pro Pro Thr Pro Ala Leu Trp Ala Thr
            675                 680                 685

Ser Pro Arg Ala Ala Thr Leu Pro Pro Lys Ser Ser Ser Thr Gly Thr
        690                 695                 700

Ser Cys Glu Pro Lys Met Val Ile Asn Thr Val Pro Gln Leu His Ser
705                 710                 715                 720

Glu Lys Thr Val Tyr Leu Lys Ser Ser Asp Asn Arg Leu Leu Met Ser
                725                 730                 735

Leu Leu Leu Phe Leu Phe Val Leu Phe Leu Cys Leu Phe Ser Tyr Asn
            740                 745                 750

Cys Tyr Lys Gly Tyr Leu Pro Gly Gln Cys Leu Lys Phe Arg Ser Ala
        755                 760                 765

Leu Leu Leu Ala Lys Lys Pro Lys Ser Glu Phe Ser Asp Leu Glu
    770                 775                 780

Gln Ser Val Lys Glu Thr Leu Val Glu Pro Gly Ser Phe Ser Gln Gln
785                 790                 795                 800

Asn Gly Asp Gln Pro Lys Pro Ala Leu Asp Thr Gly Tyr Glu Thr Glu
                805                 810                 815

Gln Asp Thr Ile Thr Ser Lys Val Pro Thr Asp Arg Glu Asp Ser Gln
                820                 825                 830

Arg Ile Asp Glu Leu Ser Ala Arg Asp Lys Pro Phe Asp Val Lys Cys
            835                 840                 845

Glu Leu Lys Phe Ala Asp Ser Asp Ala Asp Gly Asp
850                 855                 860

Chimpanzee Sema4D cDNA nucleic acid sequence (GenBank Acc.
Num. XM_001141771.3; SEQ ID NO: 9):
atgaggatgt gcacccccat taggggctg ctcatggccc ttgcagtgat gtttgggaca    60
gcgatggcat ttgcacccat accccggatc acctgggagc acagagaggt gcgcctggtg   120
cagtttcatg agccagacat ctacaactac tcagccttgc tgctgagcga ggacaaggac   180
accttgtaca taggtgcccg ggaggcggcc ttcgctgtga cgcactcaa catctccgag   240 aagcagcatg aggtgtatcg gaaggtctca gaagacaaaa agcaaaatg tgcagaaaag   300 gggaaatcaa aacagacaga gtgcctcaac tacatccggg tgctgcagcc actcagcgcc   360
acttcccttt acgtgtgtgg gaccaacgca ttccagccgg cccgtgacca cctgaactta   420
```

-continued

```
acatccttta agtttctggg gaaaaatgaa gatggcaaag gaagatgtcc ctttgaccca      480
gcacacagct acacatccgt catggttgat ggagaacttt attcggggac gtcgtataat      540
tttttgggaa gtgaacccat catctcccga aatccttccc acagtcccct gaggacagaa      600
tacgcaatcc cttggctgaa cgagcctagt ttcgtgtttg ctgatgtgat ccgaaaaagc      660
ccagacagcc ccgacggcga ggatgacagg gtccacttct tcctcacgga ggtgcctgtg      720
gagtatgagt ttgtgttcag ggtgctgatc ccacggatag caagagtatg caaggggggac     780 cagggcggcc tgaggacctt gcagaagaaa tggacctcct tcctgaaagc ccgactcatc      840
tgctcccggc cagacagcgg cttggtcttc aatgtgctgc gggatgtctt cgtgctcagg      900
tccccgggcc tgaaggtgcc tgtgttctat gcactcttca ccccacagct gaacaacgtg      960
gggctgtcgg cagtgtgcgc ctacaacctg tccacagccg aggaggtctt ctcccacggg     1020
aagtacatgc agagccaccac agtggagcag tcccacacca gtgggtgcg ctataatggc      1080 ccggtaccca agccgcggcc tggagcgtgc atcgacagcg aggcacgggc cgccaactac     1140
accagctcct tgaatttgcc agacaagacg ctgcagttcg ttaaagacca ccccttgatg     1200
gatgactcgg taaccccaat agacaacagg cccaggttaa tcaagaaaga tatgaactac     1260
acccagatcc tggtggaccg gacccaggcc ctggatggga ctgtctatga tgtcatgttt     1320
gtcagcacag accggggagc tctgcacaaa gccatcagcc tcgagcacgc tgttcacatc     1380
atcgaggaga cccagctctt ccaggacttt gagccagtcc agaccctgct gctgtcttca     1440
aagaagggca caggtttgt ctatgctggc tccaactcgg gcgtggtcca ggccccgctg      1500
gccttctgtg ggaagcacgg cacctgcgag gactgtgtgc tggcgcggga ccctactgc      1560 gcctggaacc cgcccacagc gacccgcgcg gctccgcacc agaccgagag ccccagcagg     1620
ggttcgattc aggagatgag cggcgatgct tctgtgtgcc cggataaaag taaggaagc      1680 taccggcagc atttttcaa gcacggtggc acagcggaac tgaaatgctc ccaaaaatcc      1740
aacccggccc gggtcttttg gaagttccag aatggcgtgt tgaaggccga gagcccaag     1800 tacggtctta tgggcagaaa aaacttgctc atctccaact tgtcagaagg agacagtggg     1860
gtgtaccagt gcctgtcaga ggagagggtt aagaacaaaa cggtcttcca agtggtcgcc     1920
aagcacgtcc tggaagtgaa ggtggtccca aagcccgtag tggcccccac cttgtcagtt     1980
gttcagacag aaggtagtag gattgccacc aaagtgttgg tggcatccac ccaagggtct     2040 tctccccaa ccccagccgt gcaggccacc tcctccgggg ccatcaccct tcctcccaag     2100
cctgcgccca ctggcacatc ctgcgaacca agatcgtca tcaacacggt ccccagctc      2160 cactcggaga aaaccatgta tcttaagtcc agcgacaacc gcctcctcat gtccctcttc     2220
ctcctcttct ttgttctctt cctctgcctc ttttttctaca actgctataa gggatacctg     2280
cccagacagt gcttgaaatt ccgctcggcc ctactaattg ggaagaagaa gcccaagtca     2340
gatttctgtg accgtgagca gagcctgaag gagacgttag tagagccagg gagcttctcc     2400
cagcagaatg gggagcaccc caagccagcc ctggacaccg gctatgagac cgagcaagac     2460
accatcacca gcaaagtccc cacggatagg gaggactcac agaggatcga cgacctttct     2520
gccagggaca agccctttga cgtcaagtgt gagctgaagt tcgctgactc agacgcagat     2580
ggagactga                                                             2589
```

Chimpanzee Sema4D amino acid sequence (GenBank Acc. Num. XP_001141771.2; SEQ ID NO: 10):

```
Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30
```

-continued

```
Glu His Arg Glu Val Arg Leu Val Gln Phe His Glu Pro Asp Ile Tyr
             35                  40                  45

Asn Tyr Ser Ala Leu Leu Ser Glu Asp Lys Asp Thr Leu Tyr Ile
 50                  55                  60

Gly Ala Arg Glu Ala Val Phe Ala Val Asn Ala Leu Asn Ile Ser Glu
 65                  70                  75                  80

Lys Gln His Glu Val Tyr Trp Lys Val Ser Glu Asp Lys Lys Ala Lys
                 85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
            115                 120                 125

Asn Ala Phe Gln Pro Ala Cys Asp His Leu Asn Leu Thr Ser Phe Lys
130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
210                 215                 220

Asp Gly Glu Asp Asp Arg Val Tyr Phe Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Arg Pro Asp Ser Gly Leu
        275                 280                 285

Val Phe Asn Val Leu Arg Asp Val Phe Val Leu Arg Ser Pro Gly Leu
    290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Thr Val Glu Gln Ser His
            340                 345                 350

Thr Lys Trp Val Arg Tyr Asn Gly Pro Val Pro Lys Pro Arg Pro Gly
        355                 360                 365

Ala Cys Ile Asp Ser Glu Ala Arg Ala Ala Asn Tyr Thr Ser Ser Leu
    370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Met Asn Tyr Thr Gln Ile Val Val Asp Arg Thr Gln Ala Leu Asp
            420                 425                 430

Gly Thr Val Tyr Asp Val Met Phe Val Ser Thr Asp Arg Gly Ala Leu
        435                 440                 445

His Lys Ala Ile Ser Leu Glu His Ala Val His Ile Ile Glu Glu Thr
    450                 455                 460
```

```
-continued
Gln Leu Phe Gln Asp Phe Glu Pro Val Gln Thr Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
            500                 505                 510

Val Leu Ala Arg Asp Pro Tyr Cys Ala Trp Asn Pro Thr Ala Thr
        515                 520                 525

Cys Val Ala Leu His Gln Thr Glu Ser Pro Ser Arg Gly Leu Ile Gln
530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Gly Thr Ala Glu Leu Lys Cys
                565                 570                 575

Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
        595                 600                 605

Leu Leu Ile Phe Asn Leu Ser Glu Gly Asp Ser Gly Val Tyr Gln Cys
610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Val Ala Pro
                645                 650                 655

Thr Leu Ser Val Val Gln Thr Glu Gly Ser Arg Ile Ala Thr Lys Val
            660                 665                 670

Leu Val Ala Ser Thr Gln Gly Ser Ser Pro Pro Thr Pro Ala Val Gln
        675                 680                 685

Ala Thr Ser Ser Gly Ala Ile Thr Leu Pro Pro Lys Pro Ala Pro Thr
        690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Leu Phe Val Leu Phe Leu Cys Leu Phe Phe
            740                 745                 750

Tyr Asn Cys Tyr Lys Gly Tyr Leu Pro Arg Gln Cys Leu Lys Phe Arg
        755                 760                 765

Ser Ala Leu Leu Ile Gly Lys Lys Pro Lys Ser Asp Phe Cys Asp
770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
                805                 810                 815

Thr Glu Gln Asp Thr Ile Thr Ser Lys Val Pro Thr Asp Arg Glu Asp
            820                 825                 830

Ser Gln Arg Ile Asp Asp Leu Ser Ala Arg Asp Lys Pro Phe Asp Val
        835                 840                 845

Lys Cys Glu Leu Lys Phe Ala Asp Ser Asp Ala Asp Gly Asp
850                 855                 860

Human PlexinB1 cDNA nucleic acid sequence (GenBank Acc. Num.
NM_002673.4; SEQ ID NO: 11):
atgcctgctc tgggcccagc tcttctccag gctctctggg ccgggtgggt cctcacccte    60 cagccccttc caccaactgc attcactccc aatggcacgt atctgcagca cctggcaagg   120
```

-continued

```
gaccccacct caggcaccct ctacctgggg gctaccaact tcctgttcca gctgagccct    180
gggctgcagc tggaggccac agtgtccacc ggccctgtgc tagacagcag ggactgcctg    240
ccacctgtga tgcctgatga gtgccccag gcccagccta ccaacaaccc gaatcagctg    300
ctcctggtga gcccaggggc cctggtggta tgcgggagcg tgcaccaggg ggtctgtgaa    360
cagcggcgcc tggggcagct cgagcagctg ctgctgcggc cagagcggcc tggggacaca    420
caatatgtgg ctgccaatga tcctgcggtc agcacggtgg ggctggtagc ccagggcttg    480 gcagggagc ccctcctgtt tgtggggcga ggatacacca gcagggtgt gggggtggc    540 attccaccca tcacaacccg ggccctgtgg ccgcccgacc cccaagctgc cttctcctat    600
gaggagacag ccaagctggc agtgggccgc ctctccgagt acagccacca cttcgtgagt    660
gcctttgcac gtggggccag cgcctacttc ctgttcctgc ggcgggacct gcaggctcag    720
tctagagctt ttcgtgccta tgtatctcga gtgtgtctcc gggaccagca ctactactcc    780
tatgtggagt tgcctctggc ctgcgaaggt ggccgctacg ggctgatcca ggctgcagct    840
gtggccacgt ccagggaggt ggcgcatggg gaggtgctct ttgcagcttt ctcctcggct    900 gcaccccca ctgtgggccg gcccccatcg gcggctgctg gggcatctgg agcctctgcc    960
ctctgtgcct tcccctgga tgaggtggac cggcttgcta atcgcacgcg agatgcctgc    1020
tacacccggg agggtcgtgc tgaggatggg accgaggtgg cctacatcga gtatgatgtc    1080
aattctgact gtgcacagct gccagtgac acctgatg cttatccctg tggctcagac    1140
cacacgccca gcccatggc cagccgggtc ccgctggaag ccacaccaat tctggagtgg    1200
ccagggattc agctaacagc tgtggcagtc accatgaag atggacacac catcgctttc    1260
ctgggtgata gtcaagggca gctgcacagg gtctacttgg gcccagggag cgatggccac    1320
ccatactcca cacagagcat ccagcagggg tctgcagtga gcagagacct cacctttgat    1380
gggacctttg agcacctgta tgtcatgacc cagagcacac ttctgaaggt tcctgtggct    1440
tcctgtgctc agcacctgga ctgtgcatct tgccttgctc acaggacccc atactgtggg    1500
tggtgcgtgc tccttggcag gtgcagtcgc cgttctgagt gctcgagggg ccagggccca    1560
gagcagtggc tatggagctt ccagcctgag ctggctgtc tgcaagtggc agccatgagt    1620
cctgccaaca tcagccgaga ggagacgagg gaggttttcc tatcagtgcc agacctgcca    1680 ccctgtggc caggggagtc atattcctgc cactttgggg aacatcagag tcctgccctg    1740
ctgactggtt ctggtgtgat gtgcccctcc ccagacccta gtgaggcccc agtgctgccg    1800
agaggagccg actacgtatc cgtgagcgtg gagctcagat ttggcgctgt tgtgatcgcc    1860
aaaacttccc tctctttcta tgactgtgtg gcggtcactg aactccgccc atctgcgcag    1920
tgccaggcct gtgtgagcag ccgctggggg tgtaactggt gtgtctggca gcacctgtgc    1980
acccacaagg cctcgtgtga tgctgggccc atggttgcaa gccatcagag cccgcttgtc    2040
tccccagacc ctcctgcaag aggtggaccc agccctccc cacccacagc ccccaaagcc    2100
ctggccaccc ctgctcctga caccttccc gtggagcctg ggctccctc cacagccaca    2160 gcttcggaca tctcacctgg ggctagtcct tccctgctca gccctggggc gccatgggca    2220
ggttctggct ccatatcttc ccctggctcc acagggtcgc ctctccatga ggagccctcc    2280
cctcccagcc cccaaaatgg acctggaacc gctgtccctg ccccactga cttcagaccc    2340 tcagccacac ctgaggacct cttggcctcc ccgctgtcac cgtcagaggt agcagcagtg    2400 cccccctgcag acctggcccc cgaggctctt catcccacag tgccctgga cctgcccct    2460 gccactgttc ctgccaccac tttcccaggg gccatgggct ccgtgaagcc cgccctggac    2520
tggctcacga gagaaggcgg cgagctgccc gaggcggacg agtggacggg gggtgacgca    2580
```

```
cccgccttct ccacttccac cctcctctca ggtgatggag actcagcaga gcttgagggc   2640
cctcccgccc ccctcatcct cccgtccagc ctcgactacc agtatgacac ccccgggctc   2700
tgggagctgg aagaggcgac cttgggggca agctcctgcc cctgtgtgga gagcgttcag   2760
ggctccacgt tgatgccggt ccatgtggag cggaaatcc ggctgctagg caggaacctg    2820
caccttttcc aggatggccc aggagacaat gagtgtgtga tggagctgga gggcctcgag   2880
gtggtggttg aggcccgggt cgagtgtgag ccacctccag atacccagtg ccatgtcacc   2940
tgccagcagc accagctcag ctatgaggct ctgcagccgg agctccgtgt ggggctgttt   3000
ctgcgtcggg ccggccgtct gcgtgtgac agtgctgagg ggctgcatgt ggtactgtat    3060
gactgttccg tgggacatgg agactgcagc cgctgccaaa ctgccatgcc ccagtatggc   3120
tgtgtgtggt gtgaggggga gcgtccacgt tgtgtgaccc gggaggcctg tggtgaggct   3180
gaggctgtgg ccacccagtg cccagcgccc ctcatccact cggtggagcc actgactggg   3240
cctgtagacg gaggcacccg tgtcaccatc aggggctcca acctgggcca gcatgtgcag   3300
gatgtgctgg gcatggtcac ggtggctgga gtgccctgtg ctgtggatgc ccaggagtac   3360
gaggtctcca gcagcctcgt gtgcatcacc ggggccagtg gggaggaggt ggccggcgcc   3420
acagcggtgg aggtgccggg aagaggacgt ggtgtctcag aacacgactt tgcctaccag   3480
gatccgaagg tccattccat cttcccggcc cgcggcccca gagctggggg cacccgtctc   3540
accctgaatg gctccaagct cctgactggg cggctggagg acatccgagt ggtggttgga   3600
gaccagcctt gtcacttgct gccggagcag cagtcagaac aactgcggtg tgagaccagc   3660
ccacgcccca cgcctgccac gctccctgtg gctgtgtggg ttggggccac ggagcggagg   3720
cttcaacgcg gacagttcaa gtataccttg accccaaca tcacctctgc tggccccacc    3780
aagagcttcc tcagtggagg acgtgagata tgcgtccgtg ccagaaacct ggacgcggta   3840
cagacgccaa gaatccgggt gaccgtggtc tcgagaatgc tgcagcccag ccaggggctt   3900
ggacggaggc gtcgcgtggt cccggagacg gcatgttccc ttggaccctc ctgcagtagc   3960
cagcaatttg aggagccgtg ccatgtcaac tcctcccagc tcatcacgtg ccgcacacct   4020
gccctcccag gcctgcctga ggaccctgg gtccgggtgg aatttatcct tgacaacctg    4080
gcctctgact ttgcaacact gaaccccaca cctccctccc atgaggccga ccccaccctg   4140
cagccactca accctgagga ccccaccatg ccattccggc acaagcctgg gagtgtgttc   4200
tccgtggagg gggagaacct ggaccttgca atgtccaagg aggaggtggt ggctatgata   4260
ggggatggcc cctgtgtggt gaagacgctg acgcggcacc acctgtactg cgagcccccc   4320
gtggagcagc ccctgccacg gcaccatgcc ctccgagagg cacctgactc tttgcctgag   4380
ttcacggtgc agatgggaa cttgcgcttc tccctgggtc acgtgcagta tgacggcgag    4440
agccctgggg cttctcctgt ggcagcccag gtgggcttgg gggtgggcac ctctcttctg   4500
gctctgggtg tcatcatcat tgtcctcatg cacaggagga agagcaagca ggccctgagg   4560
gactataaga aggttcagat ccagctggag aatctggaga gcagtgtgcg ggaccgctgc   4620
aagaaggaat tcacagacct catgactgag atgaccgatc tcaccagtga cctcctgggc   4680
agcggcatcc cctccctcga ctacaaggtg tatgcggaga ggatcttctt ccctgggcac   4740
cgcgagtcgc ccttgcaccg ggacctgggt gtgcctgaga gcagacggcc cactgtggag   4800
caagggctgg ggcagctctc taacctgctc aacagcaagc tcttcctcac caagttcatc   4860
cacacgctgg agagccagcg cacccttttca gctcgggacc gtgcctacgt ggcatctctg   4920
ctcaccgtgg cactgcatgg gaagcttgag tatttcactg acatcctccg cactctgctc   4980
agtgacctgg ttgcccagta tgtggccaag aaccccaagc tgatgctgcg caggacagag   5040
```

-continued

```
actgtggtgg agaagctgct caccaactgg atgtccatct gtctgtatac cttcgtgagg    5100
gactccgtag gggagcctct gtacatgctc tttcgaggga ttaagcacca agtggataag    5160
gggccagtgg acagtgtgac aggcaaggcc aaacacacct tgaacgacaa ccgcccgctc    5220 agagaggat  tggagtaccg tcccctgacc ttgaatgcac tattggctgt ggggcctggg    5280
gcaggagagg cccagggcgt gcccgtgaag gtcctagact gtgacaccat ctcccaggca    5340
aaggagaaga tgctggacca gctttataaa ggagtgcctc tcacccagcg gccagacccc    5400
cgcacccttg atgttgagtg gcggtctggg gtggccgggc acctcattct ttctgacgag    5460
gatgccactt ctgaggccca gggtctgtgg aggcgcctga acacaccgca gcattacaag    5520
gtcccagatg gagcaactgt ggccctcgtc cctgcctca  ccaagcatgt gctccgggaa    5580
aaccaggatt atgtccctgg agagcggacc ccaatgctgg aggatgtaga tgaggggggc    5640
acccggccct ggcacctggt gaagccaagt gatgagccgg agccgcccag gcctcggagg    5700
ggcagccttc ggggcgggga gcgtgagcgc gccaaggcca tccctgagat ctacctgacc    5760
cgcctgctgt ccatgaaggg caccctgcag aagttcgtgg atgacctgtt ccaggtgatt    5820
ctcagcacca gccgccccgt gccgctcgct gtgaagtact tctttgacct gctggatgag    5880
caggcccagc agcatggcat ctccgaccag gacaccatcc acatctggaa gaccaacagc    5940
ttgcctctga ggttctggat caatataata aaaaacccgc agtttgtgtt cgacgtgcaa    6000
acatctgata catggatgc  ggtgctcctt gtcattgcac agaccttcat ggacgcctgc    6060
accctggccg accacaagct gggccgggac tccccgatca caaacttcct gtatgcacgg    6120
gacattcccc ggtacaagcg gatggtggaa aggtactatg cagacatcag acagactgtc    6180
ccagccagcg accaagagat gaactctgtc ctggctgaac tgtcctggaa ctactccgga    6240
gacctcgggg gcgagtggcc cctgcatgaa ctctacaagt acatcaacaa gtactatgac    6300
cagatcatca ctgccctgga ggaggatggc acggcccaga gatgcagct  gggctatcgg    6360 ctccagcaga ttgcagctgc tgtgaaaaac aaggtcacag atctatag                6408
```

Human PlexinB1 amino acid sequence (GenBank Acc. Num.
NP_002664.2; SEQ ID NO: 12):

```
Met Pro Ala Leu Gly Pro Ala Leu Leu Gln Ala Leu Trp Ala Gly Trp
1               5                   10                  15

Val Leu Thr Leu Gln Pro Leu Pro Thr Ala Phe Thr Pro Asn Gly
            20                  25                  30

Thr Tyr Leu Gln His Leu Ala Arg Asp Pro Thr Ser Gly Thr Leu Tyr
        35                  40                  45

Leu Gly Ala Thr Asn Phe Leu Phe Gln Leu Ser Pro Gly Leu Gln Leu
    50                  55                  60

Glu Ala Thr Val Ser Thr Gly Pro Val Leu Asp Ser Arg Asp Cys Leu
65                  70                  75                  80

Pro Pro Val Met Pro Asp Glu Cys Pro Gln Ala Gln Pro Thr Asn Asn
                85                  90                  95

Pro Asn Gln Leu Leu Leu Val Ser Pro Gly Ala Leu Val Val Cys Gly
            100                 105                 110

Ser Val His Gln Gly Val Cys Glu Gln Arg Arg Leu Gly Gln Leu Glu
        115                 120                 125

Gln Leu Leu Leu Arg Pro Glu Arg Pro Gly Asp Thr Gln Tyr Val Ala
    130                 135                 140

Ala Asn Asp Pro Ala Val Ser Thr Val Gly Leu Val Ala Gln Gly Leu
145                 150                 155                 160

Ala Gly Glu Pro Leu Leu Phe Val Gly Arg Gly Tyr Thr Ser Arg Gly
                165                 170                 175
```

```
Val Gly Gly Gly Ile Pro Pro Ile Thr Thr Arg Ala Leu Trp Pro Pro
            180                 185                 190

Asp Pro Gln Ala Ala Phe Ser Tyr Glu Glu Thr Ala Lys Leu Ala Val
        195                 200                 205

Gly Arg Leu Ser Glu Tyr Ser His His Phe Val Ser Ala Phe Ala Arg
        210                 215                 220

Gly Ala Ser Ala Tyr Phe Leu Phe Leu Arg Arg Asp Leu Gln Ala Gln
225                 230                 235                 240

Ser Arg Ala Phe Arg Ala Tyr Val Ser Arg Val Cys Leu Arg Asp Gln
                245                 250                 255

His Tyr Tyr Ser Tyr Val Glu Leu Pro Leu Ala Cys Glu Gly Gly Arg
                260                 265                 270

Tyr Gly Leu Ile Gln Ala Ala Val Ala Thr Ser Arg Glu Val Ala
                275                 280                 285

His Gly Glu Val Leu Phe Ala Ala Phe Ser Ser Ala Ala Pro Pro Thr
        290                 295                 300

Val Gly Arg Pro Pro Ser Ala Ala Gly Ala Ser Gly Ala Ser Ala
305                 310                 315                 320

Leu Cys Ala Phe Pro Leu Asp Glu Val Asp Arg Leu Ala Asn Arg Thr
                325                 330                 335

Arg Asp Ala Cys Tyr Thr Arg Glu Gly Arg Ala Glu Asp Gly Thr Glu
                340                 345                 350

Val Ala Tyr Ile Glu Tyr Asp Val Asn Ser Asp Cys Ala Gln Leu Pro
                355                 360                 365

Val Asp Thr Leu Asp Ala Tyr Pro Cys Gly Ser Asp His Thr Pro Ser
        370                 375                 380

Pro Met Ala Ser Arg Val Pro Leu Glu Ala Thr Pro Ile Leu Glu Trp
385                 390                 395                 400

Pro Gly Ile Gln Leu Thr Ala Val Ala Val Thr Met Glu Asp Gly His
                405                 410                 415

Thr Ile Ala Phe Leu Gly Asp Ser Gln Gly Gln Leu His Arg Val Tyr
                420                 425                 430

Leu Gly Pro Gly Ser Asp Gly His Pro Tyr Ser Thr Gln Ser Ile Gln
        435                 440                 445

Gln Gly Ser Ala Val Ser Arg Asp Leu Thr Phe Asp Gly Thr Phe Glu
        450                 455                 460

His Leu Tyr Val Met Thr Gln Ser Thr Leu Leu Lys Val Pro Val Ala
465                 470                 475                 480

Ser Cys Ala Gln His Leu Asp Cys Ala Ser Cys Leu Ala His Arg Asp
                485                 490                 495

Pro Tyr Cys Gly Trp Cys Val Leu Leu Gly Arg Cys Ser Arg Arg Ser
                500                 505                 510

Glu Cys Ser Arg Gly Gln Gly Pro Glu Gln Trp Leu Trp Ser Phe Gln
        515                 520                 525

Pro Glu Leu Gly Cys Leu Gln Val Ala Ala Met Ser Pro Ala Asn Ile
        530                 535                 540

Ser Arg Glu Glu Thr Arg Glu Val Phe Leu Ser Val Pro Asp Leu Pro
545                 550                 555                 560

Pro Leu Trp Pro Gly Glu Ser Tyr Ser Cys His Phe Gly Glu His Gln
                565                 570                 575

Ser Pro Ala Leu Leu Thr Gly Ser Gly Val Met Cys Pro Ser Pro Asp
                580                 585                 590

Pro Ser Glu Ala Pro Val Leu Pro Arg Gly Ala Asp Tyr Val Ser Val
                595                 600                 605
```

-continued

```
Ser Val Glu Leu Arg Phe Gly Ala Val Val Ile Ala Lys Thr Ser Leu
610                 615                 620
Ser Phe Tyr Asp Cys Val Ala Val Thr Glu Leu Arg Pro Ser Ala Gln
625                 630                 635                 640
Cys Gln Ala Cys Val Ser Ser Arg Trp Gly Cys Asn Trp Cys Val Trp
            645                 650                 655
Gln His Leu Cys Thr His Lys Ala Ser Cys Asp Ala Gly Pro Met Val
            660                 665                 670
Ala Ser His Gln Ser Pro Leu Val Ser Pro Asp Pro Ala Arg Gly
        675                 680                 685
Gly Pro Ser Pro Ser Pro Thr Ala Pro Lys Ala Leu Ala Thr Pro
690                 695                 700
Ala Pro Asp Thr Leu Pro Val Glu Pro Gly Ala Pro Ser Thr Ala Thr
705                 710                 715                 720
Ala Ser Asp Ile Ser Pro Gly Ala Ser Pro Ser Leu Leu Ser Pro Trp
            725                 730                 735
Gly Pro Trp Ala Gly Ser Gly Ser Ile Ser Ser Pro Gly Ser Thr Gly
            740                 745                 750
Ser Pro Leu His Glu Glu Pro Ser Pro Ser Pro Gln Asn Gly Pro
        755                 760                 765
Gly Thr Ala Val Pro Ala Pro Thr Asp Phe Arg Pro Ser Ala Thr Pro
770                 775                 780
Glu Asp Leu Leu Ala Ser Pro Leu Ser Pro Ser Glu Val Ala Ala Val
785                 790                 795                 800
Pro Pro Ala Asp Pro Gly Pro Glu Ala Leu His Pro Thr Val Pro Leu
            805                 810                 815
Asp Leu Pro Pro Ala Thr Val Pro Ala Thr Thr Phe Pro Gly Ala Met
            820                 825                 830
Gly Ser Val Lys Pro Ala Leu Asp Trp Leu Thr Arg Glu Gly Gly Glu
        835                 840                 845
Leu Pro Glu Ala Asp Glu Trp Thr Gly Gly Asp Ala Pro Ala Phe Ser
        850                 855                 860
Thr Ser Thr Leu Leu Ser Gly Asp Gly Asp Ser Ala Glu Leu Glu Gly
865                 870                 875                 880
Pro Pro Ala Pro Leu Ile Leu Pro Ser Ser Leu Asp Tyr Gln Tyr Asp
            885                 890                 895
Thr Pro Gly Leu Trp Glu Leu Glu Glu Ala Thr Leu Gly Ala Ser Ser
            900                 905                 910
Cys Pro Cys Val Glu Ser Val Gln Gly Ser Thr Leu Met Pro Val His
        915                 920                 925
Val Glu Arg Glu Ile Arg Leu Leu Gly Arg Asn Leu His Leu Phe Gln
930                 935                 940
Asp Gly Pro Gly Asp Asn Glu Cys Val Met Glu Leu Glu Gly Leu Glu
945                 950                 955                 960
Val Val Val Glu Ala Arg Val Glu Cys Glu Pro Pro Asp Thr Gln
            965                 970                 975
Cys His Val Thr Cys Gln Gln His Gln Leu Ser Tyr Glu Ala Leu Gln
        980                 985                 990
Pro Glu Leu Arg Val Gly Leu Phe  Leu Arg Arg Ala Gly  Arg Leu Arg
        995                 1000                 1005
Val Asp  Ser Ala Glu Gly Leu  His Val Val Leu Tyr  Asp Cys Ser
        1010                 1015                 1020
Val Gly  His Gly Asp Cys Ser  Arg Cys Gln Thr Ala  Met Pro Gln
        1025                 1030                 1035
```

```
Tyr Gly Cys Val Trp Cys Glu Gly Glu Arg Pro Arg Cys Val Thr
    1040            1045                1050
Arg Glu Ala Cys Gly Glu Ala Glu Ala Val Ala Thr Gln Cys Pro
    1055            1060                1065
Ala Pro Leu Ile His Ser Val Glu Pro Leu Thr Gly Pro Val Asp
    1070            1075                1080
Gly Gly Thr Arg Val Thr Ile Arg Gly Ser Asn Leu Gly Gln His
    1085            1090                1095
Val Gln Asp Val Leu Gly Met Val Thr Val Ala Gly Val Pro Cys
    1100            1105                1110
Ala Val Asp Ala Gln Glu Tyr Glu Val Ser Ser Ser Leu Val Cys
    1115            1120                1125
Ile Thr Gly Ala Ser Gly Glu Glu Val Ala Gly Thr Ala Val
    1130            1135                1140
Glu Val Pro Gly Arg Gly Arg Gly Val Ser Glu His Asp Phe Ala
    1145            1150                1155
Tyr Gln Asp Pro Lys Val His Ser Ile Phe Pro Ala Arg Gly Pro
    1160            1165                1170
Arg Ala Gly Gly Thr Arg Leu Thr Leu Asn Gly Ser Lys Leu Leu
    1175            1180                1185
Thr Gly Arg Leu Glu Asp Ile Arg Val Val Gly Asp Gln Pro
    1190            1195                1200
Cys His Leu Leu Pro Glu Gln Gln Ser Glu Gln Leu Arg Cys Glu
    1205            1210                1215
Thr Ser Pro Arg Pro Thr Pro Ala Thr Leu Pro Val Ala Val Trp
    1220            1225                1230
Phe Gly Ala Thr Glu Arg Arg Leu Gln Arg Gly Gln Phe Lys Tyr
    1235            1240                1245
Thr Leu Asp Pro Asn Ile Thr Ser Ala Gly Pro Thr Lys Ser Phe
    1250            1255                1260
Leu Ser Gly Gly Arg Glu Ile Cys Val Arg Gly Gln Asn Leu Asp
    1265            1270                1275
Val Val Gln Thr Pro Arg Ile Arg Val Thr Val Val Ser Arg Met
    1280            1285                1290
Leu Gln Pro Ser Gln Gly Leu Gly Arg Arg Arg Val Val Pro
    1295            1300                1305
Glu Thr Ala Cys Ser Leu Gly Pro Ser Cys Ser Ser Gln Gln Phe
    1310            1315                1320
Glu Glu Pro Cys His Val Asn Ser Ser Gln Leu Ile Thr Cys Arg
    1325            1330                1335
Thr Pro Ala Leu Pro Gly Leu Pro Glu Asp Pro Trp Val Arg Val
    1340            1345                1350
Glu Phe Ile Leu Asp Asn Leu Val Phe Asp Phe Ala Thr Leu Asn
    1355            1360                1365
Pro Thr Pro Phe Ser Tyr Glu Ala Asp Pro Thr Leu Gln Pro Leu
    1370            1375                1380
Asn Pro Glu Asp Pro Thr Met Pro Phe Arg His Lys Pro Gly Ser
    1385            1390                1395
Val Phe Ser Val Glu Gly Glu Asn Leu Asp Leu Ala Met Ser Lys
    1400            1405                1410
Glu Glu Val Val Ala Met Ile Gly Asp Gly Pro Cys Val Val Lys
    1415            1420                1425
Thr Leu Thr Arg His His Leu Tyr Cys Glu Pro Pro Val Glu Gln
    1430            1435                1440
```

```
Pro Leu Pro Arg His His Ala Leu Arg Glu Ala Pro Asp Ser Leu
1445                1450                1455

Pro Glu Phe Thr Val Gln Met Gly Asn Leu Arg Phe Ser Leu Gly
1460                1465                1470

His Val Gln Tyr Asp Gly Glu Ser Pro Gly Ala Phe Pro Val Ala
1475                1480                1485

Ala Gln Val Gly Leu Gly Val Gly Thr Ser Leu Leu Ala Leu Gly
1490                1495                1500

Val Ile Ile Ile Val Leu Met Tyr Arg Arg Lys Ser Lys Gln Ala
1505                1510                1515

Leu Arg Asp Tyr Lys Lys Val Gln Ile Gln Leu Glu Asn Leu Glu
1520                1525                1530

Ser Ser Val Arg Asp Arg Cys Lys Lys Glu Phe Thr Asp Leu Met
1535                1540                1545

Thr Glu Met Thr Asp Leu Thr Ser Asp Leu Leu Gly Ser Gly Ile
1550                1555                1560

Pro Phe Leu Asp Tyr Lys Val Tyr Ala Glu Arg Ile Phe Phe Pro
1565                1570                1575

Gly His Arg Glu Ser Pro Leu His Arg Asp Leu Gly Val Pro Glu
1580                1585                1590

Ser Arg Arg Pro Thr Val Glu Gln Gly Leu Gly Gln Leu Ser Asn
1595                1600                1605

Leu Leu Asn Ser Lys Leu Phe Leu Thr Lys Phe Ile His Thr Leu
1610                1615                1620

Glu Ser Gln Arg Thr Phe Ser Ala Arg Asp Arg Ala Tyr Val Ala
1625                1630                1635

Ser Leu Leu Thr Val Ala Leu His Gly Lys Leu Glu Tyr Phe Thr
1640                1645                1650

Asp Ile Leu Arg Thr Leu Leu Ser Asp Leu Val Ala Gln Tyr Val
1655                1660                1665

Ala Lys Asn Pro Lys Leu Met Leu Arg Arg Thr Glu Thr Val Val
1670                1675                1680

Glu Lys Leu Leu Thr Asn Trp Met Ser Ile Cys Leu Tyr Thr Phe
1685                1690                1695

Val Arg Asp Ser Val Gly Glu Pro Leu Tyr Met Leu Phe Arg Gly
1700                1705                1710

Ile Lys His Gln Val Asp Lys Gly Pro Val Asp Ser Val Thr Gly
1715                1720                1725

Lys Ala Lys Tyr Thr Leu Asn Asp Asn Arg Leu Leu Arg Glu Asp
1730                1735                1740

Val Glu Tyr Arg Pro Leu Thr Leu Asn Ala Leu Leu Ala Val Gly
1745                1750                1755

Pro Gly Ala Gly Glu Ala Gln Gly Val Pro Val Lys Val Leu Asp
1760                1765                1770

Cys Asp Thr Ile Ser Gln Ala Lys Glu Lys Met Leu Asp Gln Leu
1775                1780                1785

Tyr Lys Gly Val Pro Leu Thr Gln Arg Pro Asp Pro Arg Thr Leu
1790                1795                1800

Asp Val Glu Trp Arg Ser Gly Val Ala Gly His Leu Ile Leu Ser
1805                1810                1815

Asp Glu Asp Val Thr Ser Glu Val Gln Gly Leu Trp Arg Arg Leu
1820                1825                1830

Asn Thr Leu Gln His Tyr Lys Val Pro Asp Gly Ala Thr Val Ala
1835                1840                1845
```

-continued

```
Leu Val Pro Cys Leu Thr Lys His Val Leu Arg Glu Asn Gln Asp
1850                1855                1860
Tyr Val Pro Gly Glu Arg Thr Pro Met Leu Glu Asp Val Asp Glu
    1865                1870                1875
Gly Gly Ile Arg Pro Trp His Leu Val Lys Pro Ser Asp Glu Pro
1880                1885                1890
Glu Pro Pro Arg Pro Arg Arg Gly Ser Leu Arg Gly Gly Glu Arg
    1895                1900                1905
Glu Arg Ala Lys Ala Ile Pro Glu Ile Tyr Leu Thr Arg Leu Leu
1910                1915                1920
Ser Met Lys Gly Thr Leu Gln Lys Phe Val Asp Asp Leu Phe Gln
1925                1930                1935
Val Ile Leu Ser Thr Ser Arg Pro Val Pro Leu Ala Val Lys Tyr
1940                1945                1950
Phe Phe Asp Leu Leu Asp Glu Gln Ala Gln Gln His Gly Ile Ser
1955                1960                1965
Asp Gln Asp Thr Ile His Ile Trp Lys Thr Asn Ser Leu Pro Leu
1970                1975                1980
Arg Phe Trp Ile Asn Ile Ile Lys Asn Pro Gln Phe Val Phe Asp
1985                1990                1995
Val Gln Thr Ser Asp Asn Met Asp Ala Val Leu Leu Val Ile Ala
2000                2005                2010
Gln Thr Phe Met Asp Ala Cys Thr Leu Ala Asp His Lys Leu Gly
2015                2020                2025
Arg Asp Ser Pro Ile Asn Lys Leu Leu Tyr Ala Arg Asp Ile Pro
2030                2035                2040
Arg Tyr Lys Arg Met Val Glu Arg Tyr Tyr Ala Asp Ile Arg Gln
2045                2050                2055
Thr Val Pro Ala Ser Asp Gln Glu Met Asn Ser Val Leu Ala Glu
2060                2065                2070
Leu Ser Trp Asn Tyr Ser Gly Asp Leu Gly Ala Arg Val Ala Leu
2075                2080                2085
His Glu Leu Tyr Lys Tyr Ile Asn Lys Tyr Tyr Asp Gln Ile Ile
2090                2095                2100
Thr Ala Leu Glu Glu Asp Gly Thr Ala Gln Lys Met Gln Leu Gly
2105                2110                2115
Tyr Arg Leu Gln Gln Ile Ala Ala Ala Val Glu Asn Lys Val Thr
2120                2125                2130
Asp Leu
2135

Mouse PlexinB1 amino acid sequence (GenBank Acc. Num.
NP_002664.2; SEQ ID NO: 13):
atgtctgtcc tcggcccagt tcttctccag gtgttctggg ccgggtgtgt cgtcaccctg    60
cggtccctc tgccagctgc tttcactgcc aatggcacac atctacaaca cttggcaagg    120
gaccccacca caggtaccct ctatgtaggg gccaccaact tcctgttcca gttgagccct    180
gggctgcagc tggaagccgt ggtgtccacg ggccctgtga atgacagccg ggattgcctg    240
ccacctgtga tacctgatga atgtccccaa gcccagccta ctaacaaccc taaccagctg    300
ctcctggtga gcccagaggc tctggtggtg tgtgggagcg tacaccaggg catctgtgag    360
ctacggagcc tgggacagat caggcagctg ctgctacggc cagagcgacc tgggacacc    420
cagtatgtgg ctgcaaatga ccctgcagtc agtacagtgg ggctggtggc ccagggattg    480
gtaggggagc cctcctgtt tgtggggcgg gggtacacca gcaggggtgt aggtggtggg    540
attcctccca ttacaacccg agccctgcga ccaccggacc cccaagctgc cttctcttat    600
```

```
gaagaaacag ccaagttagc agtgggccgc ctgtccgagt acagccacca cttcgtgagt    660
gcctttgtac gcggggccag tgcatacttc ctgttcttgc ggcgagacct gaaggcccct    720
tctagagctt tccgtgccta tgtgtctcga gtgtgccttc aggaccagca ctactactct    780
tatgtggaat tgcccctggc ctgccagggt ggtcgttacg gtcttatcca ggctgcagct    840
gtagccacgt ccaaggaggt ggcccgtggg gacgtactct ttgcagcttt ctcctcagtg    900
gctcctccca ctgtggattg gcccctgtca gcatctactg gggcatctgg aacctctgtg    960
ctctgtgcct tcccctgga tgaggtagac cagcttgcta attacactcg agatgcctgt   1020
tatactcggg aaggccgtgc tgagaacggg accaaggttg ctgacattgc atacgatgtc   1080
ctttccgact gtgcgcagct accagtggac accccggatg cttttccatg tggctctgac   1140
cacacaccca gtcccatggt cagctgtgtc cctttggaag ccacgccaat tctgagcta    1200 ccaggggttc agctaacagc tgtggctgtc accatggagg atggacacac tattgctttc   1260
ctgggtgaca gtcaaggaca gttgcatagg gtctacttag ccctggaag aagtgctgcc    1320 ccatattcta aacagagcat ccagccgggg tctcctgtga acagagatct tacctttgat   1380
ggtacctttg agcatctcta tgtagcaact cagactactc ttgtgaaggt tcctgtggct   1440
ccttgtgctc agcatctgga ctgtgactct tgccttgctc acagggaccc ttattgcgga   1500
tggtgtgtgc tcctgggcag gtgtagtcgc cggtcggagt gctcaaggga ccagggccca   1560
gagcagtggc tgtggagctt ccagccggaa ctggctgtc ttcgagtggt ggccgtgagc    1620
cctgccaata tcagtcggga agagaggagg gaggttttct tgtcagtgcc aggcctgcca   1680
tctctctggc caggggagtc atatttctgc tactttggag accaacagag tcctgctcta   1740
ctgaccagtt ctggtgtgat gtgtccctcc ccagacccca gtgaggctcc agtgctgcag   1800
agaggagccg accatatctc tgtgaacgtg gagctcaggt ttggtgccgt ggtgatcgcc   1860
agcacctccc tctccttcta tgactgcgtg gcagttactg cgtcttcccc atctgcaccg   1920
tgccgggcct gtgtgagcag ccgctggggc tgtaactggt gtgtgtggca gcagctgtgc   1980
acacacaagg cctcgtgtga cgctgggcct atggtggcaa gccaacagag cccactcctt   2040
cccctaatcc ctcctgcaag ggatgaactc accccttccc cacccacagt ccccaaacc    2100 acggtcactc ctaccccccaa cagcttccca atagagccta gggctcctc cacagcctca   2160 gatgtcctac ctggggccaa gccttcccgg ctcagcctct ggggcccatg gcaggtcct    2220 ggccccatac tttcccctac ttccacagag tcacctcttc atgagaagcc ccttcctcct   2280 gacccccta ccatacctgg aaccactgtc cctgccccca ctggcttggg accatcgacc    2340
acacctgagg acctcttggc ctcctaccca ttcccctcag atgcagctgc agtgtcccct   2400
gcagagcctg gcctgaggc tctgccttcc atggtggctc tggaccagcc ccctggcact   2460
gttccagaca ctactttccc aggggcccct ggctccatga gcccgttct ggattggctc    2520 accaaaggag gcggcgagct gcccgaggcg gatgagtgga tgggggtga cacgcccgcc    2580 ttctccactt ccacactcct ctcaggtgat ggagactcag cagagcacga gggccctcct   2640
gcccccctca tcctcctgtc cagcctcgac taccagtacg acaccccccgg gctctgggag   2700 ctgggagagg tgaatcagag ggtgagctcc tgccctgtg tggagaccgt ccagggctcc    2760
ttgctgatac cggtccatgt ggaacgcgaa gtccagcttc gaggcaggaa cctgtggctt   2820
ttccaggatg gcccgaggag cagcgagtgt gtgctggagc tagggagtcg ggaggtggct   2880
gtggaggctc aggtggagtg tgcgccgcct ccagatgtct ggtgccacat caagtgccag   2940
cagcatcagt tcagctatga agctttgaag ccagaactgc aggtggggct gttcctgcgt   3000
tgggcaggcg gtctgcgcgt ggacagtgcc gatgggctgc atgtggtgtt gtatgactgc   3060
```

-continued

```
tctgtgggac atgggactg cagccgctgc caaactgcca tgcctcagta cgactgtgtg  3120
tggtgtgagg gggagcgtcc gcgttgtgtg gcccgggaag cctgtaatga agccgagact  3180
gtggccactc agtgccccgc acctctcatt cactcggtgg atccactgac tggacctata  3240
gatggaggca cccgtgtcac tatcaggggc tccaacctgg ccaacatgt gcaggatgtc  3300 ctggacatgg tcagagtggc cggagttccc tgcgctgtgg atgctgggga gtatgatgtc  3360
tctagtagtc ttgtgtgcat cactggagcc agcggggagg aggtgactgg cactgtggca  3420
gtggaggtgc ctggaagagg acacggtgtc tcagagttca gctttgccta tcaggatcca  3480
aaagtacact ccatcttccc agcccgtggc cctagagctg gaggtacccg ccttaccctg  3540
catggttcta agctcctgac tggacggcta gaggacatcc gtgtggtggt tggagaccag  3600
ccttgccacc tgctcctgga gcagcagtct gagcagctac actgtgagac cggcccatac  3660
cctgtgcctg ctgaacttcc agtgactgtc ttgtttgggg ccactgagcg gaggcttcag  3720
cacggccaat tcaagtatac atcagacccc aatgtcacct cagtgggccc ctccaagagc  3780
ttcttcagcg gaggacgtga gatatgggtc cgcggccagg atcttgatgt ggtacagagg  3840
ccaagaatcc gagtgaccgt ggtcccaaga cagcatggcc aggggcttgc acagaagcaa  3900
cacgtggtcc ctgagaaatt tgaggagccg tgtctcgtga actcctccca cctcctcatg  3960
tgccgcactc ccgctctccc tggcccaccc tgggactctg gggtccaggt ggagtttatc  4020
ctcgacaaca tggtctttga ctttgctgca ctgagcccca cacccttctc ctatgaggct  4080
gatcccaccc tgcgttccct gaaccccgag gatcccagca cgccgttccg gcacaagcca  4140
gggagtgtgt tctctgtgga gggggagaat ctggacctcg ccatgtctaa agaagaggtg  4200
gtggccatga taggggacgg gccctgcgtg gtaaagacac tgacccggaa ccacctgtac  4260
tgtgagcccc ctgtggagca gccccctgcca catccccatg ccctccgaga ggctccagat  4320
gctttgcctg agttcacggt acagatgggc aacctgcgct tctccttggg tcatgtgcag  4380
tacgatggcg agagccccgt ggcttttcct gtggcagccc aagtgggctt gggagtgggc  4440
acgtctctcc tggctctggg tgtcatcatc attgtcctca tatacaggag aagagcaag  4500 caggccctga gggactataa gaaagtgcag atccagctgg agaacctgga gagcagtgta  4560
cgggaccgct gtaagaagga gtttacagac ctcatgacgg agatgacgga tctcaccagt  4620
gacctccttg gcagcggtat ccccttcctt gactacaaag tgtatgctga gagggtcttc  4680
ttccctgggt accgggagtc ccccttgcac agggacctcg gtgtgcctga cagcaggcga  4740
cccaccgtgg aacagggcct ggggcagctc tccaacctgc taaacagcaa gctcttcctt  4800
accaagttca tccacacact ggagagtcag cgcaccttct ctgctcggga ccgtgcctac  4860
gtggcatctc tgctcactgt tgcacttcac gggaagcttg aatacttcac ggacatactg  4920
cggactctgc tcagtgacct ggtagctcag tatgttgcca agaaccccaa gctgatgctg  4980
cgcaggacag agaccgtggt agaaaagctg ctcaccaact ggatgtccat ctgcctctac  5040
acctttgtga gggactctgt gggagagcct ctgtatatgc tcttcagagg gattaagcat  5100
caagtggaca gggtcccgt ggacagtgtg actggcaaag ccaaatacac tctgaatgac  5160
aaccgcctgc tcagagagga tgtggagtac cgtcccttga ccttgaatgc tcttctggct  5220
gtggggcctg ggcaggaga agcccagtgt gtacctgtga agtcctgga ctgtgacacc  5280 atctcccagg ccaaggagaa gatgctagac cagctttaca agggagtgcc tcttgcccag  5340
cggcccgact cttgcaccct ggatgttgaa tggcggtctg gagtggctgg gcaccttatc  5400
ctttctgatg aggacgtcac ttccgaactc cagggtctgt ggaggcgtct gaatacactg  5460
caacattaca aggtcccaga tggagcaacg gtggcccttg tcccctgcct caccaagcat  5520
```

```
attcttaggg aaaaccagga ttatgtccct ggggaacgga ccccaatgct ggaggatgta    5580
gatgaggggg gcatccggcc ctggcacctg gtaaagccga gtgatgaacc agagcctccc    5640
aggccgagga ggggcagcct tcggggtggg gagcgtgagc gagccaaggc tatccctgag    5700
atctacctga cacgcctgct atccatgaag ggcacactgc agaagtttgt ggatgacctg    5760
ttccaggtga ttctcagcac cagccgccct gtgcctctgg ctgtgaagta cttctttgac    5820
ttgctggatg aacaagctca gcagcatggc atctctgatc aggatactat ccacatctgg    5880
aagaccaaca gcctgccgct aaggttctgg atcaacatca tcaagaaccc acagtttgtg    5940
ttcgatgtgc agacttcgga taacatggat gctgtgctcc tggtcattgc acagaccttc    6000
atggatgctt gcaccctggc cgaccacaag ctgggccggg attctcccat caacaaactt    6060
ctgtatgctc gagatattcc ccgttacaaa cagatggtgg aaaggtacta tgcagacatc    6120
agacagactg tcccggccag tgaccaagag atgaactcag tcttggcgga gctgtcccgg    6180
aactgctctg ccgaccttgg ggcgcgagtg gctctgcatg aactctacaa gtatatcaac    6240
aagtactatg accagatcat cactgccctg gaggaggatg gcactgccca gaagatgcag    6300
ctgggctacc ggctccagca gatcgccgct gctgtggaaa acaaggtcac ggatctataa    6360
```

Mouse PlexinB1 amino acid sequence (GenBank Acc. Num. NP_766363.2; SEQ ID NO: 14):

```
Met Ser Val Leu Gly Pro Val Leu Leu Gln Val Phe Trp Ala Gly Cys
1               5                   10                  15

Val Val Thr Leu Arg Ser Pro Leu Pro Ala Ala Phe Thr Ala Asn Gly
            20                  25                  30

Thr His Leu Gln His Leu Ala Arg Asp Pro Thr Thr Gly Thr Leu Tyr
        35                  40                  45

Val Gly Ala Thr Asn Phe Leu Phe Gln Leu Ser Pro Gly Leu Gln Leu
    50                  55                  60

Glu Ala Val Val Ser Thr Gly Pro Val Asn Asp Ser Arg Asp Cys Leu
65                  70                  75                  80

Pro Pro Val Ile Pro Asp Glu Cys Pro Gln Ala Gln Pro Thr Asn Asn
                85                  90                  95

Pro Asn Gln Leu Leu Leu Val Ser Pro Glu Ala Leu Val Val Cys Gly
            100                 105                 110

Ser Val His Gln Gly Ile Cys Glu Leu Arg Ser Leu Gly Gln Ile Arg
        115                 120                 125

Gln Leu Leu Leu Arg Pro Glu Arg Pro Gly Asp Thr Gln Tyr Val Ala
    130                 135                 140

Ala Asn Asp Pro Ala Val Ser Thr Val Gly Leu Val Ala Gln Gly Leu
145                 150                 155                 160

Val Gly Glu Pro Leu Leu Phe Val Gly Arg Gly Tyr Thr Ser Arg Gly
                165                 170                 175

Val Gly Gly Gly Ile Pro Pro Ile Thr Thr Arg Ala Leu Arg Pro Pro
            180                 185                 190

Asp Pro Gln Ala Ala Phe Ser Tyr Glu Glu Thr Ala Lys Leu Ala Val
        195                 200                 205

Gly Arg Leu Ser Glu Tyr Ser His His Phe Val Ser Ala Phe Val Arg
    210                 215                 220

Gly Ala Ser Ala Tyr Phe Leu Phe Leu Arg Arg Asp Leu Lys Ala Pro
225                 230                 235                 240

Ser Arg Ala Phe Arg Ala Tyr Val Ser Arg Val Cys Leu Gln Asp Gln
                245                 250                 255

His Tyr Tyr Ser Tyr Val Glu Leu Pro Leu Ala Cys Gln Gly Gly Arg
            260                 265                 270
```

-continued

```
Tyr Gly Leu Ile Gln Ala Ala Val Ala Thr Ser Lys Glu Val Ala
            275                 280                 285
Arg Gly Asp Val Leu Phe Ala Ala Phe Ser Ser Val Ala Pro Pro Thr
290                 295                 300
Val Asp Trp Pro Leu Ser Ala Ser Thr Gly Ala Ser Gly Thr Ser Val
305                 310                 315                 320
Leu Cys Ala Phe Pro Leu Asp Glu Val Asp Gln Leu Ala Asn Tyr Thr
                325                 330                 335
Arg Asp Ala Cys Tyr Thr Arg Glu Gly Arg Ala Glu Asn Gly Thr Lys
                340                 345                 350
Val Ala Asp Ile Ala Tyr Asp Val Leu Ser Asp Cys Ala Gln Leu Pro
                355                 360                 365
Val Asp Thr Pro Asp Ala Phe Pro Cys Gly Ser Asp His Thr Pro Ser
                370                 375                 380
Pro Met Val Ser Cys Val Pro Leu Glu Ala Thr Pro Ile Leu Glu Leu
385                 390                 395                 400
Pro Gly Val Gln Leu Thr Ala Val Ala Val Thr Met Glu Asp Gly His
                405                 410                 415
Thr Ile Ala Phe Leu Gly Asp Ser Gln Gly Gln Leu His Arg Val Tyr
                420                 425                 430
Leu Gly Pro Gly Arg Ser Ala Ala Pro Tyr Ser Lys Gln Ser Ile Gln
                435                 440                 445
Pro Gly Ser Pro Val Asn Arg Asp Leu Thr Phe Asp Gly Thr Phe Glu
                450                 455                 460
His Leu Tyr Val Ala Thr Gln Thr Thr Leu Val Lys Val Pro Val Ala
465                 470                 475                 480
Pro Cys Ala Gln His Leu Asp Cys Asp Ser Cys Leu Ala His Arg Asp
                485                 490                 495
Pro Tyr Cys Gly Trp Cys Val Leu Leu Gly Arg Cys Ser Arg Arg Ser
                500                 505                 510
Glu Cys Ser Arg Asp Gln Gly Pro Glu Gln Trp Leu Trp Ser Phe Gln
                515                 520                 525
Pro Glu Leu Gly Cys Leu Arg Val Val Ala Val Ser Pro Ala Asn Ile
                530                 535                 540
Ser Arg Glu Glu Arg Arg Glu Val Phe Leu Ser Val Pro Gly Leu Pro
545                 550                 555                 560
Ser Leu Trp Pro Gly Glu Ser Tyr Phe Cys Tyr Phe Gly Asp Gln Gln
                565                 570                 575
Ser Pro Ala Leu Leu Thr Ser Ser Gly Val Met Cys Pro Ser Pro Asp
                580                 585                 590
Pro Ser Glu Ala Pro Val Leu Gln Arg Gly Ala Asp His Ile Ser Val
                595                 600                 605
Asn Val Glu Leu Arg Phe Gly Ala Val Val Ile Ala Ser Thr Ser Leu
                610                 615                 620
Ser Phe Tyr Asp Cys Val Ala Val Thr Ala Ser Ser Pro Ser Ala Pro
625                 630                 635                 640
Cys Arg Ala Cys Val Ser Ser Arg Trp Gly Cys Asn Trp Cys Val Trp
                645                 650                 655
Gln Gln Leu Cys Thr His Lys Ala Ser Cys Asp Ala Gly Pro Met Val
                660                 665                 670
Ala Ser Gln Gln Ser Pro Leu Leu Pro Leu Ile Pro Pro Ala Arg Asp
                675                 680                 685
Glu Leu Thr Pro Phe Pro Pro Val Pro Gln Thr Val Thr Pro
                690                 695                 700
```

-continued

```
Thr Pro Asn Ser Phe Pro Ile Glu Pro Arg Ala Pro Ser Thr Ala Ser
705                 710                 715                 720

Asp Val Leu Pro Gly Ala Lys Pro Ser Arg Leu Ser Leu Trp Gly Pro
            725                 730                 735

Trp Ala Gly Pro Gly Pro Ile Leu Ser Pro Thr Ser Thr Glu Ser Pro
        740                 745                 750

Leu His Glu Lys Pro Leu Pro Pro Asp Pro Thr Ile Pro Gly Thr
    755                 760                 765

Thr Val Pro Ala Pro Thr Gly Leu Gly Pro Ser Thr Thr Pro Glu Asp
770                 775                 780

Leu Leu Ala Ser Tyr Pro Phe Pro Ser Asp Ala Ala Val Ser Pro
785                 790                 795                 800

Ala Glu Pro Gly Pro Glu Ala Leu Pro Ser Met Val Ala Leu Asp Gln
            805                 810                 815

Pro Pro Gly Thr Val Pro Asp Thr Thr Phe Pro Gly Ala Pro Gly Ser
            820                 825                 830

Met Lys Pro Val Leu Asp Trp Leu Thr Lys Gly Gly Gly Glu Leu Pro
            835                 840                 845

Glu Ala Asp Glu Trp Met Gly Gly Asp Thr Pro Ala Phe Ser Thr Ser
850                 855                 860

Thr Leu Leu Ser Gly Asp Gly Asp Ser Ala Glu His Glu Gly Pro Pro
865                 870                 875                 880

Ala Pro Leu Ile Leu Leu Ser Ser Leu Asp Tyr Gln Tyr Asp Thr Pro
                885                 890                 895

Gly Leu Trp Glu Leu Gly Glu Val Asn Gln Arg Val Ser Ser Cys Pro
            900                 905                 910

Cys Val Glu Thr Val Gln Gly Ser Leu Leu Ile Pro Val His Val Glu
            915                 920                 925

Arg Glu Val Gln Leu Arg Gly Arg Asn Leu Trp Leu Phe Gln Asp Gly
930                 935                 940

Pro Arg Ser Ser Glu Cys Val Leu Glu Leu Gly Ser Arg Glu Val Ala
945                 950                 955                 960

Val Glu Ala Gln Val Glu Cys Ala Pro Pro Asp Val Trp Cys His
            965                 970                 975

Ile Lys Cys Gln Gln His Gln Phe Ser Tyr Glu Ala Leu Lys Pro Glu
            980                 985                 990

Leu Gln Val Gly Leu Phe Leu Arg Trp Ala Gly Gly Leu Arg Val Asp
            995                 1000                1005

Ser Ala Asp Gly Leu His Val Val Leu Tyr Asp Cys Ser Val Gly
    1010                1015                1020

His Gly Asp Cys Ser Arg Cys Gln Thr Ala Met Pro Gln Tyr Asp
    1025                1030                1035

Cys Val Trp Cys Glu Gly Glu Arg Pro Arg Cys Val Ala Arg Glu
    1040                1045                1050

Ala Cys Asn Glu Ala Glu Thr Val Ala Thr Gln Cys Pro Ala Pro
    1055                1060                1065

Leu Ile His Ser Val Asp Pro Leu Thr Gly Pro Ile Asp Gly Gly
    1070                1075                1080

Thr Arg Val Thr Ile Arg Gly Ser Asn Leu Gly Gln His Val Gln
    1085                1090                1095

Asp Val Leu Asp Met Val Arg Val Ala Gly Val Pro Cys Ala Val
    1100                1105                1110
```

-continued

```
Asp Ala Gly Glu Tyr Asp Val Ser Ser Ser Leu Val Cys Ile Thr
1115                 1120                 1125

Gly Ala Ser Gly Glu Glu Val Thr Gly Thr Val Ala Val Glu Val
1130                 1135                 1140

Pro Gly Arg Gly His Gly Val Ser Glu Phe Ser Phe Ala Tyr Gln
1145                 1150                 1155

Asp Pro Lys Val His Ser Ile Phe Pro Ala Arg Gly Pro Arg Ala
1160                 1165                 1170

Gly Gly Thr Arg Leu Thr Leu His Gly Ser Lys Leu Leu Thr Gly
1175                 1180                 1185

Arg Leu Glu Asp Ile Arg Val Val Val Gly Asp Gln Pro Cys His
1190                 1195                 1200

Leu Leu Leu Glu Gln Gln Ser Glu Gln Leu His Cys Glu Thr Gly
1205                 1210                 1215

Pro Tyr Pro Val Pro Ala Glu Leu Pro Val Thr Val Leu Phe Gly
1220                 1225                 1230

Ala Thr Glu Arg Arg Leu Gln His Gly Gln Phe Lys Tyr Thr Ser
1235                 1240                 1245

Asp Pro Asn Val Thr Ser Val Gly Pro Ser Lys Ser Phe Phe Ser
1250                 1255                 1260

Gly Gly Arg Glu Ile Trp Val Arg Gly Gln Asp Leu Asp Val Val
1265                 1270                 1275

Gln Arg Pro Arg Ile Arg Val Thr Val Val Pro Arg Gln His Gly
1280                 1285                 1290

Gln Gly Leu Ala Gln Lys Gln His Val Val Pro Glu Lys Phe Glu
1295                 1300                 1305

Glu Pro Cys Leu Val Asn Ser Ser His Leu Leu Met Cys Arg Thr
1310                 1315                 1320

Pro Ala Leu Pro Gly Pro Pro Trp Asp Ser Gly Val Gln Val Glu
1325                 1330                 1335

Phe Ile Leu Asp Asn Met Val Phe Asp Phe Ala Ala Leu Ser Pro
1340                 1345                 1350

Thr Pro Phe Ser Tyr Glu Ala Asp Pro Thr Leu Arg Ser Leu Asn
1355                 1360                 1365

Pro Glu Asp Pro Ser Thr Pro Phe Arg His Lys Pro Gly Ser Val
1370                 1375                 1380

Phe Ser Val Glu Gly Glu Asn Leu Asp Leu Ala Met Ser Lys Glu
1385                 1390                 1395

Glu Val Val Ala Met Ile Gly Asp Gly Pro Cys Val Val Lys Thr
1400                 1405                 1410

Leu Thr Arg Asn His Leu Tyr Cys Glu Pro Pro Val Glu Gln Pro
1415                 1420                 1425

Leu Pro His Pro His Ala Leu Arg Glu Ala Pro Asp Ala Leu Pro
1430                 1435                 1440

Glu Phe Thr Val Gln Met Gly Asn Leu Arg Phe Ser Leu Gly His
1445                 1450                 1455

Val Gln Tyr Asp Gly Glu Ser Pro Val Ala Phe Pro Val Ala Ala
1460                 1465                 1470

Gln Val Gly Leu Gly Val Gly Thr Ser Leu Leu Ala Leu Gly Val
1475                 1480                 1485

Ile Ile Ile Val Leu Ile Tyr Arg Arg Lys Ser Lys Gln Ala Leu
1490                 1495                 1500

Arg Asp Tyr Lys Lys Val Gln Ile Gln Leu Glu Asn Leu Glu Ser
1505                 1510                 1515
```

-continued

```
Ser Val Arg Asp Arg Cys Lys Lys Glu Phe Thr Asp Leu Met Thr
1520                1525                1530

Glu Met Thr Asp Leu Thr Ser Asp Leu Leu Gly Ser Gly Ile Pro
1535                1540                1545

Phe Leu Asp Tyr Lys Val Tyr Ala Glu Arg Val Phe Phe Pro Gly
1550                1555                1560

Tyr Arg Glu Ser Pro Leu His Arg Asp Leu Gly Val Pro Asp Ser
1565                1570                1575

Arg Arg Pro Thr Val Glu Gln Gly Leu Gly Gln Leu Ser Asn Leu
1580                1585                1590

Leu Asn Ser Lys Leu Phe Leu Thr Lys Phe Ile His Thr Leu Glu
1595                1600                1605

Ser Gln Arg Thr Phe Ser Ala Arg Asp Arg Ala Tyr Val Ala Ser
1610                1615                1620

Leu Leu Thr Val Ala Leu His Gly Lys Leu Glu Tyr Phe Thr Asp
1625                1630                1635

Ile Leu Arg Thr Leu Leu Ser Asp Leu Val Ala Gln Tyr Val Ala
1640                1645                1650

Lys Asn Pro Lys Leu Met Leu Arg Arg Thr Glu Thr Val Val Glu
1655                1660                1665

Lys Leu Leu Thr Asn Trp Met Ser Ile Cys Leu Tyr Thr Phe Val
1670                1675                1680

Arg Asp Ser Val Gly Glu Pro Leu Tyr Met Leu Phe Arg Gly Ile
1685                1690                1695

Lys His Gln Val Asp Lys Gly Pro Val Asp Ser Val Thr Gly Lys
1700                1705                1710

Ala Lys Tyr Thr Leu Asn Asp Asn Arg Leu Leu Arg Glu Asp Val
1715                1720                1725

Glu Tyr Arg Pro Leu Thr Leu Asn Ala Leu Leu Ala Val Gly Pro
1730                1735                1740

Gly Ala Gly Glu Ala Gln Cys Val Pro Val Lys Val Leu Asp Cys
1745                1750                1755

Asp Thr Ile Ser Gln Ala Lys Glu Lys Met Leu Asp Gln Leu Tyr
1760                1765                1770

Lys Gly Val Pro Leu Ala Gln Arg Pro Asp Ser Cys Thr Leu Asp
1775                1780                1785

Val Glu Trp Arg Ser Gly Val Ala Gly His Leu Ile Leu Ser Asp
1790                1795                1800

Glu Asp Val Thr Ser Glu Leu Gln Gly Leu Trp Arg Arg Leu Asn
1805                1810                1815

Thr Leu Gln His Tyr Lys Val Pro Asp Gly Ala Thr Val Ala Leu
1820                1825                1830

Val Pro Cys Leu Thr Lys His Ile Leu Arg Glu Asn Gln Asp Tyr
1835                1840                1845

Val Pro Gly Glu Arg Thr Pro Met Leu Glu Asp Val Asp Glu Gly
1850                1855                1860

Gly Ile Arg Pro Trp His Leu Val Lys Pro Ser Asp Glu Pro Glu
1865                1870                1875

Pro Pro Arg Pro Arg Arg Gly Ser Leu Arg Gly Gly Glu Arg Glu
1880                1885                1890

Arg Ala Lys Ala Ile Pro Glu Ile Tyr Leu Thr Arg Leu Leu Ser
1895                1900                1905

Met Lys Gly Thr Leu Gln Lys Phe Val Asp Asp Leu Phe Gln Val
1910                1915                1920
```

```
Ile Leu Ser Thr Ser Arg Pro Val Pro Leu Ala Val Lys Tyr Phe
1925                1930                1935

Phe Asp Leu Leu Asp Glu Gln Ala Gln Gln His Gly Ile Ser Asp
1940                1945                1950

Gln Asp Thr Ile His Ile Trp Lys Thr Asn Ser Leu Pro Leu Arg
1955                1960                1965

Phe Trp Ile Asn Ile Ile Lys Asn Pro Gln Phe Val Phe Asp Val
1970                1975                1980

Gln Thr Ser Asp Asn Met Asp Ala Val Leu Leu Val Ile Ala Gln
1985                1990                1995

Thr Phe Met Asp Ala Cys Thr Leu Ala Asp His Lys Leu Gly Arg
2000                2005                2010

Asp Ser Pro Ile Asn Lys Leu Leu Tyr Ala Arg Asp Ile Pro Arg
2015                2020                2025

Tyr Lys Gln Met Val Glu Arg Tyr Tyr Ala Asp Ile Arg Gln Thr
2030                2035                2040

Val Pro Ala Ser Asp Gln Glu Met Asn Ser Val Leu Ala Glu Leu
2045                2050                2055

Ser Arg Asn Cys Ser Ala Asp Leu Gly Ala Arg Val Ala Leu His
2060                2065                2070

Glu Leu Tyr Lys Tyr Ile Asn Lys Tyr Tyr Asp Gln Ile Ile Thr
2075                2080                2085

Ala Leu Glu Glu Asp Gly Thr Ala Gln Lys Met Gln Leu Gly Tyr
2090                2095                2100

Arg Leu Gln Gln Ile Ala Ala Ala Val Glu Asn Lys Val Thr Asp
2105                2110                2115

Leu
```

In one embodiment, the PlexinB agonist and/or PlexinB polypeptide is from a mammalian species (e.g., of human or murine origin). In another embodiment, the PlexinB agonist and/or PlexinB polypeptide can be a mutant or variant polypeptide. As used herein, a "mutant" or "variant" polypeptide contains at least one amino acid sequence alteration as compared to the amino acid sequence of the corresponding wild-type polypeptide. An amino acid sequence alteration can be, for example, a substitution, a deletion, or an insertion of one or more amino acids.

The PlexinB agonist and/or PlexinB polypeptide can have any combination of amino acid substitutions, deletions or insertions. In one embodiment, isolated PlexinB agonists and/or PlexinB polypeptides have an integer number of amino acid alterations such that their amino acid sequence shares at least 60, 70, 80, 85, 90, 95, 96, 97, 98, 99, 99.5 or 100% identity with an amino acid sequence of a wild-type polypeptide. As described herein, the PlexinB agonists and/or PlexinB polypeptides are highly conserved among species and the structures are known such that the skilled artisan would readily understand which regions of the PlexinB agonists and/or PlexinB polypeptide can be altered without affecting a desired function mediated by the PlexinB agonist and/or PlexinB. Percent sequence identity can be calculated using computer programs or direct sequence comparison. Exemplary computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y, which is hereby incorporated by reference in its entirety). The BLASTP and TBLASTN programs are publicly available from NCBI and other sources. The well-known Smith Waterman algorithm may also be used to determine identity.

Amino acid substitutions in the PlexinB agonist and/or PlexinB polypeptide may be "conservative" or "non-conservative." As used herein, "conservative" amino acid substitutions are substitutions wherein the substituted amino acid has similar structural or chemical properties, and "non-conservative" amino acid substitutions are those in which the charge, hydrophobicity, or bulk of the substituted amino acid is significantly altered. Non-conservative substitutions will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of conservative amino acid substitutions include those in which the substitution is within one of the five following groups: 1) small aliphatic, nonpolar or slightly polar residues (Ala, Ser, Thr, Pro, Gly); 2) polar, negatively charged residues and their amides (Asp, Asn, Glut, Gln); polar, positively charged residues (His, Arg, Lys); large aliphatic, nonpolar residues (Met, Leu, Ile, Val, Cys); and large aromatic resides (Phe, Tyr, Trp). Examples of non-conservative amino acid substitutions are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

Substitutions can be made using any amino acid or amino acid analog. For example, the substitutions at any desired position can be made with any of the naturally occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine). A person having ordinary skill in the art could readily make equivalent alterations in the corresponding polypeptides from across species (e.g., rat, hamster, guinea pig, gerbil, rabbit, dog, cat, horse, pig, sheep, cow or non-human primate).

The PlexinB agonists and/or PlexinB polypeptides described herein are further defined as having the ability to affect GABAergic synapses and inhibitory neurons as described further herein. Additional biological activities of the PlexinB agonists and/or PlexinB polypeptides are well-known in the art. As compared to the corresponding wild-type polypeptide, PlexinB agonist and/or PlexinB polypeptide variants, such as fragments, fusion proteins, and the like can have altered amount, structure, subcellular localization, and/or activity of at least 50%, 60%, 70%, 80%, 90%, 100%, 150%, 200%, 300%, 400%, 500%, 1000% or more in excess of that relative to the corresponding wild-type polypeptide. Exemplary methods for determining activity levels and functional effects on neurons and synapses are well-known in the art and described further herein.

The PlexinB agonists and/or PlexinB polypeptides described herein can correspond to a full-length polypeptide, or can be a fragment of a full-length polypeptide. As used herein, a "fragment" refers to any subset of the polypeptide that is shorter than the full-length polypeptide. In one embodiment, the PlexinB agonists and/or PlexinB polypeptides are those that retain at least one biological activity described herein related to GABAergic synapses and inhibitory neurons. Such polypeptide fragments can be, for example, 5, 10, 15, 20, 25, 30, 35, 40, 45, 50, or more amino acids shorter than the corresponding full-length polypeptide. In some embodiments, the extracellular domain of the PlexinB agonist, such as Sema4D and fragments thereof, is sufficient to retain the at least one biological activity. For example, amino acid residues 24 to 711 of mouse Sema4D, as well as 27 to 490 of mouse Sema4D, are demonstrated herein to retain such biological activity.

The PlexinB agonists and/or PlexinB polypeptides described herein can also be modified according to a number of well-known methods. For example, they can be modified by chemical moieties that may be present in polypeptides in a normal cellular environment, for example, phosphorylation, methylation, amidation, sulfation, acylation, glycosylation, sumoylation, and ubiquitylation. In some embodiments, they can also be modified with a label capable of providing a detectable signal, either directly or indirectly, including, but not limited to, radioisotopes and fluorescent compounds. Such polypeptides can also be modified by chemical moieties that are not normally added to polypeptides in a cellular environment. Such modifications can be introduced into the molecule by reacting targeted amino acid residues of the polypeptide with an organic derivatizing agent that is capable of reacting with selected side chains or terminal residues. Another modification is cyclization of the protein.

The PlexinB agonists and/or PlexinB polypeptides described herein can also be coupled to other polypeptides to form fusion proteins according to well-known methods in the art. For example, the PlexinB agonist and/or PlexinB fusion polypeptides having a first fusion partner comprising all or a part of a PlexinB agonist (e.g., Sema4D) and/or PlexinB fusion protein fused (i) directly to a second polypeptide or, (ii) optionally, fused to a linker peptide sequence that is fused to the second polypeptide. The presence of the fusion partner can alter the solubility, affinity and/or valency of the PlexinB agonist and/or PlexinB polypeptide. As used herein, "valency" refers to the number of binding sites available per molecule. Fusion proteins described herein include any combination of amino acid alteration (i.e. substitution, deletion or insertion), fragment of the PlexinB agonist and/or PlexinB polypeptide, and/or modification as described above. A large number of polypeptide sequences that are routinely used as fusion protein binding partners are well known in the art. Examples of useful polypeptide binding partners include, but are not limited to, Fc tags, antibody fragments, green fluorescent protein (GFP), glutathione S-transferase (GST), polyhistidine, myc, hemaglutinin, Flag® tag (Kodak, New Haven, Conn.), maltose E binding protein, protein A, and one or more domains of an Ig heavy chain constant region.

Isolated nucleic acid sequences encoding the PlexinB agonists (e.g., Sema4D) and/or PlexinB polypeptides, and complements thereof, are further disclosed herein. As used herein, "isolated nucleic acid" refers to a nucleic acid that is separated from other nucleic acid molecules that are present in a genome, including nucleic acids that normally flank one or both sides of the nucleic acid in the genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

Nucleic acids, such as those described above, can be inserted into vectors for expression in cells. As used herein, a "vector" is a replicon, such as a plasmid, phage, or cosmid, into which another DNA segment may be inserted so as to bring about the replication of the inserted segment. Vectors can be expression vectors. An "expression vector" is a vector that includes one or more expression control sequences, and an "expression control sequence" is a nucleic acid sequence that controls and regulates the transcription and/or translation of another nucleic acid sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable nucleic acid vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, adeno-associated viruses, poliovirus, SV40, and the like, phagemids, cosmids, fosmids, bacterial artificial chromosomes, P1-based artificial chromosomes, yeast plasmids, yeast artificial chromosomes, and other vectors. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.). In some embodiments of the present technology, vectors suitable for use in prokaryotic host cells are preferred. Accordingly, exemplary vectors for use in prokaryotes such as *Escherichia coli* include, but are not limited to, pACYC184, pBeloBac11, pBR332, pBAD33, pBBR1MCS and its derivatives, pSC101, SuperCos (cosmid), pWE15 (cosmid), pTrc99A, pBAD24, vectors containing a ColE1 origin of replication and its derivatives, pUC, pBluescript, pGEM, and pTZ vectors.

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to those described herein for use as fusion partners.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. For stable transformation, a nucleic acid vector or construct will generally further include a selectable marker, e.g., any of several well-known selectable markers such as neomycin resistance, ampicillin resistance, tetracycline resistance, chloramphenicol resistance, kanamycin resistance, and the like. Stable transformation can also be effected (e.g., selected for) using a nutritional marker gene that confers prototrophy for an essential amino acid such as URA3, HIS3, LEU2, MET2, LYS2 and the like. Suitable host cells include both eukaryotic and prokaryotic cells. Eukaryotic host cells, include without limitation, animal cells, fungal cells, insect cells, plant cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thennotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Neurospora crassa, Chlamydomonas reinhardtii*, and the like. Suitable prokaryotic cells include, but are not limited to, any of a variety of laboratory strains of *Escherichia coli, Lactobacillus* sp., *Salmonella* sp., *Shigella* sp., *Rhodococcus* sp., *Bacillus* sp., *Pseudomonas* sp., and the like (see, e.g., Carrier et al., *J. Immunol.*, 148:1176-1181 (1992) and Sizemore et al., *Science*, 270:299-302 (1995), which are hereby incorporated by reference in their entirety).

Methods for producing polypeptides and nucleic acid molecules for use in accordance with the present technology are well-known in the art.

In another embodiment, the PlexinB agonist is a small molecule PlexinB agonist. Small molecules of the present technology are entities having carbon and hydrogen atoms, as well as heteroatoms, which include, but are not limited to, nitrogen, sulfur, oxygen, and phosphorus. Atoms in a small molecule are linked together via covalent and ionic bonds; the former is typical for small organic compounds and the latter is typical of small inorganic compounds. The arrangement of atoms in a small organic molecule can represent a chain, e.g., a carbon-carbon chain or carbon-heteroatom chain, or ring containing carbon atoms, e.g., benzene, or a combination of carbon and heteroatoms, i.e., heterocycles, for example, a pyrimidine or quinazoline. A combination of one or more chains in a small organic molecule attached to a ring system constitutes a substituted ring system and fusion of two rings constitutes a fused polycyclic system, which can be referred to as simply a polycyclic system. Small molecules include both compounds found in nature, such as hormones, neurotransmitters, nucleotides, amino acids, sugars, lipids and their derivatives, and those compounds made synthetically, either by traditional organic synthesis, bio-mediated synthesis, or a combination thereof. See, e.g., Ganesan et al., "Recent Developments in Combinatorial Organic Synthesis," *Drug Discov. Today*, 7(1): 47-55 (2002); Lou et al., "Novel Strategies for Solid-Phase Construction of Small-Molecule Combinatorial Libraries," *Drug Discov. Today*, 6(24): 1288-1294 (2001). Furthermore, small molecules include, for example, lipids and polymers of polysaccharides, as well as derivatives thereof, such as, e.g., lipopolysaccharides. Any suitable small molecule that binds to and activates the PlexinB receptor can be used in the context of the present technology. In one embodiment, the small molecule binds to and actives the PlexinB1 receptor.

In accordance with the present technology, such PlexinB agonists and/or PlexinB polypeptides can be used for identifying, assessing, prognosing, and treating neurological disorders, which can be related to excessive or unwanted neuronal activity or too little neuronal activity.

As used herein, the term "neurological disorders" includes neurological conditions that are caused or result from excessive or unwanted neuronal activity as well as neurological conditions related to too little neuronal activity. Examples of neurological disorders include, without limitation, epilepsy, Alzheimer's disease, schizophrenia or schizoaffective disorder, bipolar disorder or unipolar disorder, autism or autism spectrum disorder, a disorder resulting from neural damage such as spinal injuries or brain injuries, amyotrophic lateral sclerosis (ALS or Lou Gehrig's disease), Huntington's disease, Parkinson's disease, symptoms thereof, pantothenate kinase associated neurodegeneration (PKAN), HIV encephalopathy, chronic traumatic encephalopathy (CTE), dementia, mood disorder, anxiety disorders, generalized anxiety disorder (GAD), panic disorder, aggression, psychiatric symptoms, anger, rejection sensitivity, insomnia, cognitive or memory disturbances or impairment; seizures of any cause (e.g., epiliptoform epilepsy), primary or metastatic brain tumors, depression (e.g., bipolar depression), major depressive disorder (MDD), postnatal depression, dysthymia, depression associated with Alzheimer's disease, Parkinson's disease, or psychosis, pain (e.g., neuropathic pain, lower back pain, fibromyalgia syndrome (FS), osteoarthritis pain, arthritis pain, chronic pain), chronic fatigue syndrome (CFS), stroke, ischemia and neuronal loss following hypoxia, hypoglycemia, ischemia, trauma, and nervous insult, attention deficit hyperactivity disorder (ADHD), manic-depressive disorder, obsessive compulsive disorder (OCD), posttraumatic stress disorder (PTSD), acute stress disorder, social phobia, simple phobias, pre-menstrual dysphoric disorder (PMDD), social anxiety disorder (SAD), supranuclear palsy, ischemic diseases, substance abuse disorders, chemical dependencies, nicotine addiction, cocaine addiction, amphetamine addiction, alcohol addiction, Lesch-Nyhan syndrome, neurodegenerative diseases, late luteal phase syndrome or narcolepsy, movement disorders, extrapyramidal syndrome, Tic disorders, restless leg syndrome (RLS), tardive dyskinesia, stress urinary incontinence (SUI), and migraine. In some embodiments, particular types of epilepsy may be included, such as partial-onset epilepsy, generalized-onset epilepsy, idiopathic epilepsy, frontal lobe epilepsy, Lennox-Gastaut Syndrome, early myoclonic encephalopathy, benign childhood epilepsy, juvenile myoclonic epilepsy, epileptic encephalopathy, epileptiform encephalopathy, posttraumatic epilepsy, temporal lobe epilepsy, reflex epilepsy, Epilepsia Partialis Continua, Status Epilepticus, or any other type of epilepsy known in the art. In some embodiments, the neurological disorders are due to excessive or unwanted activity in GABAergic neurons (e.g., projecting GABAergic neurons, pallido-subthalamic GABAergic neurons, striatopallidal GABA neurons, GABAergic efferent neurons, striatopallidal GABAergic neurons, or any other GABA receptor-expressing neuron known in the art) and require an increase in inhibition.

GABA is the major inhibitory neurotransmitter of the brain, occurring in 30-40% of all synapses (second only to glutamate as a major brain neurotransmitter). The GABA concentration in the brain is 200-1000 times greater than that of the monoamines or acetylcholine. GABA concentrations are decreased in the basal ganglia of Huntington's disease patients, and this deficiency is likely to contribute to the dementia, mood disorders, and psychoses related thereto. Postmortem studies of Alzheimer's patients have shown central GABA deficits, showing the importance of GABA levels in Alzheimer's disease etiology. Similarly, animal studies have shown that increasing GABA levels can inhibit aggression.

In some embodiments, activity or expression of PlexinB agonists and/or PlexinB in neurons can be diminished in order to reduce inhibition of neurons to thereby increase neuronal activity and beneficially treat neurological conditions resulting from too little neuronal activity. Such neurological conditions include, but are not limited to, hepatic encephalopathy, depressed consciousness, and coma. Methods of reducing activity and/or expression of the PlexinB agonists and/or PlexinB are well known in the art and include, without limitation, the use of antisense molecules (e.g., RNAi, siRNA, miRNA, piwiRNA, and the like), ribozymes, blocking antibodies, dominant negative variants, small molecule inhibitors, and the like.

In accordance with one embodiment of the present technology, the PlexinB agonist is a Sema4D polypeptide selected from the group consisting of polypeptides having at least 80%, 90%, or 95% identity over the entire length with the amino acid sequences of SEQ ID NOs: 2, 4, 6, 8, and 10.

In accordance with another embodiment of the present technology, the PlexinB agonist includes the extracellular fragment of the Sema4D polypeptide comprising amino acid residues 24-711 or 27-490 of the amino acid sequence of SEQ ID NO: 6 or a corresponding amino acid region in an ortholog thereof.

This technology also relates to a method of modulating neuronal activity in the central nervous system or peripheral nervous system of a subject in need thereof by modulating the number of GABAergic synapses between at least two neurons. The method includes administering to the subject a therapeutic agent that is a PlexinB agonist or a nucleic acid molecule encoding a PlexinB agonist, to thereby modulate the neuronal activity of the subject in need thereof.

In one embodiment, the PlexinB agonist is a Sema4D polypeptide or an extracellular fragment thereof, or a nucleic acid molecule encoding said Sema4D polypeptide or extracellular fragment thereof.

The PlexinB agonist can be administered to increase the number of GABAergic synapses between at least two neurons, thereby decreasing neuronal activity of the subject in need thereof.

In accordance with one embodiment of the present technology, the therapeutic agent is administered directly into the central or peripheral nervous system of the subject.

This technology further relates to a method of treating a neurological disorder that would benefit from modulating neuronal activity in the central nervous system or peripheral nervous system of a subject in need thereof. The method includes administering to the subject a therapeutic agent that is a PlexinB agonist or a nucleic acid molecule encoding a PlexinB agonist, thereby treating the neurological disorder of the subject in need thereof.

As used herein, "subject" refers to any animal that exhibits a neurological condition or disorder, as described infra, which is amenable to treatment in accordance with the methods of the present technology. Preferably, the subject is a mammal. Exemplary mammalian patients include, without limitation, humans, non-human primates, dogs, cats, rodents (e.g., mouse, rat, guinea pig), horses, cattle and cows, sheep, and pigs.

In one embodiment, the PlexinB agonist is a Sema4D polypeptide or an extracellular fragment thereof, or a nucleic acid molecule encoding said Sema4D polypeptide or extracellular fragment thereof.

Suitable neurological disorders are described herein.

This technology also relates to a method of treating a neurological disorder that would benefit from modulating neuronal activity in the central nervous system or peripheral nervous system of a subject in need thereof. This method includes administering to the subject an agent that inhibits the level of expression or activity of a PlexinB agonist or an active peptide fragment or derivative thereof, thereby treating the neurological disorder of the subject in need thereof.

In one embodiment, the agent inhibits the level of expression or activity of a PlexinB1 agonist. In a further embodiment, the agent inhibits the level of expression or activity of a Sema4D polypeptide or an active fragment or derivative thereof.

In accordance with one embodiment of the present technology, the number of GABAergic synapses formed between at least two neurons of the subject decreases.

In accordance with another embodiment of the present technology, a method of treating a neurological disorder that would benefit from modulating neuronal activity in the central nervous system or peripheral nervous system of a subject in need thereof includes administering to the subject an agent that inhibits the level of expression or activity of a PlexinB polypeptide or an active peptide fragment or derivative thereof, thereby treating the neurological disorder of the subject in need thereof. In one particular embodiment, the agent inhibits the level of expression or activity of a PlexinB1 polypeptide or an active peptide fragment or derivative thereof.

In a further embodiment, a method of treating a neurological disorder that would benefit from modulating neuronal activity in the central nervous system or peripheral nervous system of a subject in need thereof includes administering to the subject an agent that inhibits the level of expression or activity of a PlexinB agonist or an active peptide fragment or derivative thereof and administering to the subject an agent that inhibits the level of expression or activity of a PlexinB polypeptide or an active peptide fragment or derivative thereof, thereby treating the neurological disorder of the subject in need thereof.

In yet a further embodiment, the neurological disorder of any of the above methods is selected from the group consisting of depressed consciousness, coma, and hepatic encephalopathy.

In yet another embodiment, the agent is selected from the group consisting of an antisense nucleic acid molecule, RNAi molecule, siRNA molecule, miRNA molecule, piwiRNA molecule, ribozyme, blocking antibody, dominant negative polypeptide, and small molecule inhibitors.

Techniques for contacting, administration, pharmaceutical preparations, and dosing thereof are well-known in the art. For example, the PlexinB agonist can be contacted with the at least two neurons using any of the forms of administration described herein, such as in the form of a pharmaceutical composition.

Further, methods of screening agents to determine the ability to affect synapse formation and neuron activity are known in the art. Two examples of genetic screens are described in Paradis et al., An RNAi-based Approach Identifies Molecules Required for Glutamatergic and GABAergic Synapse Development," *Neuron,* 53(2):217-32 (2007) and Sharma et al., "High-Throughput Genetic Screen for Synaptogenic Factors: Identification of LRP6 as Critical for Excitatory Synapse Development," *Cell Rep.,* 5(5):1330-41 (2013), which are hereby incorporated by reference in their entirety.

The agents of the present technology may be administered in any suitable or medically-accepted means for introducing a therapeutic directly or indirectly into a subject, including but not limited to orally, subcutaneously, intravenously, intramuscularly, parenterally, intrasynovially, intra-articularly, intraperitoneally, topically, transdermally, or by application to a mucosal surface. In a one embodiment, the therapeutic agent is administered intrasynovially. The therapeutic composition may be delivered to the subject at multiple sites. The multiple administrations may be rendered simultaneously or over a period of several hours. In certain cases it may be beneficial to provide a continuous flow of the therapeutic composition. Additional therapy may be administered on a period basis, for example, daily, weekly or monthly.

The therapeutic proteins, peptides, nucleic acid molecules, or small molecules for administration may be formulated with uptake or absorption enhancers to increase their efficacy. Such enhancers include for example, salicylate, glycocholate/linoleate, glycholate, aprotinin, bacitracin, SDS caprate and the like (see e.g., Fix et al., "Strategies for Delivery of Peptides Utilizing Absorption-Enhancing Agents," *J. Pharm. Sci.,* 85:1282-1285 (1996); and Oliyai and Stella, "Prodrugs of Peptides and Proteins for Improved Formulation and Delivery," *Ann. Rev. Pharmacol. Toxicol.,* 33:521-544 (1993), which are hereby incorporated by reference in their entirety).

The amount of agent in a given dosage will vary according to the size of the individual to whom the therapy is being administered as well as the characteristics of the disorder being treated. In exemplary treatments, it may be necessary to administer about 50 mg/day, 75 mg/day, 100 mg/day, 150 mg/day, 200 mg/day, 250 mg/day. These concentrations may be administered as a single dosage form or as multiple doses. Standard dose-response studies, first in animal models and then in clinical testing, will reveal optimal dosages for particular disease states and patient populations.

It will also be apparent that dosing should be modified if the PlexinB agonist or PlexinB polypeptide is administered in combination with other medications.

In a further embodiment of the technology, the PlexinB agonists and/or PlexinB polypeptides and/or agents that inhibit the level of expression or activity of a PlexinB agonist or an active peptide fragment or derivative thereof or of a PlexinB polypeptide are contacted or administered in combination with one or more additional therapeutic agents. Suitable additional therapeutic agents include any therapeutic agent effective in treating any of the neurological disorders described herein including, but not limited to, antiepileptic drugs, antidepressants, schizophrenia drugs, Parkinson's Disease drugs, Huntington's disease drugs, dementia drugs, mood or anxiety disorder drugs, aggression drugs, and insomnia drugs. Examples include, but are not limited to, valproate and levomepromazine, rotigotine, rasagiline, levodopa, carbidopa, dopamine agonists (bromocriptine, pramipexole, or ropinirole), COMT inhibitors (entacapone or tolcapone), MAO-B inhibitors (rasagiline or selegiline), amantadine, anticholinergic agents (benztropine or trihexyphenidyl), salfinamide, alprazolam, haloperidol, chlorpromazine, risperidone, paliperidone, olanzapine, ziprasidone, quetiapine, clozapine, lithium carbonate, diazepam, carbamazepine, selective serotonin re-uptake inhibitors (SSRI's) (ZOLOFT® or CELEXA®) tricyclic antidepressants, such as PAMELOR®, methylphenidate, reboxetine, atomoxetine (STRATTERA®), sertraline, citalopram, escitalopram, paroxetine, fluoxetine and fluvoxamine, dapoxetine, duloxetine, venlafaxine, desvenlafaxine, Milnacipran, and bupropion.

Another aspect of the technology is directed to a pharmaceutical composition. This pharmaceutical composition includes a pharmaceutically acceptable carrier along with a therapeutic agent that is a PlexinB agonist or a nucleic acid molecule encoding a PlexinB agonist. In one embodiment, the pharmaceutical composition includes one or more additional therapeutic agents. In one particular embodiment, the one or more additional therapeutic agents comprise a PlexinB polypeptide or a nucleic acid molecule encoding a PlexinB polypeptide.

In another embodiment, the pharmaceutical composition includes a pharmaceutically acceptable carrier along with a therapeutic agent that is a PlexinB polypeptide or a nucleic acid molecule encoding a PlexinB polypeptide.

The individual components of the pharmaceutical composition of the present technology, i.e., the PlexinB agonist, PlexinB polypeptide, and the additional therapeutic agents can be any of those described supra.

The pharmaceutical composition of the present technology also contains a carrier. Acceptable pharmaceutical carriers include solutions, suspensions, emulsions, excipients, powders, or stabilizers. The carrier should be suitable for the desired mode of delivery, discussed infra.

Pharmaceutical compositions suitable for injectable use (e.g., intravenous, intrasynovial, intra-arterial, intramuscular, etc.) may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable carriers and/or excipients, include, but are not limited to sterile liquids, such as water and oils, with or without the addition of a surfactant and other pharmaceutically and physiologically acceptable carrier. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

Oral dosage formulations of the pharmaceutical composition of the present technology can include standard carriers such as pharmaceutical grades of mannitol, lactose, starch, magnesium stearate, sodium saccharine, cellulose, magnesium carbonate, etc. Suitable carriers include lubricants and inert fillers such as lactose, sucrose, or cornstarch. In another embodiment, these compounds are tableted with conventional tablet bases such as lactose, sucrose, or cornstarch in combination with binders like acacia, gum gragacanth, cornstarch, or gelatin; disintegrating agents such as cornstarch, potato starch, or alginic acid; a lubricant like stearic acid or magnesium stearate; and sweetening agents such as sucrose, lactose, or saccharine; and flavoring agents such as peppermint oil, oil of wintergreen, or artificial flavorings. Generally, the ingredients are supplied either separately or mixed together in unit dosage form, for example, as a dry lyophilized powder or water free concentrate in a hermetically sealed container such as an ampule or sachette indicating the quantity of active agent.

As is known in the art, because orally administered agents need to survive the digestive system before cellular uptake, it is possible to administer the therapeutic agents of the present technology with any of a variety of stabilizing reagent that inhibits destruction thereof. One such type of stabilizing reagent is a mammalian colostrum, whether produced as a hyperimmune colostrum for antibody-based therapeutics or as an in vitro mixture of the therapeutic agent and colostrum.

This technology relates to the diagnosis, prognosis, treatment, and prevention of such neurological disorders based on the discovery described herein that the PlexinB agonist (e.g., Sema4D) and/or PlexinB polypeptide (e.g., PlexinB1 polypeptide) can modulate the number of GABAergic synapses between neurons and thereby regulate neuronal activity.

Thus, this technology relates to a method of modulating the number of GABAergic synapses between at least two neurons comprising contacting at least one of the neurons with a PlexinB agonist or a nucleic acid molecule encoding a PlexinB agonist to promote GABAergic synapse formation.

This technology further relates to the method, wherein the PlexinB agonist is a PlexinB1, a PlexinB2, and/or a PlexinB3 agonist. In a further embodiment, the PlexinB agonist is a polypeptide or an active peptide fragment or derivative thereof that binds to and activates the PlexinB1, PlexinB2, and/or PlexinB3 receptor. This technology further relates to the method, wherein the PlexinB agonist is a member of the Semaphorin protein family or a peptide derived from a Semaphorin that binds to and activates a PlexinB receptor. This technology further relates to the method, wherein the PlexinB agonist is a PlexinB1 agonist. The PlexinB1 agonist may be selected from the group consisting of a polypeptides having at least 80% identity over the entire length with the amino acid sequences of SEQ ID NOs: 2, 4, 6, 8, and 10.

This technology further relates to the method, wherein the number of GABAergic synapses formed between the two neurons increases without increasing the number of glutamatergic synapses between the two neurons.

This technology further relates to the method, wherein at least one of the neurons is an inhibitory neuron.

This technology further relates to the method, further comprising contacting at least one of the neurons with a PlexinB polypeptide or a nucleic acid molecule encoding the PlexinB polypeptide. In one embodiment, the PlexinB polypeptide is a PlexinB1 polypeptide.

This technology also relates to a method of modulating neuronal activity in the central nervous system or peripheral nervous system of a subject in need thereof by modulating the number of GABAergic synapses between at least two neurons, comprising administering to the subject a therapeutic agent that is a PlexinB agonist or a nucleic acid molecule encoding a PlexinB agonist, thereby modulating said neuronal activity of the subject in need thereof.

This technology further relates to the method, wherein the PlexinB agonist is a PlexinB1, a PlexinB2, and/or a PlexinB3 agonist. In a further embodiment, the PlexinB agonist is a polypeptide or an active peptide fragment or derivative thereof that binds to and activates the PlexinB1, PlexinB2, and/or PlexinB3 receptor. This technology further relates to the method, wherein the PlexinB agonist is a member of the Semaphorin protein family or a peptide derived from a Semaphorin that binds to and activates a PlexinB receptor. This technology further relates to the method, wherein the PlexinB agonist is a PlexinB1 agonist. The PlexinB1 agonist may be selected from the group consisting of a polypeptides having at least 80% identity over the entire length with the amino acid sequences of SEQ ID NOs: 2, 4, 6, 8, and 10.

This technology further relates to the method, wherein the number of GABAergic synapses formed between the two neurons increases without increasing the number of glutamatergic synapses between the two neurons.

This technology further relates to the method, wherein at least one of the neurons is an inhibitory neuron.

This technology further relates to the method, further comprising contacting at least one of the neurons with a PlexinB polypeptide or a nucleic acid molecule encoding the PlexinB polypeptide. In one embodiment, the PlexinB polypeptide is a PlexinB1 polypeptide.

This technology further relates to the method, wherein the therapeutic agent is administered directly into the central or peripheral nervous system of the subject.

This technology further relates to the method, wherein said administering is carried out orally, subcutaneously, intravenously, intramuscularly, parenterally, intrasynovially, intra-articularly, intraperitoneally, topically, transdermally, or by application to a mucosal surface.

This technology also relates to a method of treating a neurological disorder of a subject in need thereof, comprising administering to the subject a therapeutic agent that is a PlexinB agonist or a nucleic acid molecule encoding a PlexinB agonist, thereby treating the neurological disorder of the subject in need thereof.

This technology further relates to the method, wherein the PlexinB agonist is a PlexinB1, a PlexinB2, and/or a PlexinB3 agonist. In a further embodiment, the PlexinB agonist is a polypeptide or an active peptide fragment or derivative thereof that binds to and activates the PlexinB1, PlexinB2, and/or PlexinB3 receptor. This technology further relates to the method, wherein the PlexinB agonist is a member of the Semaphorin protein family or a peptide derived from a Semaphorin that binds to and activates a PlexinB receptor. This technology further relates to the method, wherein the PlexinB agonist is a PlexinB1 agonist. The PlexinB1 agonist may be selected from the group consisting of a polypeptides having at least 80% identity over the entire length with the amino acid sequences of SEQ ID NOs: 2, 4, 6, 8, and 10.

This technology further relates to the method, wherein the number of GABAergic synapses formed between at least two neurons of the subject increases without increasing the number of glutamatergic synapses between the two neurons.

This technology further relates to the method, wherein at least one of the neurons is an inhibitory neuron.

This technology further relates to the method, further comprising administering to the subject a PlexinB polypeptide or a nucleic acid molecule encoding the PlexinB polypeptide. In one embodiment, the PlexinB polypeptide is a PlexinB1 polypeptide.

This technology further relates to the method, wherein the therapeutic agent is administered directly into the central or peripheral nervous system of the subject.

This technology further relates to the method, wherein said administering is carried out orally, subcutaneously, intravenously, intramuscularly, parenterally, intrasynovially, intra-articularly, intraperitoneally, topically, transdermally, or by application to a mucosal surface.

This technology further relates to the method, wherein the neurological disorder is selected from the group consisting of epilepsy, Alzheimer's disease, schizophrenia or schizoaffective disorder, bipolar disorder or unipolar disorder, autism or autism spectrum disorder, a disorder resulting from neural damage, amyotrophic lateral sclerosis, Huntington's disease, Parkinson's disease, pantothenate kinase associated neurodegeneration, HIV encephalopathy, chronic traumatic encephalopathy, dementia, mood disorder, anxiety disorder, generalized anxiety disorder, panic disorder, aggression, psychiatric symptoms, anger, rejection sensitivity, insomnia, cognitive or memory disturbances or impairment, seizures, primary or metastatic brain tumors, depression, major depressive disorder, postnatal depression, dysthymia, depression associated with Alzheimer's disease, Parkinson's disease, or psychosis, pain, chronic fatigue syndrome, stroke, ischemia and neuronal loss following hypoxia, hypoglycemia, ischemia, trauma, and nervous insult, attention deficit hyperactivity disorder, manic-depressive disorder, obsessive compulsive disorder, posttraumatic stress disorder, acute stress disorder, social phobia, simple phobias, pre-menstrual dysphoric disorder, social anxiety disorder, supranuclear palsy, ischemic diseases, substance abuse disorders, chemical dependencies, nicotine addiction, cocaine addiction, amphetamine addiction, alcohol addiction, Lesch-Nyhan syndrome, neurodegenerative diseases, late luteal phase syndrome, narcolepsy, movement disorders, extrapyramidal syndrome, Tic disorders, restless leg syndrome (RLS), tardive dyskinesia, stress urinary incontinence (SUI), and migraine.

This technology also relates to a method of treating a neurological disorder of a subject in need thereof, comprising administering to the subject a therapeutic agent that inhibits the level of expression or activity of a PlexinB agonist or an active peptide fragment or derivative thereof, thereby treating the neurological disorder of the subject in need thereof.

This technology further relates to the method, wherein the PlexinB agonist is a PlexinB1, a PlexinB2, and/or a PlexinB3 agonist. In a further embodiment, the PlexinB agonist is a polypeptide or an active peptide fragment or derivative thereof that binds to and activates the PlexinB1, PlexinB2, and/or PlexinB3 receptor. This technology further relates to the method, wherein the PlexinB agonist is a member of the Semaphorin protein family or a peptide derived from a Semaphorin that binds to and activates a PlexinB receptor. This technology further relates to the method, wherein the PlexinB agonist is a PlexinB1 agonist. The PlexinB1 agonist may be selected from the group consisting of a polypeptides having at least 80% identity over the entire length with the amino acid sequences of SEQ ID NOs: 2, 4, 6, 8, and 10.

This technology further relates to the method, wherein the number of GABAergic synapses formed between at least two neurons of the subject decreases.

This technology further relates to the method, wherein at least one of the neurons is an inhibitory neuron.

This technology further relates to the method, further comprising administering to the subject an agent that inhibits the level of expression or activity of a PlexinB polypeptide. In one embodiment, the PlexinB polypeptide is a PlexinB1 polypeptide.

This technology further relates to the method, wherein the therapeutic agent is administered directly into the central or peripheral nervous system of the subject.

This technology further relates to the method, wherein said administering is carried out orally, subcutaneously, intravenously, intramuscularly, parenterally, intrasynovially, intra-articularly, intraperitoneally, topically, transdermally, or by application to a mucosal surface.

This technology further relates to the method, wherein the neurological disorder is selected from the group consisting of depressed consciousness, coma, and hepatic encephalopathy.

This technology further relates to the method, wherein the therapeutic agent and agent is selected from the group consisting of an antisense nucleic acid molecule, RNAi molecule, siRNA molecule, miRNA molecule, piwiRNA molecule, ribozyme, blocking antibody, dominant negative polypeptide, and small molecule inhibitors.

This technology also relates to a method of treating a neurological disorder of a subject in need thereof, comprising administering to the subject a therapeutic agent that inhibits the level of expression or activity of a PlexinB polypeptide, thereby treating the neurological disorder of the subject in need thereof. In one embodiment, the PlexinB polypeptide is a PlexinB1 polypeptide.

This technology further relates to the method, wherein the number of GABAergic synapses formed between at least two neurons of the subject decreases.

This technology further relates to the method, wherein at least one of the neurons is an inhibitory neuron.

This technology further relates to the method, wherein the therapeutic agent is administered directly into the central or peripheral nervous system of the subject.

This technology further relates to the method, wherein said administering is carried out orally, subcutaneously, intravenously, intramuscularly, parenterally, intrasynovially, intra-articularly, intraperitoneally, topically, transdermally, or by application to a mucosal surface.

This technology further relates to the method, wherein the neurological disorder is selected from the group consisting of depressed consciousness, coma, and hepatic encephalopathy.

This technology further relates to the method, wherein the therapeutic agent is selected from the group consisting of an antisense nucleic acid molecule, RNAi molecule, siRNA molecule, miRNA molecule, piwiRNA molecule, ribozyme, blocking antibody, dominant negative polypeptide, and small molecule inhibitors.

This technology also relates to a pharmaceutical composition comprising: a pharmaceutically acceptable carrier, and a therapeutic agent that is a PlexinB agonist.

This technology further relates to the pharmaceutical composition, wherein the PlexinB agonist is a PlexinB1, a PlexinB2, and/or a PlexinB3 agonist. In a further embodiment, the PlexinB agonist is a polypeptide or an active peptide fragment or derivative thereof that binds to and activates the PlexinB1, PlexinB2, and/or PlexinB3 receptor. This technology further relates to the pharmaceutical composition, wherein the PlexinB agonist is a member of the Semaphorin protein family or a peptide derived from a Semaphorin that binds to and activates a PlexinB receptor. This technology further relates to the pharmaceutical composition, wherein the PlexinB agonist is a PlexinB1 agonist. The PlexinB1 agonist may be selected from the group consisting of a polypeptides having at least 80% identity over the entire length with the amino acid sequences of SEQ ID NOs: 2, 4, 6, 8, and 10.

This technology further relates to the pharmaceutical composition, wherein the PlexinB agonist comprises an extracellular fragment of Sema4D polypeptide which comprises amino acid residues 24-711 or 27-490 of the amino acid sequence of SEQ ID NO: 6 or a corresponding amino acid region in an ortholog thereof.

This technology further relates to the pharmaceutical composition, further comprising one or more additional therapeutic agents. Suitable therapeutic agents include, for example, anti-epileptic drugs, antidepressants, schizophrenia drugs, Parkinson's Disease drugs, Huntington's disease drugs, dementia drugs, mood or anxiety disorder drugs, aggression drugs, and insomnia drugs.

This technology further relates to the pharmaceutical composition, wherein the one or more additional therapeutic agents comprise a PlexinB polypeptide or a nucleic acid molecule encoding a PlexinB polypeptide. In one embodiment, the PlexinB polypeptide is a PlexinB1 polypeptide.

This technology also relates to a pharmaceutical composition including: a pharmaceutically acceptable carrier, and a therapeutic agent that is a PlexinB polypeptide or a nucleic acid molecule encoding a PlexinB polypeptide. In one embodiment, the PlexinB polypeptide is a PlexinB1 polypeptide.

In order to gain insight into the mechanisms of GABAergic synapse formation and function, cultured hippocampal neurons and acute hippocampal slices were treated with the soluble, extracellular domain of Sema4D protein and were subsequently assayed for morphological and functional aspects related to GABAergic synapses. An unexpected rapid and robust increase in functional GABAergic synapse density with Sema4D treatment was observed that was entirely dependent on PlexinB1 receptor expression. In addition, GABAergic synapse assembly was monitored by time-lapse imaging of the fluorescently-tagged, GABAergic synapse-specific scaffolding protein, Gephyrin, in cultured neurons. It was determined that Sema4D treatment increased the rate of addition of GFP-Gephyrin along dendrites of imaged neurons through a previously underappreciated mechanism: splitting of pre-existing Gephyrin puncta. In addition, it is demonstrated herein that Sema4D treatment of an organotypic hippocampal slice model of epilepsy dramatically suppressed neuronal hyperexcitability within two hours of treatment through an increase in inhibition. The ability of Sema4D to rapidly drive GABAergic synapse formation and suppress network hyperexcitability described herein indicates its use as a treatment for epilepsy and other neurological disorders.

These aspects of the present technology are further illustrated by the examples below.

EXAMPLES

The following examples are provided to illustrate embodiments of the present technology, but they are by no means intended to limit its scope. All of the references cited in the Examples below are hereby incorporated by reference in their entirety.

Example 1—Materials and Methods: Mice

PlxnB1−/− mice were generated as described by Friedel et al., "Gene Targeting Using a Promoterless Gene Trap Vector ("Targeted Trapping") is an Efficient Method to Mutate a Large Fraction of Genes," *Proc. Natl. Acad. Sci. U.S.A.*, 102:13188-13193 (2005), which is hereby incorporated by reference in its entirety. Mice were cared for in accordance with Brandeis University IACUC. Timed pregnancies were set up between PlxnB1+/− males and females where the day of vaginal plug observation was designated as E0 and hippocampi were dissected at E16. Day of birth was designated as P0. Genotyping of all mice, including all embryos, was performed by PCR.

Example 2—Culture and Organotypic Slices

Neurons were dissociated and cultured at low density on an astrocyte feeder layer. Astrocytes were isolated from P0 rat cortex by plating dissociated cells at low density in DMEM +10% FBS on 10-cm tissue culture dishes. Once confluent, glia were trypsinized and plated on 12-mm glass coverslips in 24-well plates, which had been coated overnight at 37° C. with poly-D-lysine (20 µg/mL) and laminin (3.4 µg/mL). Dissociated hippocampal neurons from E18 rats or E16 mice were plated at a density of 80,000/well onto the confluent glia and grown in Neurobasal media (Invitrogen) with NS21 supplement (Chen et al., "NS21: Re-Defined and Modified Supplement B27 for Neuronal Cultures," *J. Neurosci. Methods*, 171:239-247 (2008), which is hereby incorporated by reference in its entirety). E18 rat and E16 mouse hippocampal dissections yield cultures that are neuron rich and contain primarily glutamatergic, pyramidal neurons and GABAergic interneurons. AraC (Sigma) was added to a final concentration of 5 µM 4-24 hours after plating, when glia were confluent. For experiments using cultured hippocampal neurons from PlxnB1−/− mice, littermates were dissociated side-by-side and plated on 24-well plates on top of a glia feeder layer. After genotyping, neurons that had been isolated from PlxnB1−/− and wildtype pups were used in experiments.

For time-lapse imaging, rat neurons were grown at 400,000 neurons/35-mm dish coated with poly-D-lysine (20 µg/ml) and laminin (3.4 µg/ml). These neurons were grown without a glia feeder layer and therefore, were not treated with AraC.

Hippocampal organotypic slices were harvested from P6 rat pups (Hayashi et al., "The Postsynaptic Density Proteins Homer and Shank Form a Polymeric Network Structure," *Cell*, 137:159-171 (2009), which is hereby incorporated by reference in its entirety) and cut on a tissue chopper 380 µm thick then placed on cell culture inserts (0.4 µm pore size, Millipore) and incubated in slice culture media for 7 days in vitro (DIV) at 35° C., 5% $CO_2$. Beginning at 2 DIV slices were treated with TTX (1 µM) in slice culture medium or with slice culture medium alone (control). Cutting solution (mM): 4 KCl, 1 $CaCl_2$, 8 $MgCl_2$, 26 $NHCO_3$, 200 Sucrose, 30 D-glucose, 25 HEPES free acid, 320 mOsm, oxygenated. Slice Culture Medium in MEM salts powder+glutamine (Invitrogen) (mM): 25 HEPES free acid, 26 $NaHCO_3$, 30 D-glucose, 0.5 L-ascorbate, 2 $MgSO_4$, 2 Glutamax, 0.2 $CaCl_2$, 1 µg/ml insulin (Sigma), 20% horse serum (Gibco), 320 mOsm, pH 7.2.

Example 3—Sema4D Treatments

Neurons were treated for varying amounts of time (Example 7) w either Sema4D-Fc (R&D Systems) or Fc (R&D Systems) and later assayed for synaptic phenotypes (1 nM treatments) or for growth cone collapse (10 nM). EphrinA1-Fc (43 nM, R&D Systems) (Richter et al., "The EphA4 Receptor Regulates Neuronal Morphology Through SPAR-Mediated Inactivation of Rap GTPases," *J. Neurosci.*, 27:14205-14215 (2007), which is hereby incorporated by reference in its entirety) was used as a positive control in the growth cone collapse assays. For the Sema4D-AP experiments, an N-terminal translational fusion of Sema4D with alkaline phosphatase (gift of Alain Chedotal) (Flanagan et al., "Alkaline Phosphatase Fusions of Ligands or Receptors as In Situ Probes for Staining of Cells, Tissues, and Embryos," *Methods Enzymol.*, 327:19-35 (2000); Flanagan et al., "The Kit Ligand: A Cell Surface Molecule Altered in Steel Mutant Fibroblasts," *Cell*, 63:185-194 (1990), which are hereby incorporated by reference in their entirety) or the empty AP5 vector (1 nM) was used. The alkaline phosphatase constructs were transfected by calcium phosphate transfection (Xia et al., "Calcium Influx Via the NMDA Receptor Induces Immediate Early Gene Transcription by a MAP Kinase/ERK-Dependent Mechanism," *J. Neurosci.*, 16:5425-5436 (1996), which is hereby incorporated by reference in its entirety) into HEK 293T cells and allowed to be expressed for 3-5 days. The Sema4D-AP and AP only were secreted from the cells and the media was harvested and concentrated with Centricon filters (Milipore, 0.4 µm pore size) and the concentration was determined via a colorimetric reaction (Flanagan et al., "Alkaline Phosphatase Fusions of Ligands or Receptors as In Situ Probes for Staining of Cells, Tissues, and Embryos," *Methods Enzymol.*, 327:19-35 (2000), which is hereby incorporated by reference in its entirety). To do this, concentrated HEK293T media (1%) was added to lysis buffer and 2×SEAP buffer and OD 405 nm was measured at 0 and 60 seconds. Concentration=$(OD_{60}-OD_0)/0.04 \times 100(9.3 \times 10^{-12})$. AP constructs were then bath applied to neurons for experiments (1 nM Sema4D-AP). Lysis Buffer: 1% TritonX-100, 10 mM Tris-HCl (pH8) 2×SEAP: 2M diethanolamine (pH 9.8), 1 mM MgCl2, 20 mM L-homoarginine, 40.6 mM p-nitrophenylphosphate, 10% BSA.

Example 4—Growth Cone Collapse Assay

Neurons were cultured without an astrocyte feeder layer on 35-mm dishes and transfected with green fluorescent protein (CEP) at 1 DIV by calcium phosphate transfection. Neurons were then treated with Sema4D-Fc (10 nM), Fc alone (10 nM), or EphrinA1-Fc (R&D Systems, 2 µg/ml) (Richter et al., "The EphA4 Receptor Regulates Neuronal Morphology Through SPAR-Mediated Inactivation of Rap GTPases," *J. Neurosci.*, 27:14205-14215 (2007), which is hereby incorporated by reference in its entirety) for 1.5 h at 37° C. EphrinA1-Fc was preclustered with an anti-Fc antibody (α-IgG-AP, Jackson Immuno, 1:4 IgG:EphrinA1-Fc) for 1 hour prior to treatment of neurons as is commonly done for this molecule (Richter et al., "The EphA4 Receptor Regulates Neuronal Morphology Through SPAR-Mediated Inactivation of Rap GTPases," *J. Neurosci.*, 27:14205-14215 (2007), which is hereby incorporated by reference in its entirety). Neurons were imaged on an inverted microscope (Olympus IX70, 60× oil immersion objective) using Volocity image acquisition software; images were acquired as a z-stack with a 0.5 µm step size. Growth cones were considered collapsed if they did not contain filopodial extensions and visible lamellipodia.

Example 5—Immunostaining

Neurons were fixed and stained for synaptic markers at 11 DIV. Neuronal media was replaced with 1×PBS and neurons were then fixed with 4% paraformaldehyde/4% sucrose for 8 min at room temperature. Coverslips were then washed three times with 1×PBS for 5 minutes each and incubated overnight at 4° C. in a humidified chamber with primary antibody. All antibody dilutions were prepared in 1×GDB (0.1% gelatin, 0.3% TritonX-100, 4.2% 0.4M phosphate buffer, and 9% 5 M NaCl). After overnight incubation, coverslips were washed three times with 1×PBS for 5 minutes each and then incubated with appropriate Cy3- and Cy5-conjugated secondary antibodies (1:500 each; Jackson ImmunoResearch Laboratories) in 1×GDB for 2 hours at room temperature. Coverslips were then washed three times with 1×PBS for 10 minutes each, dipped in $dH_2O$, and mounted on glass slides with Aquamount (Lerner Laboratories). The following antibodies were used: mouse (ms) α-GAD65 (1:1000, lipore), rabbit (rb) α-GA $BA_4R$ γ2 (1:100, Millipore), ms α-Gephyrin (1:500, Synaptic Systems), rb α-Synapsin I (1:1000, Millipore), ms α-GluA2 (1:500, NeuroMab), ms α-MAP2 (1:1000, Sigma), α-ms 488 (1:1000, Invitrogen), α-ms Cy3 (1:500, Jackson Immuno), α-rb Cy5 (1:500, JacksonImmuno).

Example 6—Live Imaging

Cells were plated on 35-mm dishes and transfected with GFP-Gephyrin (gift of M. Kneussel) (Maas et al., "Neuronal Cotransport of Glycine Receptor and the Scaffold Protein Gephyrin," *J. Cell Biol.*, 172:441-451 (2006), which is hereby incorporated by reference in its entirety) at 2 DIV. At 8 DIV, neurons were imaged with a spinning disc confocal (3i Marianas spinning disk confocal system with Yokogawa CSU-X1 confocal head mounted on ZeissAxio-observer inverted microscope, 63× oil objective). Images were acquired every 15 seconds for 10 minutes prior to treatment with either Sema4D-Fc (1 nM) or Fc control (1 nM, Fc only) then imaged again after treatment for 30 minutes (15 seconds image interval). Neurons were imaged on a stage heater (~33° C., QE-1 Warner Instruments) in HEPES buffered imaging solution (mM: 117 NaCl, 5.3 KCl, 1.8 $CaCl_2$, 0.814 $MgSO_4$, 1 $NaH_7PO_4$, 20 HEPES, 50 D-glucose, 0.1% BSA, 320 mOsm, pH 7.2); (Wierenga et al., "Postsynaptic Expression of Homeostatic Plasticity at Neocortical Synapses," *J.*

Neurosci., 25:2895-2905 (2005), which is hereby incorporated by reference in its entirety) using SlideBook acquisition software to acquire z-stack images (0.5 µm step size). For analysis, time-lapse imaging series were broken into 10-minute increments. Images were exported and registered to eliminate any shifting that occurred over time (StackReg, ImageJ plugin). Dendrites were then traced and kymographs were made (MultipleKymograph, ImageJ plugin) for all dendrites in each condition. Although kymographs were used to analyze the movement of every GFP-Gephyrin puncta in each neuron, any movement observed in the kymograph was subsequently characterized in the raw time-lapse images. Only those movements that were consistent between the kymograph and the image series were analyzed. Using this program, each GFP-Gephyrin puncta was followed across the time-lapse series. GFP-Gephyrin puncta dynamics were broken down into two different categories. In the first, the instantaneous velocity of each puncta was quantified. This is defined as the velocity from one frame to the next. Any change in direction of movement or velocity was recorded. For example, in the right panel of FIG. 6B the moving puncta at 10', the puncta splits from the original puncta by moving to the left (retrograde track 1) then pauses and then continues moving to the left (retrograde track 2). The instantaneous velocity was measured once per continuous movement. Additionally, the duration (seconds) and the distance (µm) of each continuous movement, defined as the distance and time that the puncta moves without changing direction or velocity, was determined. The average of all puncta in each condition at each time point was calculated. The average total distance each puncta moved during a 10-minute time-lapse series was also quantified. In addition to quantifying the movement characteristics of the GFP-Gephyrin puncta, the percent of stable vs. mobile puncta were recorded in each neuron. Quantifications are presented in Table 1 as follows:

TABLE 1

GFP-Gephyrin puncta dynamics after 10 minutes Sema4D-Fc or Fc control treatment (1 nM).

|  | Fc control | Sema4D |
| --- | --- | --- |
| % Stable | 0.945 +/− 0.19 | 0.934 +/− 0.019 |
| Instantaneous Velocity (µm/min) | 1.005 +/− 0.06 | 0.925 +/− .18 |
| Average Track Distance (µm) | 0.752 +/− 0.07 | 0.897 +/− 0.16 |
| Average Track Duration (s) | 59.464 +/− 4.76 | 74.498 +/− 14.09 |
| Average Puncta Total Distance (µm) | 2.090 +/− 1.07 | 2.078 +/− 0.47 |
| Average Puncta Total Duration (s) | 141.016 +/− 54.38 | 186.045 +/− 24.55 |

Example 7—Electrophysiology: Cultured Neurons

Whole-cell voltage clamp recordings were obtained from primary hippocampal cultured neurons at 11 DIV. Neurons were first treated with Fc control (Fc construct alone) or Sema4D-Fc at 1 nM for 0.5, 1, 2, or 4 hours by removing the existing media and replacing with 0.5 mL fresh media plus Fc alone or Sema4D-Fc. Following treatment, glass coverslips were transferred to a recording chamber attached to an Olympus upright microscope with continual perfusion of ACSF (95% $O_2$:5% $CO_2$) containing (in mM): 125 NaCl, 26 $NaHCO_3$, 2.3 KCl, 1.26 $KH_2PO_4$, 2 $CaCl_2$, 2 $MgSO_4$, 10 glucose, and 1 nM Fc or Sema4D-Fc (pH 7.4) maintained at 32° C. Separate holding reservoirs and tubing were used to avoid any cross contamination between Fc and Sema4D-Fc treatments and perfused with a peristaltic pump. Measures of mIPSCs were done in the presence of 1 nM tetrodotoxin (TTX; Abcam Biochemicals), 5 µM DL-2-Amino-5-phosphonopentanoic acid (APV; Sigma Aldrich), and 10 µM 6,7-Dinitroquinoxaline-2,3(1H,4H)-dione (DNQX; Sigma Aldrich) to isolate inhibitory postsynaptic currents. Patch pipettes (3-5 MΩ) were filled with intracellular solution containing (in mM) 120 CsCl, 10 HEPES, 1 EGTA, 0.1 $CaCl_2$, 1.5 $MgCl_2$, 4 $Na_2ATP$, and 0.3 $Na_2GTP$ (pH 7.3, adjusted with CsOH). A Multiclamp700B amplifier and a Digidata 1440A digitizer controlled by pClamp10 software were used for recordings. $R_s$ and $R_{IN}$ were monitored throughout experiments using Lab Bench (Clampex 10.2) and changes of more than 30% throughout the course of the recording were discarded. To record mIPSCs, the membrane potential was held at −70 mV and events were filtered at 1 kHz. Data was recorded in 3 epochs at 100 seconds each for a total duration of 300 seconds per cell. mIPSCs were then evaluated offline in Clampfit 10.2 (Molecular Devices).

Example 8—Acute Hippocampal Slice

Wildtype or PlxnB1−/− mice (P11-12) were anesthetized with isoflurane, decapitated, and the brains removed with the head immersed in ice-cold, choline-based cutting solution, according to the animal protocol approved by Brandeis University IACUC. The choline cutting solution contained (mM) 25 NaHCO3, 1.25 NaH2PO4.H2O, 2.5 KCl, MgCl2.6H2O, 25 glucose, 0.5 CaCl2, 110 C5H14ClNO, 11.6 ascorbic acid, and 3.1 pyruvic acid. Coronal slices (300 µm) were cut from the posterior to anterior hippocampus. Slices were moved to a recovery chamber for 40 minutes at 36° C. After recovery, slices were moved to room temperature and placed in a separate holding chamber containing either 1 nM Fc or Sema4D-Fc for 1.5 hours prior to recordings. Following incubation, acute hippocampal slices were then transferred to the recording chamber at 34° C. and perfused with ACSF as described above. Whole-cell recordings were made from visually identified CA1 pyramidal neurons and measures of mIPSCs were performed as described above (cultured neurons).

Example 9—Organotypic Slice Cultures

Hippocampal organotypic slice cultures (control or TTX treated) were transferred to the recording chamber continuously perfused with aerated ACSF containing 1 nM Fc or Sema4D-Fc. Culture slices were incubated at 27° C. for 30 minutes during TTX washout to prevent excitotoxicity, and then recovered at 32° C. for 1.5 hours. Whole-cell patch clamp recordings were performed in current clamp to measure action potential firing with a set of step pulses from −50 to +100 pA in 25 pA increments from rest. Voltage monitoring of spontaneous activity was performed on cells with resting membrane potentials <−50 mV for a duration of 100 s. Voltage monitoring allowed confirmation of the presence of spontaneous epileptic activity in TTX-treated slices. Spontaneous excitatory and inhibitory postsynaptic currents (sEPSCs and sIPSCs, respectively) were recorded in the same cells by voltage-clamping the membrane potential at the reversal potential of one of the two postsynaptic currents (−65 to −55 mV for GABAergic and 5 to 15 mV for glutamatergic currents), measured independently in each cell by clamping the membrane in 5 mV increments. The intracellular solution for spontaneous events contained (mM): 120 CsMe, 10 KCl, 2 $MgSO_4$, 10 HEPES, 0.5 EGTA, 3 ATP, 0.3 GTP, 10 Phosphocreatine, 1 QX-314. Only experiments where TTX treatment resulted in increased spontaneous activity compared to control were used.

Example 10—Data Analysis and Statistics: Imaging/Analysis for Fixed Cell Experiments Image acquisition and quantification were performed in a blinded manner. Twelve-bit images of neurons were acquired on an Olympus Fluoview300 confocal microscope using a 60× objective. Within each experiment, images were acquired with identical settings for laser power, detector gain, and amplifier offset. Images were acquired as a z-stack (8-13 optical sections and 0.5 µm step size), and maximum intensity projections were created from the stacks (Image J).

For synapse density experiments, synapse density was quantified as the overlap of MAP2, the presynaptic antibody and the postsynaptic antibody using MetaMorph image analysis software. For each experiment, the threshold for the Cy3 and Cy5 channels was determined visually using three images of control neurons. The threshold was chosen such that all punctate structures would be included in the analysis. This threshold was then applied across all images within the experiment. The threshold for MAP2 was determined independently for each image. A binary mask including all pixels above the threshold was created for all channels for each image. The cell body was then manually deleted from the MAP2 mask. The "logical and" function was used to determine regions of triple co-localization at least one pixel in size. To calculate synapse density, this number was divided by the area of the neuron as measured using the MAP2 mask minus the cell body. Approximately 10-30 images from at least two separate coverslips were acquired and analyzed for each condition within an experiment for a total of three experiments.

For experiments analyzing the synapse density on somas of cultured neurons, images were processed similarly to those used in dendrite analysis, except instead of the morphology of the cell being determined by automated detection of MAP2 fluorescence, the soma was defined by a region of interest (ROI) manually drawn around the cell soma. This was necessary because the inner regions of the soma were often devoid of MAP2 immunostaining, therefore the outer edges defined the region of the soma. Synapses were counted within this ROI. Here, the "logical and" function was used to determine regions of colocalization of at least one pixel in size between the Cy3 and Cy5 channel (pre and postsynaptic makers). Synapse density was calculated as this number divided by the area of the ROI. Only non-GAD65 immunopositive neurons were used for the soma analysis as GAD65 exhibits both punctate and non-punctate staining in the soma (i.e., GABAergic interneurons were excluded from this analysis).

Synapse density values within each experiment were normalized to account for the variation in antibody staining and neuronal density from experiment to experiment, before combining data from separate experiments. Within an experiment, the average synapse density value was obtained for the control and for experimental conditions. The normalized value of each experiment is the experimental average value divided by the control average value. See Paradis et al., "An RNAi-Based Approach Identifies Molecules Required for Glutamatergic and GABAergic Synapse Development," Neuron., 53:217-232 (2007), which is hereby incorporated by reference in its entirety, for details of this conversion. Statistical analysis was performed comparing each experimental condition to control on the combined raw data from all experiments using SPSS Software to run a two-way between-effect ANOVA (factors were transfection group, and date of experiment), followed by Tukey's post hoc test for significance. Error bars denote standard error.

Example 11—Electrophysiology Data Analysis

The frequency and amplitude of mIPSCs was measured using a template generated in Clampfit 10.2 by selecting 50 random mIPSC events. Only single event mIPSCs with a stable baseline, sharp rise phase, and exponential decay were chosen. Double and multiple peak mIPSCs were excluded. Spontaneous EPSCs and IPSCs were measured using the threshold search function in Clampfit 10.2 measuring the area of all negative or positive going events from baseline with a noise rejection of 2 ms. All data are plotted as mean±S.E.M. Significance was determined with SPSS Statistics 19 (IBM; Armonk, N.Y.) with a one-way ANOVA to determine significance between conditions plotted on the x-axis, followed by a student's t-Test to determine significance between Fc control and Sema4D treatment for each condition. Cumulative distribution plots were created in Excel using 100 to 500 randomly selected points for each cell and significance was determined based on a two-sample Kolmogorov-Smirnov test.

Example 12—Representative Sema4D and PlexinB1 Nucleic Acid and Polypeptide Sequences The methods and compositions of the present disclosure can use well-known Sema4D and PlexinB1 gene sequences or fragments thereof, as well as gene products of the Sema4D and PlexinB1 gene sequences, e.g., polypeptides and antibodies which specifically bind to such gene products, or fragments thereof, as starting points for generating mutants. Sequences, splice variants, and structures of Sema4D and PlexinB1 gene sequences and gene products have been described in the art and examples of suitable gene sequences and gene products are described herein. See also, for example, the Gene Cards.com website available on the World Wide Web at genecards.org/cgi-bin/carddisp.pl?gene=SEMA4D and genecards.org/cgi-bin/carddisp.pl?gene=PLXNB1&search=plexinb1.

Example 13—The Extracellular Domain of Sema4D Promotes the Rapid Formation of GABAergic Synapses In order to determine whether Sema4D is sufficient to promote GABAergic synapse formation, 11 day in vitro (DIV) cultured rat hippocampal neurons were treated with the extracellular domain of mouse Sema4D [amino acids 24-711] conjugated to the Fc region of mouse $IgG_{2A}$ or Fc control for 0.5, 1, 2, and 4 hours. Neurons were subsequently fixed and immunostained against Microtubule Associated Protein 2 (MAP2) to visualize dendrites and proteins that localize specifically to GABAergic synapses: the presynaptic protein Glutamic Acid Decarboxylase 65 (GAD65) and the postsynaptic γ2 subunit of the $GABA_A$ receptor ($GABA_A R\gamma2$). Next, synapse density in these neurons was quantified using confocal microscopy; synapse density was defined as the number of opposing $GAD65/GABA_A R\gamma2$ puncta. Since the hippocampal cultures are comprised of ~75% glutamatergic principal cells and ~25% GABAergic interneurons, the majority of synapses quantified are formed onto the dendrites of principal cells. Using this assay, it was found that 0.5 hours of Sema4D-Fc treatment led to a 50% increase in GABAergic synapse density that was also observed with 1, 2, and 4 hour treatments (FIG. 1A). The biological activity of the Sema4D-Fc protein was verified by demonstrating that it is capable of collapsing hippocampal growth cones (FIGS. 2A-C), as reported previously (Swiercz et al., "Plexin-B1 Directly Interacts with PDZ-RhoGEF/LARG to Regulate RhoA and Growth Cone Morphology," Neuron, 35:51-63 (2002), which is hereby incorporated by reference in its entirety).

Figure 3:
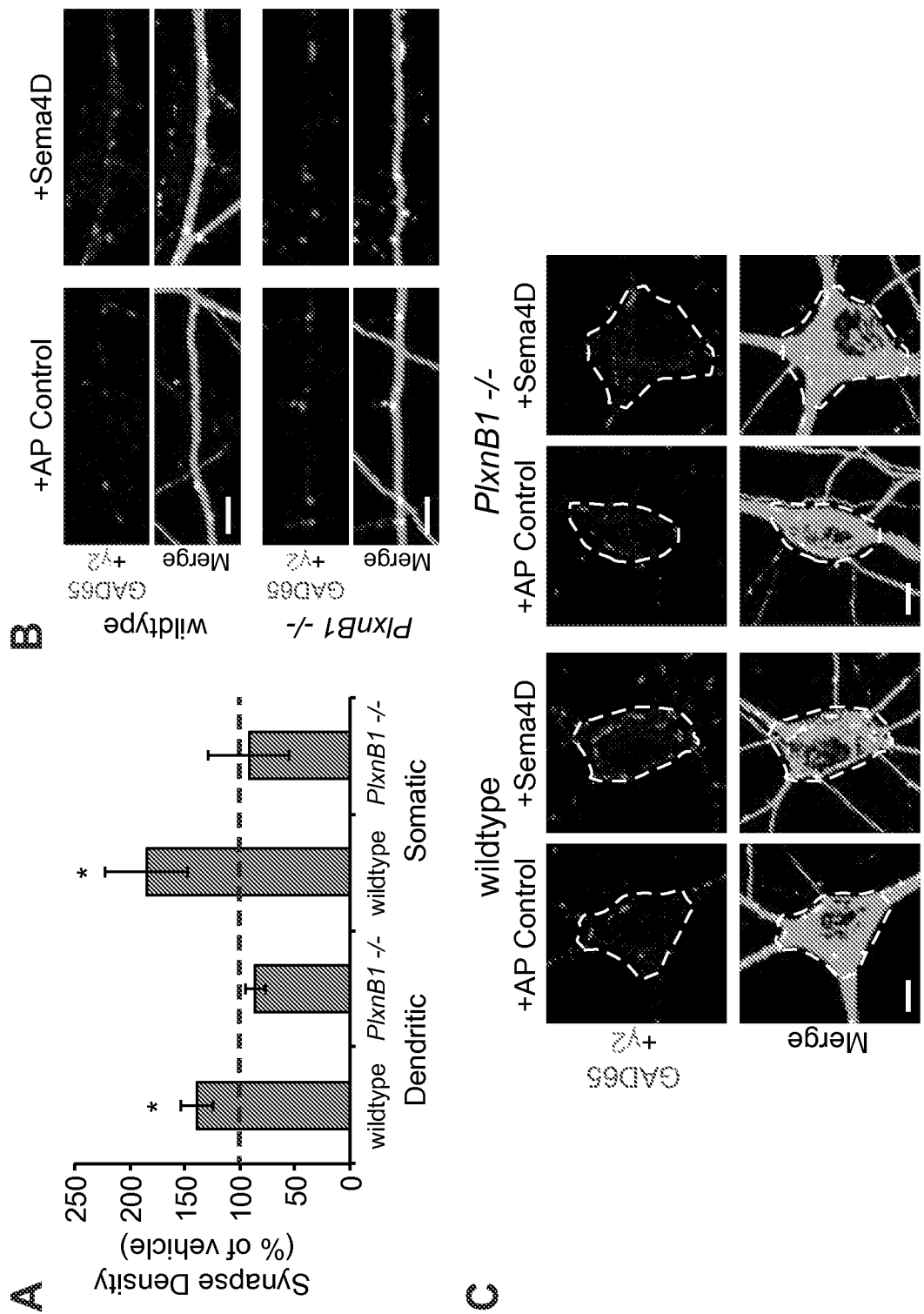
FIGS. 3A-C show the results of cultured hippocampal neurons isolated from PlxnB1−/− or wildtype control mice and treated with Sema4D-AP or alkaline phosphatase (AP) controls.

Further, a similarly rapid increase in GABAergic synapse density in response to Sema4D-Fc treatment was observed by immunostaining with antibodies that recognize a different set of synaptic proteins: Gephyrin, a postsynaptic scaffolding protein localized exclusively to inhibitory synapses (Fritschy et al., "Gephyrin: Where do we Stand, Where do we Go?" Trends Neurosci., 31:257-264 (2008); Sassoe-Pognetto et al., "Colocalization of Multiple GABA(A) Receptor Subtypes with Gephyrin at Postsynaptic Sites," J. Comp. Neurol., 420:481-498 (2000), which are hereby incorporated by reference in their entirety) and Synapsin I, a presynaptic vesicle associated protein (Cesca et al., "The Synapsins: Key Actors of Synapse Function and Plasticity," Prog. Neurobiol., 91:313-348 (2010), which is hereby incorporated by reference in its entirety) (FIG. 1B). It was also found that treatment with an entirely different source of Sema4D protein, the extracellular domain of Sema4D (amino acids 27 to 490) fused to the alkaline phosphatase enzyme (Sema4D-AP) secreted from HEK 293T cells, also drives a robust increase in GABAergic synapse density (FIG. 3A).

To determine if the specificity observed in our loss of function studies (Paradis et al., "An RNAi-Based Approach Identifies Molecules Required for Glutamatergic and GABAergic Synapse Development," Neuron., 53:217-232 (2007), which is hereby incorporated by reference in its entirety) would also be reflected in this gain of function approach, the exclusivity of Sema4D function in GABAergic synapse formation was revisited. To this end, it was determined whether the rapid action of Sema4D-Fc treatment affects excitatory synapse formation as well. Hippocampal cultures that had been treated with Sema4D-Fc or Fc control were immunostained with antibodies that specifically recognize a postsynaptic component of glutamatergic synapses, the postsynaptic glutamate receptor GluA2 and the presynaptic protein Synapsin I, to quantify glutamatergic synapse density (FIG. 1C). Sema4D-Fc treatment was observed to cause a small but significant decrease in excitatory synapse density at the 0.5 hour time point, while having no effect at subsequent time points (FIG. 1C). Without being bound by theory, it is believed that this transient decrease in excitatory synapse density is the result of the rapid assembly of GABAergic synapses in response to Sema4D-Fc treatment, which temporarily interferes with ongoing assembly of glutamatergic synapses. Overall, and consistent with loss of function studies, the addition of exogenous Sema4D-Fc to cultured hippocampal neurons does not drive glutamatergic synapse formation.

Different classes of interneurons synapse onto pyramidal cells at stereotyped locations: for example parvalbumin-positive fast-spiking interneurons synapse exclusively onto the perisomatic region of pyramidal cells (Kullmann et al., "Presynaptic, Extrasynaptic and Axonal GABAA Receptors in the CNS: Where and Why?" Prog. Biophys. Mol. Biol., 87:33-46 (2005) which is hereby incorporated by reference in its entirety). Therefore, it was determined whether Sema4D-AP treatment increased GABAergic synapse density at discrete locations on the postsynaptic neuron, which would indicate that Sema4D promotes GABAergic synapse formation between particular cell types. When analyzed separately, it was found that Sema4D-AP treatment caused an increase in GABAergic synapse density onto both the soma and dendrites of glutamatergic neurons (FIG. 3A-C; see "wildtype" dendritic and somatic panels). Thus, Sema4D is a synaptogenic factor that generally promotes GABAergic synapse formation between a variety of interneuron classes and principal cells.

The time course of functional GABAergic synapse formation in response to Sema4D-Fc treatment was also determined. Whole-cell voltage clamp recordings were performed to measure the frequency and amplitude of $GABA_A$ receptor-mediated miniature inhibitory post-synaptic currents (mIPSCs) (FIGS. 4A-D). A significant increase in the frequency of mIPSCs after both 2 and 4 hours of Sema4D-Fc treatment was observed (FIGS. 4B and 4D). This time frame indicates a model in which the arrival of synaptic components (as detected by immunocytochemistry—FIGS. 1A and 1B) precedes functionality at nascent GABAergic synapses (FIGS. 4A-D). Taken together, the data indicate that Sema4D signaling rapidly and simultaneously recruits scaffolding molecules, $GABA_ARs$, and presynaptic active zone components to form fully functional GABAergic synapses within 2 hours.

The analysis of GABAergic synaptic transmission also revealed a transient decrease in average mIPSC amplitude (~35%) at 0.5 hours followed by a transient increase in mIPSC amplitude (~50%) that is only detectable at 2 hours of Sema4D-Fc treatment (FIG. 4B, bottom). Without being bound by theory, it is believed that the transient decrease in mIPSC amplitude observed at 0.5 hours is due to recruitment of $GABA_ARs$ from pre-existing synapses to nascent synapses. Subsequently, as the neuron rapidly assembles more GABAergic synapses, a transient overshoot in receptor abundance occurs as evidenced by the increased mIPSC amplitude observed at 2 hours that is absent after 4 hours of Sema4D-Fc treatment.

Figure 2:
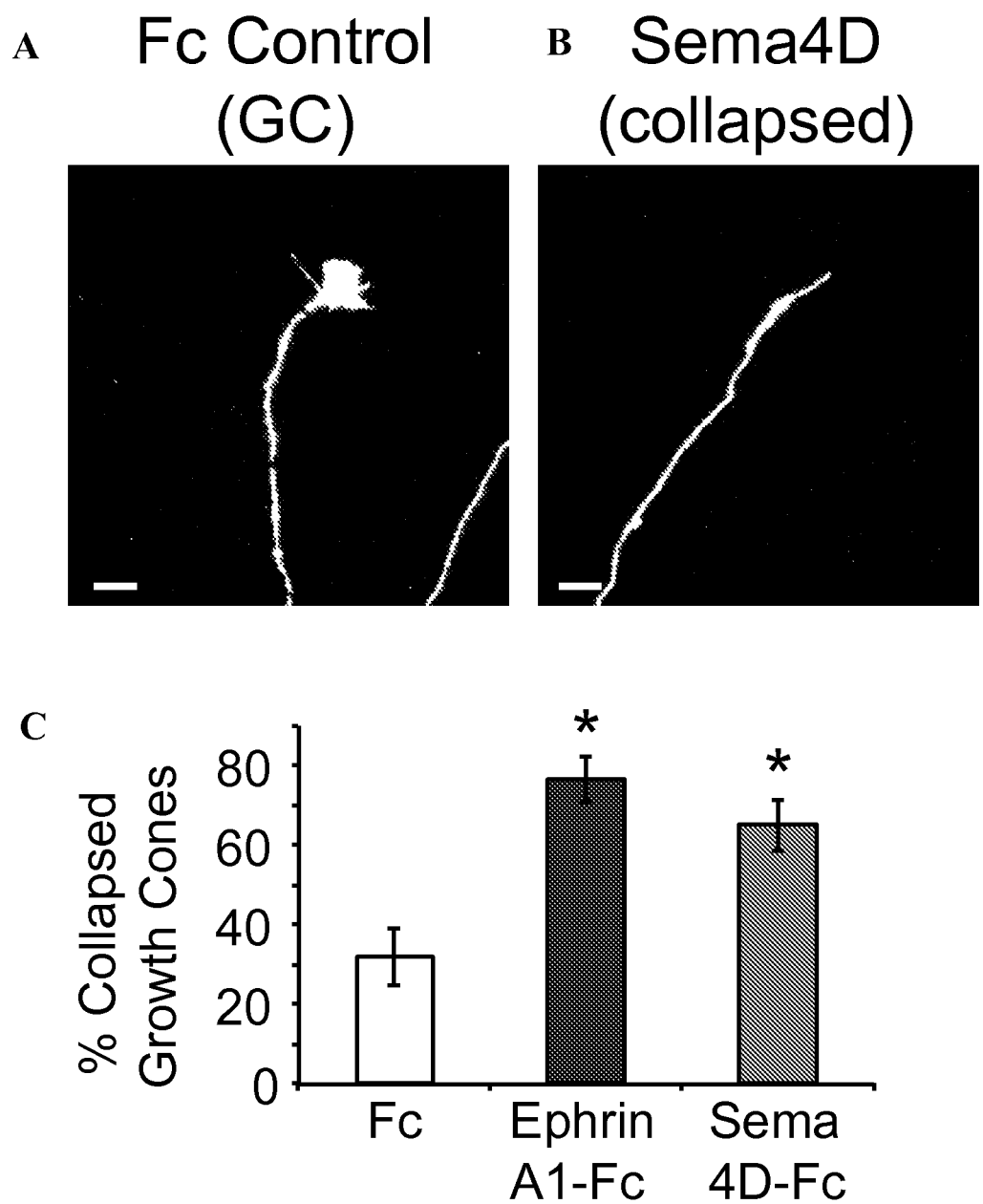
FIGS. 2A-C show representative images and quantified data of growth cones from cultured hippocampal neurons treated with Sema4D-Fc or Fc controls.
Figure 4:
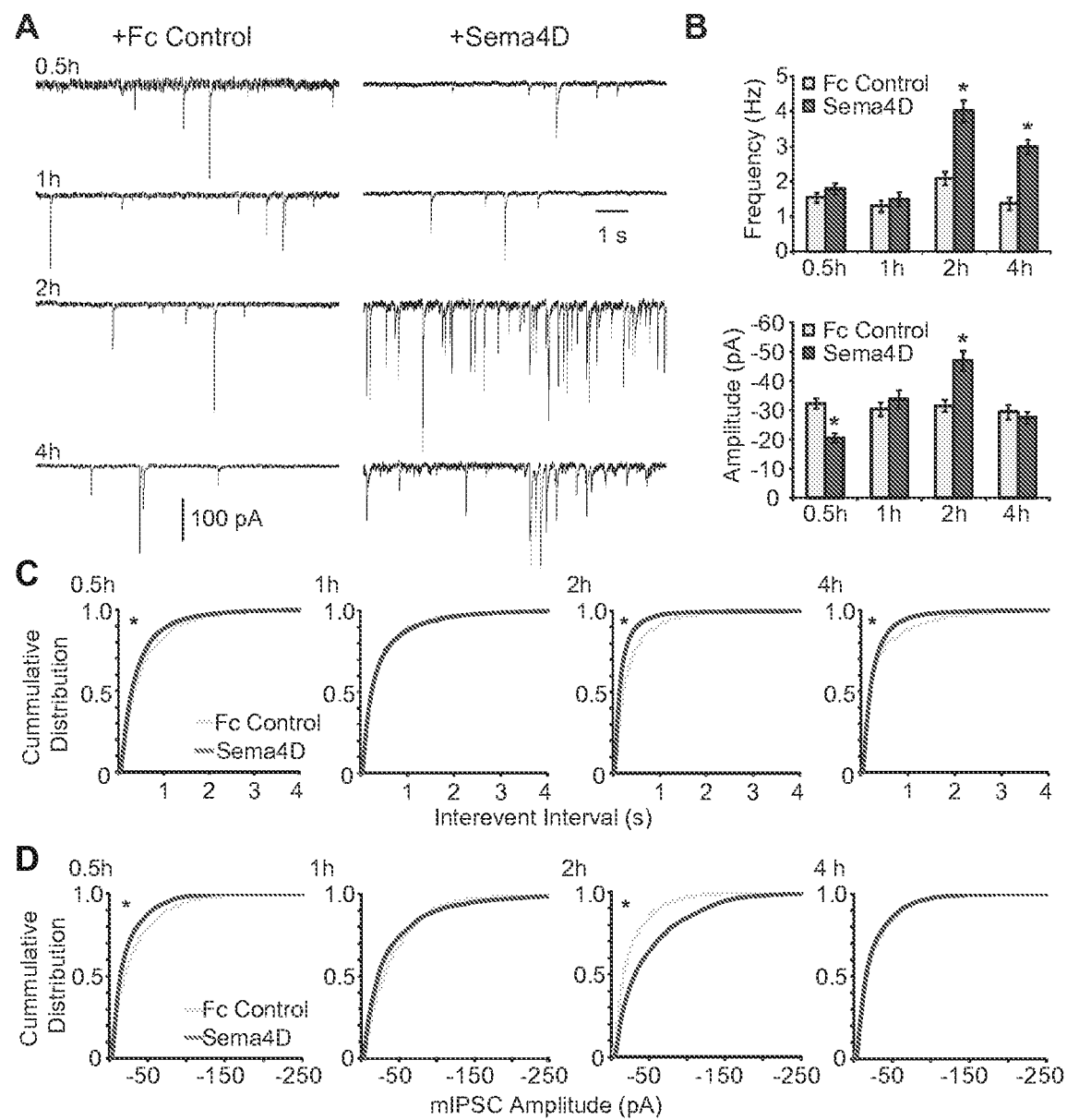
FIGS. 4A-D show the results of whole-cell voltage clamp recordings of miniature inhibitory post-synaptic currents (mIPSCs) from primary hippocampal neurons treated with Fc control or Sema4D-Fc.

Example 14—PlexinB1 is Necessary for the Effect of Sema4D on GABAergic Synaptogenesis in Cultured Neurons and Acute Hippocampal Slice PlexinB1 is a high affinity receptor for Sema4D (Maier et al., "Semaphorin 4C and 4G are Ligands of Plexin-B2 Required in Cerebellar Development," Mol. Cell Neurosci., 46:419-431 (2011); Tamagnone et al., "Plexins are a Large Family of Receptors for Transmembrane, Secreted, and GPI-Anchored Semaphorins in Vertebrates," Cell, 99:71-80 (1999), which are hereby incorporated by reference in their entirety) through which Sema4D signals in the nervous system to regulate growth cone collapse (Swiercz et al., "Plexin-B1 Directly Interacts with PDZ-RhoGEF/LARG to Regulate RhoA and Growth Cone Morphology," Neuron, 35:51-63 (2002), which is hereby incorporated by reference in its entirety). To confirm the biological relevance of the synaptogenic activity of Sema4D-Fc, it was determined whether the effect was dependent on PlexinB1. Hippocampal neurons from PlxnB1−/− or wildtype littermates isolated from E16 mouse pups (Friedel et al., "Gene Targeting Using a Promoterless Gene Trap Vector ("Targeted Trapping") is an Efficient Method to Mutate a Large Fraction of Genes," Proc. Natl. Acad. Sci. U.S.A., 102:13188-13193 (2005), which is hereby incorporated by reference in its entirety) were cultured. Application of Sema4D-Fc at 11 DIV for 2 hours significantly increased synapse density onto wildtype neurons as measured by the overlap of anti-GAD65 and anti-GABA$_A$Ry2 puncta (FIGS. 5A and 5B), and as previously demonstrated in rat neuronal cultures (FIGS. 1 and 4). The ability of Sema4D-Fc treatment to drive GABAergic synapse formation was completely abolished in neuronal cultures isolated from the PlxnB1−/− mice (FIGS. 5A and 5B). To assess whether the interaction between Sema4D and PlexinB1 was required to promote a specific subset of GABAergic synapses onto pyramidal neurons, GABAergic synapse density onto either the dendritic arbor or the soma of PlxnB1−/− pyramidal neurons in response to Sema4D-AP treatment was analyzed (FIGS. 3A-C). It was found that the absence of PlexinB1 abrogated the Sema4D-dependent increase in GABAergic synapse density onto both the dendrites and soma (FIGS. 5A-G). Thus, Sema4D-PlexinB1 signaling generally promotes GABAergic synapse formation irrespective of subcellular location.

Next, it was determined whether Sema4D could rapidly promote GABAergic synapse formation in an intact circuit. Therefore, it was asked whether Sema4D-Fc treatment could promote functional GABAergic synapse formation in an acute hippocampal slice preparation and, if so, whether this effect is also dependent on PlexinB1. To address these questions, whole-cell voltage clamp recordings were performed to assay mIPSC frequency and amplitude from CA1 pyramidal neurons in acute hippocampal brain slices derived from either P11-P12 wildtype or PlxnB1−/− mice (FIGS. 5C-G). Upon 2 hours of Sema4D-Fc treatment, a significant increase in mIPSC frequency (FIGS. 5D and 5F) were observed with no change in mIPSC amplitude (FIGS. 5E and 5G) in wildtype hippocampal slices. Consistent with the dependence on PlexinB1 for Sema4D's effects in cultured neurons (FIGS. 5A and 5B), it was found that the ability of Sema4D-Fc treatment to promote functional GABAergic synapse formation in acute hippocampal slices was completely dependent on the expression of PlexinB1, as evidenced by the lack of increased mIPSC frequency in Sema4D-Fc treated slices derived from PlxnB1−/− mice (FIGS. 5D and 5E). Unexpectedly, it was observed that mIPSC amplitude was slightly but significantly decreased in recordings from CA1 neurons in acute slices isolated from PlxnB1−/− mice treated with Fc control compared to wildtype treated with Fc control (FIGS. 5E and 5G). The decreased mIPSC amplitude was rescued by Sema4D-Fc treatment (FIGS. 5E and 5G), indicating a Sema4D-dependent effect on mIPSC amplitude that is PlexinB1 independent.

Example 15—Time-Lapse Imaging Studies of Synapse Formation During Sema4D-Fc Treatment Reveal Increased Rate of Addition of Gephyrin Puncta Given the rapid nature of the Sema4D effect on GABAergic synapse formation, the step(s) in GABAergic synapse formation influenced by Sema4D signaling was next determined. The studies were initiated by imaging the dynamics of GFP-tagged Gephyrin protein. Gephyrin was chosen based on the observed increase in Gephyrin puncta density in response to Sema4D-Fc treatment (FIG. 1B), the critical role of Gephyrin in forming the postsynaptic specialization of GABAergic synapses (Dobie et al., "Inhibitory Synapse Dynamics: Coordinated Presynaptic and Postsynaptic Mobility and the Major Contribution of Recycled Vesicles to New Synapse Formation," *J. Neurosci.*, 31:10481-10493 (2011); Fritschy et al., "Gephyrin: Where do we Stand, Where do we Go?" *Trends Neurosci.*, 31:257-264 (2008); Kuzirian et al., "Emerging Themes in GABAergic Synapse Development," *Prog. Neurobiol.*, 95(1):68-87 (2011); Maas et al., "Neuronal Cotransport of Glycine Receptor and the Scaffold Protein Gephyrin," *J. Cell Biol.*, 172:441-451 (2006), which are hereby incorporated by reference in their entirety) and its previous use in time lapse imaging experiments (Dobie et al., "Inhibitory Synapse Dynamics: Coordinated Presynaptic and Postsynaptic Mobility and the Major Contribution of Recycled Vesicles to New Synapse Formation," *J. Neurosci.*, 31:10481-10493 (2011); Maas et al., "Neuronal Cotransport of Glycine Receptor and the Scaffold Protein Gephyrin," *J. Cell Biol.*, 172:441-451 (2006), which are hereby incorporated by reference in their entirety). Time-lapse imaging of cultured hippocampal neurons at 8 DIV that had been transfected with a GFP-Gephyrin construct at 2 DIV (Maas et al., "Neuronal Cotransport of Glycine Receptor and the Scaffold Protein Gephyrin," *J. Cell Biol.*, 172:441-451 (2006), which is hereby incorporated by reference in its entirety) were performed. Images were acquired every 15 seconds for 10 minutes prior to addition of either Fc control or Sema4D-Fc and every 15 seconds for 30 minutes (divided into 3 sets of 10 minute videos for analysis) immediately after Sema4D-Fc or Fc addition.

Figure 6:
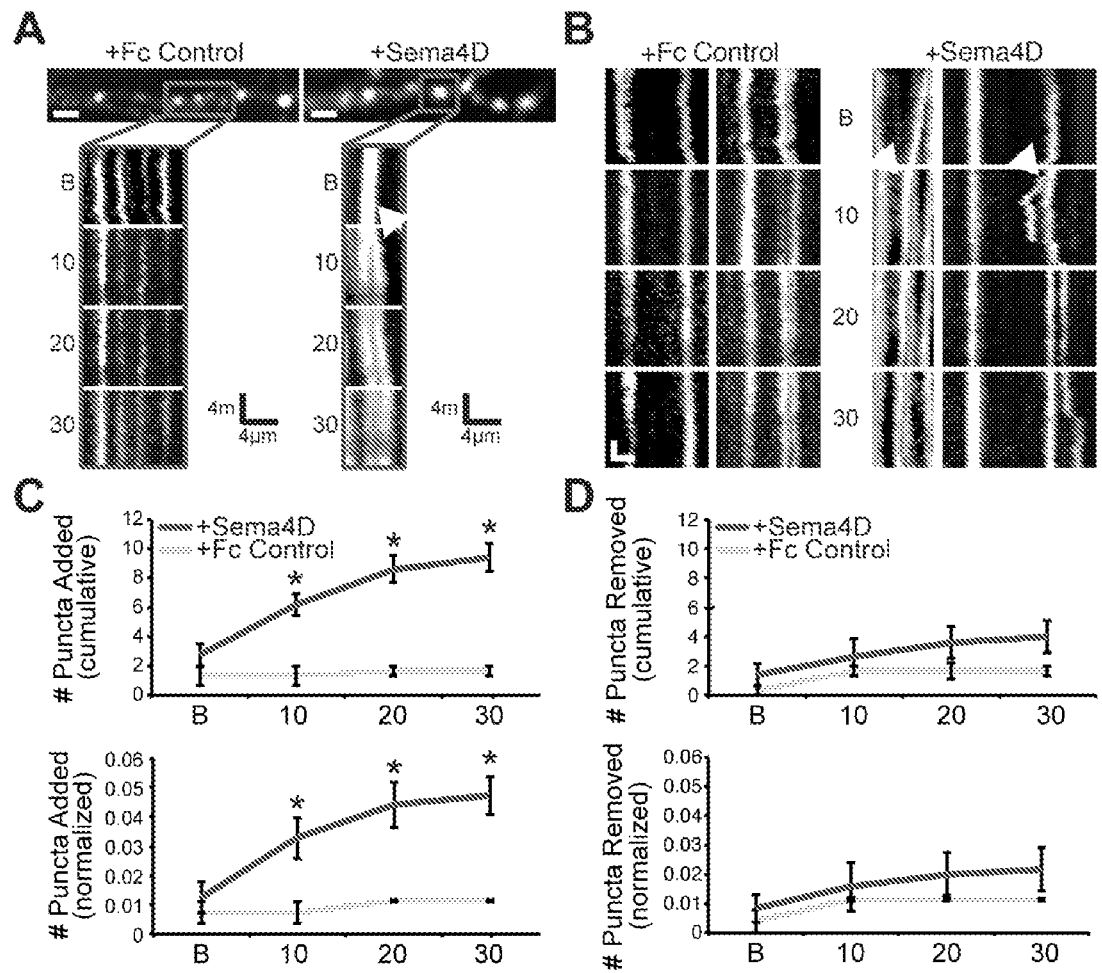
FIGS. 6A-D demonstrate that the application of soluble Sema4D-Fc leads to a rapid increase in the rate of GFP-Gephyrin addition in cultured hippocampal neurons.

To follow the behavior of each individual GFP-Gephyrin puncta over time (FIG. 6), kymographs of all imaged dendrites were constructed. A significant increase in the rate of addition of GFP-Gephyrin puncta after Sema4D-Fc treatment compared to Fc control was observed (FIGS. 6A-C). This increase occurred without a change in the number of GFP-Gephyrin puncta removed over the imaging session in Sema4D-Fc treated neurons compared to Fc control (FIG. 6D), indicating that there is a net increase in the number of GFP-Gephyrin puncta as opposed to simply an increase in the turnover rate of GFP-Gephyrin puncta. Notably, the vast majority of GFP-Gephyrin puncta additions or removals were the result of either splitting (95+/−2.9%) or merging (94.6+/−3.9%) of existing GFP-Gephyrin puncta (FIGS. 6A-B). "Splitting" has been observed previously during time-lapse imaging of inhibitory synapse development over the course of many hours in hippocampal neuronal cultures (Dobie et al., "Inhibitory Synapse Dynamics: Coordinated Presynaptic and Postsynaptic Mobility and the Major Contribution of Recycled Vesicles to New Synapse Formation," *J. Neurosci.*, 31:10481-10493 (2011), which is hereby incorporated by reference in its entirety).

It was next determined whether Sema4D-Fc treatment affects other aspects of GFP-Gephyrin dynamics over the 40 minute imaging session. To this end, the percentage of GFP-Gephyrin puncta that did not move over the imaging period (Table 1 "% Stable") was quantified and no difference in the percentage of stable puncta between Fc control and Sema4D-Fc treated neurons was found. The instantaneous velocity of GFP-Gephyrin puncta in Fc control versus Sema4D-Fc treatment was also determined and no differences between conditions were observed (Table 1). Similarly, the total distance and duration of puncta travel from the start to finish of the imaging period was quantified, as well as the average distance and duration of each individual puncta movement (Table 1), and, again, no differences were found. Thus, the major effect of Sema4D signaling is to drive the addition of new postsynaptic assemblies of scaffolding proteins by splitting pre-existing assemblies of these proteins.

Example 16—Sema4D-Fc Treatment Suppresses Network Hyperexcitability in an In Vitro Model of Epilepsy Since Sema4D rapidly and selectively drives GABAergic synapse formation, it was hypothesized that it could functionally restore inhibition in the context of enhanced excitability in a neural network. To explore the functional consequence of Sema4D-mediated synapse formation on network excitation, an in vitro model of epileptiform activity (Bausch et al., "Plasticity of Both Excitatory and Inhibitory Synapses is Associated with Seizures Induced by Removal of Chronic Blockade of Activity in Cultured Hippocampus," *J. of Neurophysiol.*, 96:2151-2167 (2006); Wong, "Epilepsy in a Dish: An In Vitro Model of Epileptogenesis," *Epilepsy Curr.*, 11:153-154 (2011), which are hereby incorporated by reference in their entirety) was used. Chronic treatment with tetrodotoxin (TTX) to block voltage-gated sodium channels can lead to synaptic homeostasis that subsequently promotes epileptic activity via an increase in network excitation following TTX removal (Turrigiano et al., "Activity-Dependent Scaling of Quantal Amplitude in Neocortical Neurons," *Nature*, 391(6670):892-896 (1998); Bausch et al., "Plasticity of Both Excitatory and Inhibitory Synapses is Associated with Seizures Induced by Removal of Chronic Blockade of Activity in Cultured Hippocampus," *J. of Neurophysiol.*, 96:2151-2167 (2006); Kim and Tsien, "Synapse-Specific Adaptations to Inactivity in Hippocampal Circuits Achieve Homeostatic Gain Control While Dampening Network Reverberation," *Neuron*, 58(6):925-937 (2008), which are hereby incorporated by reference in their entirety). Thus, hippocampal slices were cultured from P7 rat pups and chronically treated with TTX (1 µM) for 6-7 days, followed by a 30 minute TTX withdrawal period at 27° C. These slices are referred to as TTX-EA, for TTX-induced Epileptic Activity.

Immediately after TTX withdrawal, a significant and sustained (up to 6 hours following TTX removal) increase in activity in the form of spontaneous action potential firing was observed that was absent from untreated control slices (FIGS. 7A-B; compare untreated—Fc control to TTX-EA—Fc control; note different scale for y-axis untreated vs. TTX-EA in FIG. 7B). Importantly, this activity was not observed in slices that had been treated with Sema4D-Fc for just two hours after TTX withdrawal (FIGS. 7A-B; compare TTX-EA—Fc control to TTX-EA—Sema4D). A comparison between Fc control and Sema4D-Fc treated slices revealed a 90% reduction in average spike frequency in both untreated and TTX-EA slices (FIGS. 7A-B), indicating that Sema4D drives GABAergic synapse formation independent of the initial level of network activity.

To determine if reduced hyperexcitability following Sema4D-Fc treatment was the result of an increase in inhibitory synaptic transmission, spontaneous inhibitory and excitatory postsynaptic currents (sIPSCs and sEPSCs, respectively) were measured in the same cell (FIGS. 7C-D). Due to a high degree of event overlap, individual events were not measured. Rather, the total synaptic charge was calculated for both inhibitory and excitatory events by integrating the total area of the events from baseline over 100 seconds. Sema4D-Fc treatment significantly enhanced the total inhibitory synaptic charge in both untreated and TTX-EA slices (FIG. 7C). These results indicate that a Sema4D-dependent increase in inhibitory tone is sufficient to quench hyperexcitability. Additionally, there was a significant decrease in excitatory synaptic charge observed in the TTX-EA Sema4D-Fc-treated slices compared to TTX-EA Fc control slices that was not apparent in untreated control slices (FIG. 7D). This observation indicates that in the context of ongoing network hyperexcitability, the Sema4D-dependent increase in inhibition triggers additional compensatory network alterations, such that overall excitability is also reduced.

Figure 5:
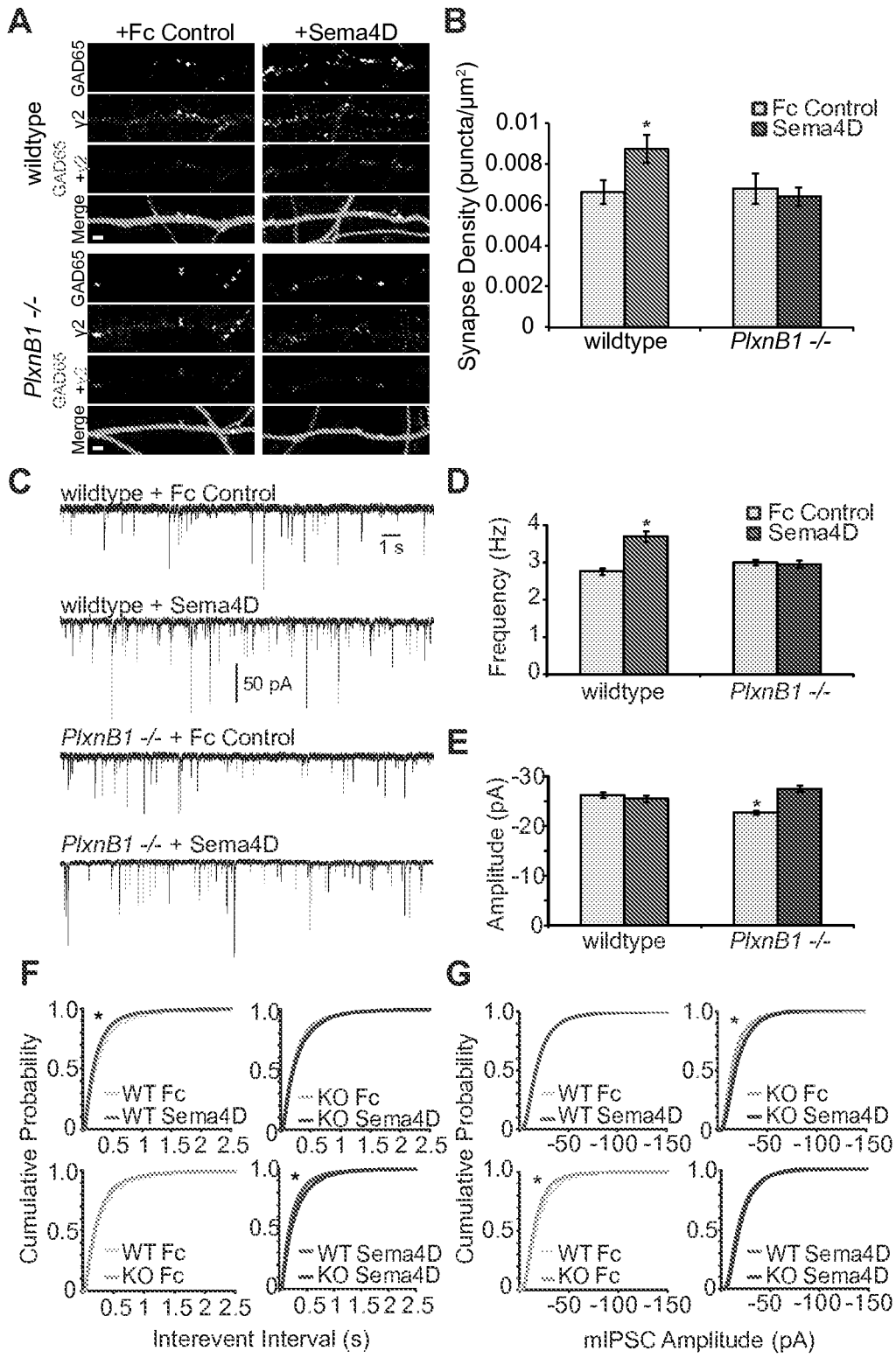
FIGS. 5A-G demonstrate that Sema4D drives GABAergic synapse formation in a PlexinB1-dependent manner.
Figure 7:
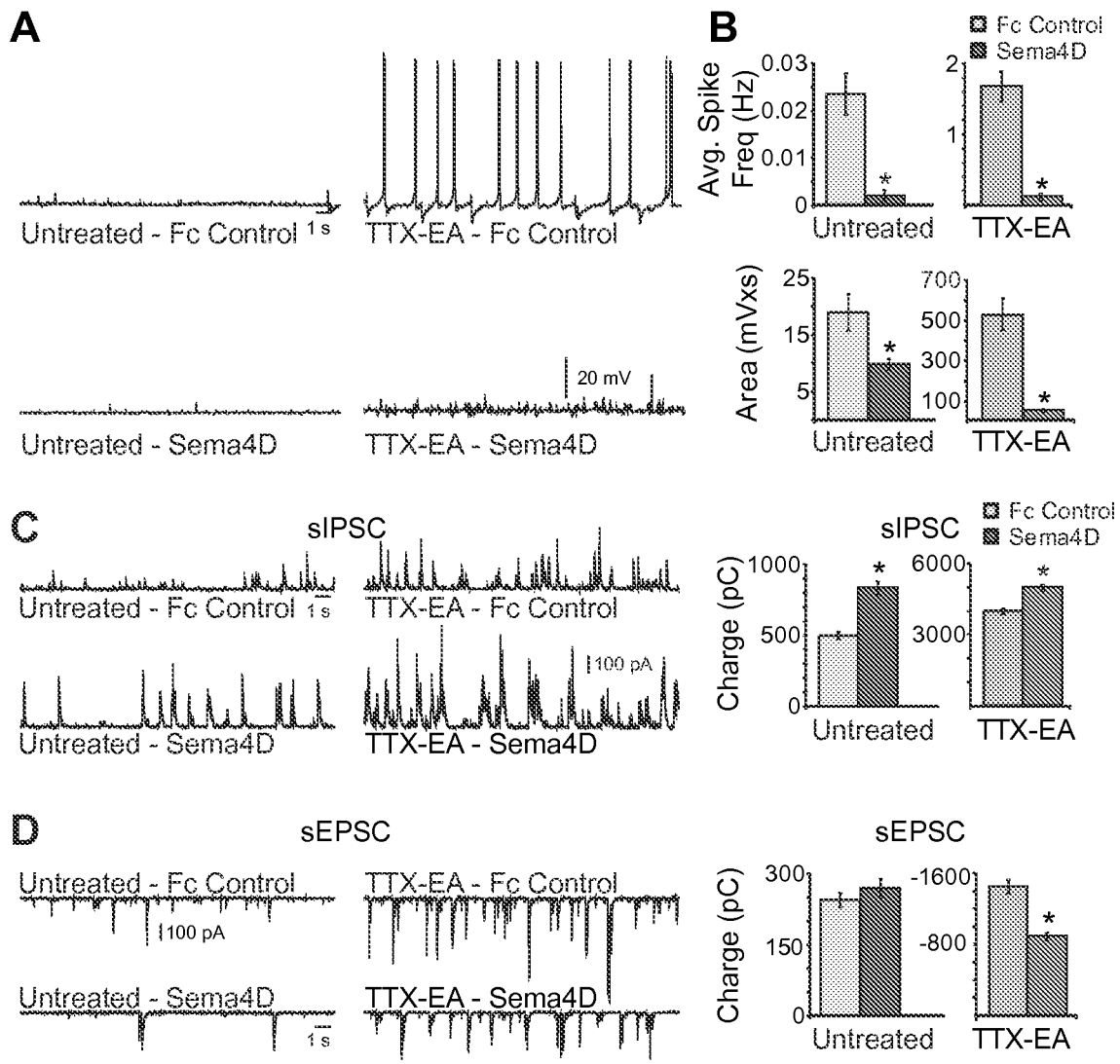
FIGS. 7A-D demonstrate that Sema4D treatment rapidly suppresses TTX-induced epileptic activity.

Based on the foregoing, it has been demonstrated that treatment of cultured hippocampal neurons or acute hippocampal slice with the extracellular domain of the protein Sema4D causes a rapid increase (i.e. within 0.5 to 2 hours) in the density of functional GABAergic synapses (FIGS. 1 and 4) in a PlexinB1-dependent manner (FIG. 5). Time-lapse live imaging studies of Sema4D-Fc treated neurons revealed an increased rate of GFP-Gephryin addition via splitting of pre-existing GFP-Gephyrin puncta within 10 minutes of Sema4D-Fc addition (FIG. 6). Further, using organotypic hippocampal slice culture as an in vitro model of epileptiform activity, it was demonstrated that acute Sema4D-Fc treatment rapidly and dramatically alters the hyperexcitability found in these slices in a manner consistent with a Sema4D-mediated increase in network inhibition (FIG. 7). While these studies are the first to characterize Semaphorin signaling in GABAergic synapse formation, a number of other studies have implicated other Semaphorin family members in glutamatergic synapse formation or elimination (Ding et al., "Semaphorin 3E-Plexin-D1 Signaling Controls Pathway-Specific Synapse Formation in the Striatum," *Nat. Neurosci.*, 15:215-223 (2012); Morita et al., "Regulation of Dendritic Branching and Spine Maturation by Semaphorin3A-Fyn Signaling," *J. Neurosci.*, 26:2971-2980 (2006); O'Connor et al., "Semaphorin 5B Mediates Synapse Elimination in Hippocampal Neurons," *Neural Dev.*, 4:18 (2009); Paradis et al., "An RNAi-Based Approach Identifies Molecules Required for Glutamatergic and GABAergic Synapse Development," *Neuron.*, 53:217-232 (2007); Sahay et al., "Secreted Semaphorins Modulate Synaptic Transmission in the Adult Hippocampus," *J. Neurosci.*, 25:3613-3620 (2005); Tran et al., "Secreted Semaphorins Control Spine Distribution and Morphogenesis in the Postnatal CNS," *Nature*, 462:1065-1069 (2009), which are hereby incorporated by reference in their entirety).

In addition to Sema4D, a handful of other secreted or transmembrane proteins affect GABAergic synapse formation and function including BDNF/TrkB (Chen et al., "TrkB (Tropomyosin-Related Kinase B) Controls the Assembly and Maintenance of GABAergic Synapses in the Cerebellar Cortex," *J. Neurosci.*, 31:2769-2780 (2011); Hong et al., "A Biological Function for the Neuronal Activity-Dependent Component of Bdnf Transcription in the Development of Cortical Inhibition," *Neuron*, 60:610-624 (2008); Rico et al., "TrkB Receptor Signaling is Required for Establishment of GABAergic Synapses in the Cerebellum," *Nat. Neurosci.*, 5:225-233 (2002), which are hereby incorporated by reference in their entirety), Neuroligin-2/β-Neurexin (Chubykin et al., "Activity-Dependent Validation of Excitatory Versus Inhibitory Synapses by Neuroligin-1 Versus Neuroligin-2," *Neuron*, 54:919-931 (2007); Gibson et al., "Neuroligin-2 Deletion Selectively Decreases Inhibitory Synaptic Transmission Originating from Fast-Spiking but not from somatostatin-Positive Interneurons," *J. Neurosci.*, 29:13883-13897 (2009); Varoqueaux et al., "Neuroligin 2 is Exclusively Localized to Inhibitory Synapses," *Eur. J. Cell Biol.*, 83:449-456 (2004), which are hereby incorporated by reference in their entirety), FGF7/FGFR2 (Terauchi et al., "Distinct FGFs Promote Differentiation of Excitatory and Inhibitory Synapses," *Nature*, 465:783-787 (2010), which is hereby incorporated by reference in its entirety), and Neuregulin 1/ErbB4 (Fazzari et al., "Control of Cortical GABA Circuitry Development by Nrg1 and ErbB4 Signalling," *Nature*, 464:1376-1380 (2010), which is hereby incorporated by reference in its entirety). Similarly to Sema4D, the ligands Neuroligin-2 and Neuregulin 1 both function in the postsynaptic neuron to mediate GABAergic synapse formation via an interaction with their cognate receptors, β-Neurexin and ErbB4 respectively, in presynaptic interneurons (Fazzari et al., "Control of Cortical GABA Circuitry Development by Nrg1 and ErbB4 Signalling," *Nature*, 464:1376-1380 (2010); Fu et al., "Differential Dynamics and Activity-Dependent Regulation of Alpha- and Beta-Neurexins at Developing GABAergic Synapses," *Proc. Natl. Acad. Sci. U.S.A.*, 107:22699-22704 (2010); Gibson et al., "Neuroligin-2 Deletion Selectively Decreases Inhibitory Synaptic Transmission Originating from Fast-Spiking but not from somatostatin-Positive Interneurons," *J. Neurosci.*, 29:13883-13897 (2009); Varoqueaux et al., "Neuroligin 2 is Exclusively Localized to Inhibitory Synapses," *Eur. J. Cell Biol.*, 83:449-456 (2004), which are hereby incorporated by reference in their entirety). The studies described herein are consistent with a model whereby Sema4D on the postsynaptic principal neuron engages PlexinB1 on the presynaptic inhibitory neuron. This interaction generates a trans-synaptic signal that regulates GABAergic synapse formation. In support of this model, Sema4D is expressed in the principal cells of the hippocampus during embryonic and postnatal development (Henry et al., "High-Resolution Gene Expression Atlases for Adult and Developing Mouse Brain and Spinal Cord," *Mammalian Genome*, 23:539-549 (2012); Lein et al., "Genome-Wide Atlas of Gene Expression in the Adult Mouse Brain," *Nature*, 445:168-176 (2007); Magdaleno et al., "BGEM: An In Situ Hybridization Database of Gene Expression in the Embryonic and Adult Mouse Nervous System," *PLoS Biol.*, 4:e86 (2006); Allen Developing Mouse Brain Atlas http://developingmouse.brainmap.org/, which are hereby incorporated by reference in their entirety) and is required in these postsynaptic neurons to mediate GABAergic synapse formation (Paradis et al., "An RNAi-Based Approach Identifies Molecules Required for Glutamatergic and GABAergic Synapse Development," *Neuron*, 53:217-232 (2007), which is hereby incorporated by reference in its entirety).

Another alternative is that Sema4D and PlexinB1 interact in cis in the postsynaptic neuron to promote synapse formation. An increasing number of studies demonstrate cis interactions between cell adhesion ligands and their receptors, including Semaphorin family members (Haklai-Topper et al., "Cis Interaction Between Semaphorin6A and Plexin-A4 Modulates the Repulsive Response to Sema6A," *EMBO J.*, 29:2635-2645 (2010); Taniguchi et al., "Silencing of Neuroligin Function by Postsynaptic Neurexins," *J. Neurosci.*, 27:2815-2824 (2007), which are hereby incorporated by reference in their entirety). However, the only described function of these cis interactions to date is inhibition of their cognate receptor-mediated signaling pathways (Yaron et al., "The Cis Side of Juxtacrine Signaling: A New Role in the Development of the Nervous System," *Trends Neurosci.*, 35:230-239 (2012), which is hereby incorporated by reference in its entirety). The data provided herein demonstrate that Sema4D-Fc treatment of cultured neurons causes splitting of GFP-Gephyrin puncta within 10 minutes of Sema4D-Fc addition, a time course that may be consistent with a role for PlexinB1 signaling in the postsynaptic neuron. Determination of the location of PlexinB1 expression, and the subcellular localization of the PlexinB1 protein, in the early postnatal hippocampus will aid in discriminating between these two models.

Accordingly, the action of Sema4D described here is the first report of GABAergic synapse formation on such a rapid time scale. The live imaging studies, where increased addition of GFP-Gephyrin puncta in response to 10 minutes of Sema4D-Fc treatment was observed, indicate that GABAergic synaptic components are poised and ready to respond to reception of a pro-synaptogenic signal. In support of this hypothesis, the increase in GFP-Gephyrin puncta observed in these studies occurs almost exclusively via splitting of existing GFP-Gephyrin puncta, a phenomenon that has also been observed during ongoing GABAergic synapse development (Dobie et al., "Inhibitory Synapse Dynamics: Coordinated Presynaptic and Postsynaptic Mobility and the Major Contribution of Recycled Vesicles to New Synapse Formation," *J. Neurosci.*, 31:10481-10493 (2011), which is hereby incorporated by reference in its entirety). This result indicates that addition of Sema4D triggers the action of the native GABAergic synapse formation machinery, consistent with loss of function studies that demonstrate a requirement for Sema4D for proper development of GABAergic synapses (Paradis et al., "An RNAi-Based Approach Identifies Molecules Required for Glutamatergic and GABAergic Synapse Development," *Neuron.*, 53:217-232 (2007), which is hereby incorporated by reference in its entirety). Other GABAergic synaptogenic factors mentioned above, such as FGF7, may have a previously unappreciated capacity for driving GABAergic synapse formation on a similarly rapid time scale as Sema4D.

The balance between excitatory and inhibitory inputs onto a given neuron regulates the overall activity of neuronal networks; disruptions to this balance can cause neurological disorders such as epilepsy (Ben-Ari, "Cell Death and Synaptic Reorganizations Produced by Seizures," *Epilepsia*, 42(Suppl 3): 5-7 (2001); Bernard et al., "Changes in Neuronal Excitability and Synaptic Function in a Chronic Model of Temporal Lobe Epilepsy," *Neurosci.*, 103:17-26 (2001); Cossart et al., "Dendritic but not Somatic GABAergic Inhibition is Decreased in Experimental Epilepsy," *Nat. Neurosci.*, 4:52-62 (2001); Fernandez et al., "Over-Inhibition: A Model for Developmental Intellectual Disability," *Trends Neurosci.*, 30:497-503 (2007); McNamara et al., "Molecular Signaling Mechanisms Underlying Epileptogenesis," *Sci. STKE*, 2006:re12 (2006), which are hereby incorporated by reference in their entirety). While the underlying mechanisms of epileptogenesis are largely unknown, recurrent seizures emerge when there is an aberrant increase in network activity. One antiepilepsy treatment would be to restore normal network activity by increasing inhibition through the formation of new GABAergic synapses. This type of treatment could be particularly useful in the developing nervous system, such as in children with infantile spasms, who have a significant risk of going on to develop epilepsy as adults (Paciorkowski et al., "Genetic and Biologic Classification of Infantile Spasms," *Ped. Neurol.*, 45:355-367 (2011), which is hereby incorporated by reference in its entirety). In this circumstance, building new GABAergic synapses in the developing brain could halt the progression to runaway excitation and turn the network back to a normal physiological range. In support of this model, a recent study demonstrated that intracerebral infusion of Neuregulin 1 acted as an anti-epileptic agent in a mouse kindling model of limbic epilepsy (Tan et al., "Neuregulin 1 Represses Limbic Epileptogenesis Through ErbB4 in Parvalbumin-Expressing Interneurons," *Nat. Neurosci.*, 15:258-

266 (2012), which is hereby incorporated by reference in its entirety). Based on the results described herein, it is believed that the ability of Sema4D to quickly increase inhibition in neural circuits via addition of new GABAergic synapses could represent just such an approach to the treatment of epilepsy: one which may be able to halt the progression of the disorder as opposed to merely symptomatic treatment.

Figure 8:
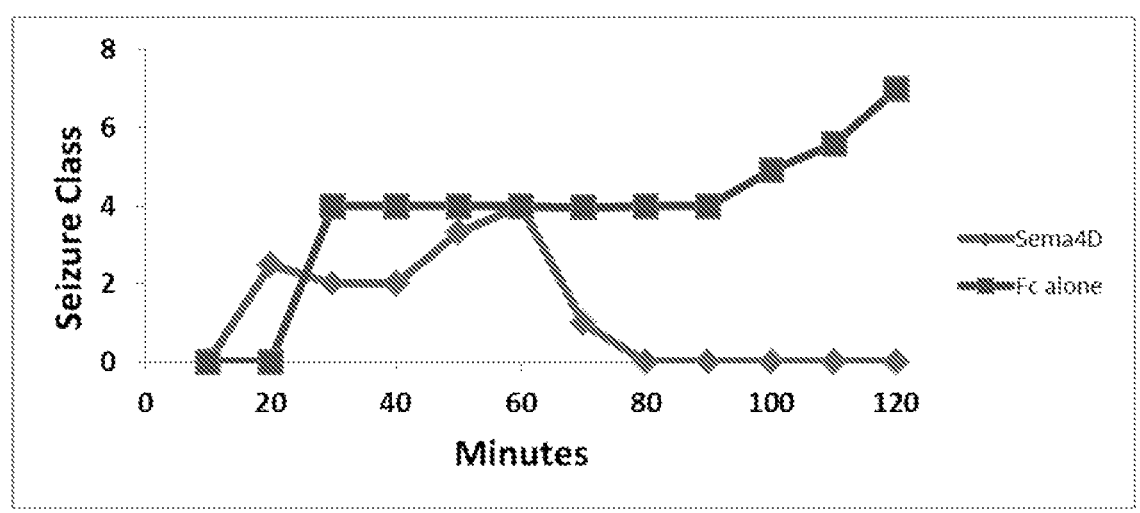
FIG. 8 shows the results of an in vivo seizure experiment with the effect of Sema4D treatment compared to control. Seizures were characterized using a Modified Racine Scale as follows: class I seizures were defined as mouth and facial movements; class II seizures were defined as repeated head bobbing; class III seizures were defined as forelimb clonus, class IV seizures included forelimb clonus and rearing onto hind legs, class V seizures included clonus, rearing, and loss of posture, class VI seizures included severe clonus and jumping, and class VII was recorded if the animal died.

Example 17—In Vivo Seizure Experiment with an Effect of Sema4D Treatment Compared to Control 8-Week old male mice were infused for three hours with either 100 nM Sema4D or Fc alone (vehicle control) directly into the hippocampus. After three hours of infusion, mice were injected intraperiotoneally (I.P) with 20 mg/kg Kainate and observed for two hours. Seizures were characterized using a Modified Racine Scale as follows: class I seizures were defined as mouth and facial movements; class II seizures were defined as repeated head bobbing; class III seizures were defined as forelimb clonus, class IV seizures included forelimb clonus and rearing onto hind legs, class V seizures included clonus, rearing, and loss of posture, class VI seizures included severe clonus and jumping, and class VII was recorded if the animal died. FIG. 8 shows the results of the in vivo seizure experiment with an effect of Sema4D treatment compared to control. As shown in FIG. 8, the seizure class was dramatically decreased after 60 minutes post injection with Kainate in mice infused with 100 nM Sema4D compared to control. It is believed that this effect is an indication that Sema4D treatment promotes GABAergic synapse formation in the hippocampus of these animals, thus putting a halt to the run away excitation that is a hallmark of epilepsy.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating a seizure disorder in a subject in need thereof, comprising administering to said subject a composition comprising an effective amount of an extracellular Sema4D polypeptide fragment, or a nucleic acid molecule encoding said extracellular Sema4D polypeptide fragment, wherein the extracellular Sema4D polypeptide fragment has at least 80% identity with amino acid residues 27-490 of SEQ ID NO: 6 and wherein said administering is effective to increase the number of GABAergic synapses between at least two hippocampal neurons that include one inhibitory neuron and one excitatory neuron, with one of said at least two neurons expressing plexinB1 receptor, thereby treating said seizure disorder in the subject.

2. The method of claim 1, wherein the extracellular Sema4D polypeptide fragment comprises amino acid residues 24-711 or 27-490 of the amino acid sequence of SEQ ID NO: 6 or a corresponding amino acid region in an ortholog thereof.

3. The method of claim 1, wherein the number of GABAergic synapses formed between at least two neurons of the subject increases without increasing the number of glutamatergic synapses between the two neurons.

4. The method of claim 1, wherein the inhibitory neuron is an interneuron.

5. The method of claim 1, further comprising contacting at least one of the neurons with a PlexinB1 polypeptide or a nucleic acid molecule encoding said PlexinB1 polypeptide.

6. The method of claim 1, wherein the composition is administered directly into the central nervous system of the subject.

7. The method of claim 1, wherein the seizure disorder is epilepsy.

8. The method of claim 1, wherein the subject is a human.

9. The method of claim 8, wherein the subject is an infant or child.

10. The method of claim 1, wherein said administering is repeated daily.

11. The method of claim 1, wherein the composition comprises 100 nM of the extracellular Sema4D polypeptide fragment.

12. The method of claim 1, wherein said administering is carried out using a dosage of at least 50 mg/day.

* * * * *

SEQUENCE LISTING

<160> NUMBER OF SEQ ID NOS: 14

<210> SEQ ID NO 1
<211> LENGTH: 2589
<212> TYPE: DNA
<213> ORGANISM: Homo sapiens

<400> SEQUENCE: 1

```
atgaggatgt gcacccccat taggggggctg ctcatggccc ttgcagtgat gtttgggaca        60
gcgatggcat ttgcacccat accccggatc acctgggagc acagagaggt gcacctggtg       120
cagtttcatg agccagacat ctacaactac tcagccttgc tgctgagcga ggacaaggac       180
accttgtaca taggtgcccg ggaggcggtc ttcgctgtga acgcactcaa catctccgag       240
aagcagcatg aggtgtattg gaaggtctca gaagacaaaa aagcaaaatg tgcagaaaag       300
gggaaatcaa aacagacaga gtgcctcaac tacatccggg tgctgcagcc actcagcgcc       360
acttcccttt acgtgtgtgg gaccaacgca ttccagccgg cctgtgacca cctgaactta       420 acatcccttta agtttctggg gaaaaatgaa gatggcaaag gaagatgtcc ctttgaccca       480
gcacacagct acacatccgt catggttgat ggagaacttt attcggggac gtcgtataat       540
tttttgggaa gtgaacccat catctcccga aattcttccc acagtcctct gaggacagaa       600
tatgcaatcc cttggctgaa cgagcctagt ttcgtgtttg ctgacgtgat ccgaaaaagc       660
ccagacagcc ccgacggcga ggatgacagg gtctacttct tcttcacgga ggtgtctgtg       720
gagtatgagt ttgtgttcag ggtgctgatc ccacggatag caagagtgtg caaggggggac       780 cagggcggcc tgaggacctt gcagaagaaa tggacctcct tcctgaaagc ccgactcatc       840
tgctcccggc cagacagcgg cttggtcttc aatgtgctgc gggatgtctt cgtgctcagg       900
tccccgggcc tgaaggtgcc tgtgttctat gcactcttca ccccacagct gaacaacgtg       960
gggctgtcgg cagtgtgcgc ctacaacctg tccacagccg aggaggtctt ctcccacggg      1020
aagtacatgc agagcaccac agtggagcag tcccacacca gtgggtgcg ctataatggc      1080 ccggtaccca gccgcggcc tggagcgtgc atcgacagcg aggcacgggc cgccaactac      1140
accagctcct tgaatttgcc agacaagacg ctgcagttcg ttaaagacca ccctttgatg      1200
gatgactcgg taacccaat agacaacagg cccaggttaa tcaagaaaga tgtgaactac      1260
acccagatcg tggtggaccg gacccaggcc ctggatggga ctgtctatga tgtcatgttt      1320
```

```
gtcagcacag accgggagc tctgcacaaa gccatcagcc tcgagcacgc tgttcacatc    1380
atcgaggaga cccagctctt ccaggacttt gagccagtcc agaccctgct gctgtcttca    1440
aagaagggca acaggtttgt ctatgctggc tctaactcgg gcgtggtcca ggccccgctg    1500
gccttctgtg gaagcacgg cacctgcgag gactgtgtgc tggcgcggga ccctactgc     1560 gcctggagcc cgcccacagc gacctgcgtg gctctgcacc agaccgagag ccccagcagg    1620
ggtttgattc aggagatgag cggcgatgct tctgtgtgcc cggataaaag taaaggaagt    1680
taccggcagc attttttcaa gcacggtggc acagcggaac tgaaatgctc ccaaaaatcc    1740
aacctggccc gggtcttttg gaagttccag aatggcgtgt tgaaggccga gagccccaag    1800
tacggtctta tgggcagaaa aaacttgctc atcttcaact tgtcagaagg agacagtggg    1860
gtgtaccagt gcctgtcaga ggagagggtt aagaacaaaa cggtcttcca agtggtcgcc    1920
aagcacgtcc tggaagtgaa ggtggttcca aagcccgtag tgggccccac cttgtcagtt    1980
gttcagacag aagtagtag gattgccacc aaagtgttgg tggcatccac ccaagggtct    2040
tctcccccaa cccagccgt gcaggccacc tcctccgggg ccatcaccct tcctcccaag    2100
cctgcgccca ccggcacatc ctgcgaacca agatcgtca tcaacacggt ccccagctc     2160 cactcggaga aaaccatgta tcttaagtcc agcgacaacc gcctcctcat gtccctcttc    2220
ctcttcttct tgttctctt cctctgcctc ttttctaca actgctataa gggatacctg     2280
cccagacagt gcttgaaatt ccgctcggcc ctactaattg gaagaagaa gcccaagtca    2340 gatttctgtg accgtgagca gagcctgaag gagacgttag tagagccagg gagcttctcc    2400
cagcagaatg gggagcaccc caagccagcc ctggacaccg gctatgagac cgagcaagac    2460
accatcacca gcaaagtccc cacggatagg gaggactcac agaggatcga cgacctttct    2520
gccagggaca agccctttga cgtcaagtgt gagctgaagt tcgctgactc agacgcagat    2580
ggagactga                                                              2589

<210> SEQ ID NO 2
<211> LENGTH: 862
<212> TYPE: PRT
<213> ORGANISM: Homo sapiens

<400> SEQUENCE: 2

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125

Asn Ala Phe Gln Pro Ala Cys Asp His Leu Asn Leu Thr Ser Phe Lys
    130                 135                 140
```

```
Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
    210                 215                 220

Asp Gly Glu Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
                260                 265                 270

Ser Phe Leu Lys Ala Arg Leu Ile Cys Ser Arg Pro Asp Ser Gly Leu
            275                 280                 285

Val Phe Asn Val Leu Arg Asp Val Phe Val Leu Arg Ser Pro Gly Leu
        290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Val Glu Gln Ser His
                340                 345                 350

Thr Lys Trp Val Arg Tyr Asn Gly Pro Val Pro Lys Pro Arg Pro Gly
            355                 360                 365

Ala Cys Ile Asp Ser Glu Ala Arg Ala Ala Asn Tyr Thr Ser Ser Leu
        370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
                420                 425                 430

Gly Thr Val Tyr Asp Val Met Phe Val Ser Thr Asp Arg Gly Ala Leu
            435                 440                 445

His Lys Ala Ile Ser Leu Glu His Ala Val His Ile Ile Glu Glu Thr
450                 455                 460

Gln Leu Phe Gln Asp Phe Glu Pro Val Gln Thr Leu Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
                500                 505                 510

Val Leu Ala Arg Asp Pro Tyr Cys Ala Trp Ser Pro Pro Thr Ala Thr
            515                 520                 525

Cys Val Ala Leu His Gln Thr Glu Ser Pro Ser Arg Gly Leu Ile Gln
        530                 535                 540

Glu Met Ser Gly Asp Ala Ser Val Cys Pro Asp Lys Ser Lys Gly Ser
545                 550                 555                 560
```

Tyr Arg Gln His Phe Phe Lys His Gly Gly Thr Ala Glu Leu Lys Cys
                565                 570                 575

Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
        595                 600                 605

Leu Leu Ile Phe Asn Leu Ser Glu Gly Asp Ser Gly Val Tyr Gln Cys
    610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Ala Pro
                645                 650                 655

Thr Leu Ser Val Val Gln Thr Glu Gly Ser Arg Ile Ala Thr Lys Val
                660                 665                 670

Leu Val Ala Ser Thr Gln Gly Ser Ser Pro Pro Thr Pro Ala Val Gln
            675                 680                 685

Ala Thr Ser Ser Gly Ala Ile Thr Leu Pro Pro Lys Pro Ala Pro Thr
        690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Phe Phe Val Leu Phe Leu Cys Leu Phe Phe
                740                 745                 750

Tyr Asn Cys Tyr Lys Gly Tyr Leu Pro Arg Gln Cys Leu Lys Phe Arg
        755                 760                 765

Ser Ala Leu Leu Ile Gly Lys Lys Pro Lys Ser Asp Phe Cys Asp
770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
                805                 810                 815

Thr Glu Gln Asp Thr Ile Thr Ser Lys Val Pro Thr Asp Arg Glu Asp
            820                 825                 830

Ser Gln Arg Ile Asp Asp Leu Ser Ala Arg Asp Lys Pro Phe Asp Val
        835                 840                 845

Lys Cys Glu Leu Lys Phe Ala Asp Ser Asp Ala Asp Gly Asp
    850                 855                 860

<210> SEQ ID NO 3
<211> LENGTH: 2217
<212> TYPE: DNA
<213> ORGANISM: Homo sapiens

<400> SEQUENCE: 3

```
atgaggatgt gcaccccat taggggctg ctcatggccc ttgcagtgat gtttgggaca      60
gcgatggcat tgcacccat accccggatc acctgggagc acagagaggt gcacctggtg     120
cagtttcatg agccagacat ctacaactac tcagccttgc tgctgagcga ggacaaggac    180
accttgtaca taggtgcccg ggaggcggtc ttcgctgtga acgcactcaa catctccgag    240
aagcagcatg aggtgtattg gaaggtctca gaagacaaaa agcaaaatg tgcagaaaag    300 gggaaatcaa aacagacaga gtgcctcaac tacatccggg tgctgcagcc actcagcgcc    360
acttcccttt acgtgtgtgg gaccaacgca ttccagccgg cctgtgacca cctgaactta    420
```

```
acatccttta agtttctggg gaaaaatgaa gatggcaaag gaagatgtcc ctttgaccca    480
gcacacagct acacatccgt catggttgat ggagaacttt attcggggac gtcgtataat    540 ttttttgggaa gtgaacccat catctcccga aattcttccc acagtcctct gaggacagaa   600
tatgcaatcc cttggctgaa cgagcctagt ttcgtgtttg ctgacgtgat ccgaaaaagc    660
ccagacagcc ccgacggcga ggatgacagg gtctacttct tcttcacgga ggtgtctgtg    720
gagtatgagt ttgtgttcag ggtgctgatc ccacggatag caagagtgtg caaggggggac  780 cagggcggcc tgaggacctt gcagaagaaa tggacctcct tcctgaaagc ccgactcatc    840
tgctcccggc cagacagcgg cttggtcttc aatgtgctgc gggatgtctt cgtgctcagg    900
tccccgggcc tgaaggtgcc tgtgttctat gcactcttca ccccacagct gaacaacgtg    960
gggctgtcgg cagtgtgcgc ctacaacctg tccacagccg aggaggtctt ctcccacggg   1020
aagtacatgc agagcaccac agtggagcag tcccacacca gtgggtgcg ctataatggc    1080 ccggtaccca gccgcggcc tggagcgtgc atcgacagcg aggcacgggc cgccaactac    1140
accagctcct tgaatttgcc agacaagacg ctgcagttcg ttaaagacca cccttttgatg  1200 gatgactcgg taaccccaat agacaacagg cccaggttaa tcaagaaaga tgtgaactac   1260
acccagatcg tggtggaccg gacccaggcc ctggatggga ctgtctatga tgtcatgttt    1320
gtcagcacag accggggagc tctgcacaaa gccatcagcc tcgagcacgc tgttcacatc    1380
atcgaggaga cccagctctt ccaggacttt gagccagtcc agaccctgct gctgtcttca    1440
aagaagggca caggtttgt ctatgctggc tctaactcgg gcgtggtcca ggccccgctg     1500
gccttctgtg ggaagcacgg cacctgcgag gactgtgtgc tggcgcggga cccctactgc    1560
gcctggagcc cgcccacagc gacctgcgtg gctctgcacc agaccgagag ccccagcagg    1620
ggtttgattc aggagatgag cggcgatgct ctgtgtgcc cggcctcgtc tcctaagccc     1680
ctccctcctc ctggctcctc ttccctgtcc tgtctgggcc atgtggggga caggaggctt    1740
tcctctccct ggaccccctg gccagcctcg ggtgcgggc ccgacagcag ctcgagggtc     1800
tccttgctgc cgcccttcct gagtgaccag gcacagcacg tgcacgccct ggggaacttc    1860
tacctcttct gccaggccac aggtcctgca gacattcgct ttgtctggga agaatgggg    1920 cgagctctgg agacctgtgt ccctgtgcag acccatgcac tgcccgatgg cagggcccat   1980
gcactcagct ggctgcagga cgccatcagg gaaagcgctg agtatcgctg ctctgtcctc   2040
tcctcagcag ggaacaagac ttcgaaggtg caggttgctg tgatgagacc tgaagtgacc    2100
caccaggaga ggtggaccag agagctctct gcctggaggg ctgtggctgg ggagcacgac    2160
cggatgatgc agagctggag gaaggcgtgg gaaagctgta gcaaggacac cctgtag       2217
```

<210> SEQ ID NO 4
<211> LENGTH: 738
<212> TYPE: PRT
<213> ORGANISM: Homo sapiens

<400> SEQUENCE: 4

```
Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60
```

-continued

```
Gly Ala Arg Glu Ala Val Phe Ala Val Asn Ala Leu Asn Ile Ser Glu
 65                  70                  75                  80

Lys Gln His Glu Val Tyr Trp Lys Val Ser Glu Asp Lys Lys Ala Lys
                 85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125

Asn Ala Phe Gln Pro Ala Cys Asp His Leu Asn Leu Thr Ser Phe Lys
    130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
    210                 215                 220

Asp Gly Glu Asp Asp Arg Val Tyr Phe Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Arg Pro Asp Ser Gly Leu
        275                 280                 285

Val Phe Asn Val Leu Arg Asp Val Phe Val Leu Arg Ser Pro Gly Leu
    290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Val Glu Gln Ser His
        340                 345                 350

Thr Lys Trp Val Arg Tyr Asn Gly Pro Val Pro Lys Pro Arg Pro Gly
        355                 360                 365

Ala Cys Ile Asp Ser Glu Ala Arg Ala Ala Asn Tyr Thr Ser Ser Leu
    370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
            420                 425                 430

Gly Thr Val Tyr Asp Val Met Phe Val Ser Thr Asp Arg Gly Ala Leu
        435                 440                 445

His Lys Ala Ile Ser Leu Glu His Ala Val His Ile Ile Glu Glu Thr
    450                 455                 460

Gln Leu Phe Gln Asp Phe Glu Pro Val Gln Thr Leu Leu Leu Ser Ser
465                 470                 475                 480
```

```
Lys Lys Gly Asn Arg Phe Val Tyr Ala Gly Ser Asn Ser Gly Val Val
                485                 490                 495
Gln Ala Pro Leu Ala Phe Cys Gly Lys His Gly Thr Cys Glu Asp Cys
            500                 505                 510
Val Leu Ala Arg Asp Pro Tyr Cys Ala Trp Ser Pro Thr Ala Thr
        515                 520                 525
Cys Val Ala Leu His Gln Thr Glu Ser Pro Ser Arg Gly Leu Ile Gln
    530                 535                 540
Glu Met Ser Gly Asp Ala Ser Val Cys Pro Ala Ser Ser Pro Lys Pro
545                 550                 555                 560
Leu Pro Pro Pro Gly Ser Ser Leu Ser Cys Leu Gly His Val Gly
                565                 570                 575
Asp Arg Arg Leu Ser Ser Pro Trp Thr Pro Trp Pro Ala Ser Gly Ala
            580                 585                 590
Gly Pro Asp Ser Ser Arg Val Ser Leu Leu Pro Pro Phe Leu Ser
        595                 600                 605
Asp Gln Ala Gln His Val His Ala Leu Gly Asn Phe Tyr Leu Phe Cys
    610                 615                 620
Gln Ala Thr Gly Pro Ala Asp Ile Arg Phe Val Trp Glu Lys Asn Gly
625                 630                 635                 640
Arg Ala Leu Glu Thr Cys Val Pro Val Gln Thr His Ala Leu Pro Asp
                645                 650                 655
Gly Arg Ala His Ala Leu Ser Trp Leu Gln Asp Ala Ile Arg Glu Ser
            660                 665                 670
Ala Glu Tyr Arg Cys Ser Val Leu Ser Ser Ala Gly Asn Lys Thr Ser
        675                 680                 685
Lys Val Gln Val Ala Val Met Arg Pro Glu Val Thr His Gln Glu Arg
    690                 695                 700
Trp Thr Arg Glu Leu Ser Ala Trp Arg Ala Val Ala Gly Glu His Asp
705                 710                 715                 720
Arg Met Met Gln Ser Trp Arg Lys Ala Trp Glu Ser Cys Ser Lys Asp
                725                 730                 735
Thr Leu

<210> SEQ ID NO 5
<211> LENGTH: 2586
<212> TYPE: DNA
<213> ORGANISM: Mus musculus

<400> SEQUENCE: 5
atgaggatgt gtgcccccgt tagggggctg ttcttggccc tggtggtagt gttgagaacc        60
gcggtggcat ttgcacctgt gcctcggctc acctgggaac atggagaggt aggtctggtg       120
cagtttcaca agccaggcat ctttaactac tcggccttgc tgatgagtga ggacaaagac       180
actctgtatg taggcgcccg ggaagcagtc tttgcagtga atgcgctgaa catctctgag       240
aagcaacatg aggtatattg gaaggtctct gaagacaaaa atccaagtg tgcagagaag       300 gggaaatcaa agcagacgga atgcctaaac tacattcgag tactacagcc actaagcagc       360
acttccctct atgtgtgtgg gaccaatgcg ttccagccca cctgtgacca cctgaacttg       420
acatccttca gtttctggg gaaaagtgaa gatggcaaag gaagatgccc cttcgacccc       480
gcccacagct acatcagt catggttggg gcgagctct actctgggac gtcctataat       540
ttcttgggca gtgaaccat catctctcga aactcttccc acagtccctt gaggacggag       600
tatgccatcc gtggctgaa cgagcctagc ttcgtctttg ctgacgtgat ccagaaaagc       660
```

```
ccagatggtc cggagggtga agatgacaag gtctacttct ttttttacgga ggtatccgtg    720
gagtacgaat tcgtcttcaa gttgatgatc ccgcgagttg ccagggtgtg caagggcgac    780
cagggcggcc tgcggacttt gcaaaaaaag tggacctcct tcctaaaggc caggctgatc    840
tgctccaagc cagacagtgg cctggtcttc aacatacttc aggatgtgtt tgtgctgagg    900
gccccgggcc tcaaggagcc tgtgttctat gcggtcttca ccccacagct gaacaatgtg    960
ggtctgtcag cggtgtgcgc ctacacactg ccacggtgg aggcagtctt ctcccgtgga    1020
aagtacatgc agagtgccac agtggagcag tctcacacca agtgggtgcg ctacaatggc    1080
ccagtgccca ctccccgacc tggagcgtgt atcgacagtg aggcccgggc agccaactac    1140
accagctcct gaatctccc agacaaaaca ctgcagtttg taaaagacca ccctttgatg    1200
gatgactcag tgaccccgat agacaacaga cccaagctga tcaaaaaaga tgtaaactac    1260
acccagatag tggtagacag gacccaggcc ctggatggga cttttctacga cgtcatgttc    1320
atcagcacag accggggagc ctgcataaa gcagtcatcc tcacaaaaga ggtgcatgtc    1380
atcgaggaga cccaactctt ccgggactct gaaccggtcc taactctgct gctatcgtca    1440
aagaagggga ggaagtttgt ctatgcaggc tccaactctg gagtggtcca agcgcccctg    1500
gcattctgcg aaaagcacgg tagctgtgaa gactgtgtgt tagcacggga ccctactgt    1560
gcctggagcc cagccatcaa ggcctgtgtt accctgcacc aggaagaggc ctccagcagg    1620
ggctggattc aggacatgag cggtgacaca tcctcatgcc tggataagag taaagaaagt    1680
ttcaaccagc attttttcaa gcacggcggc acagcggaac tcaaatgttt ccaaaagtcc    1740
aacctagccc gggtggtatg gaagttccag aatggcgagt tgaaggccgc aagtcccaag    1800
tacggctttg tgggcaggaa gcacctgctc atcttcaacc tgtcggacgg agacagcggc    1860
gtgtaccagt gcctgtcaga ggaaagggtg aggaataaaa cggtctccca gctgctggcc    1920
aagcacgttc tggaagtgaa gatggtacct cggacccccc cctcacctac ctcagaggat    1980
gctcagacag aaggtagtaa gatcacatcc aaaatgccgg ttgcatctac ccaggggtcc    2040
tctcccccta ccccggctct gtgggcaacc tcccccagag ccgccaccct acctcccaag    2100
tcctcctccg gcacatcctg tgaaccaaag atggtcatca acacggtccc ccagctccac    2160
tcagagaaga cggtgtatct caagtccagt gacaaccgcc tgctcatgtc tctcctcctc    2220
ttcatctttg tcctcttcct ctgcctcttt tcctacaact gctacaaggg ctacctgccc    2280
ggacagtgct taaaattccg ctcagccctg ctgcttggaa agaaaacacc caagtcagac    2340
ttctctgacc tggagcagag tgtgaaggag acactggtcg agcctgggag cttctcccag    2400
cagaacggcg accaccccaa gccagccctg gatacgggct atgaaacgga gcaggacacc    2460
atcaccagca agtccccac ggatcgtgag gactcgcaac ggatcgatga actctctgcc    2520
cgggacaaac cgtttgatgt caagtgtgaa ctgaagtttg cagattcgga tgctgacggg    2580
gactga                                                              2586
```

<210> SEQ ID NO 6  
<211> LENGTH: 861  
<212> TYPE: PRT  
<213> ORGANISM: Mus musculus

<400> SEQUENCE: 6

```
Met Arg Met Cys Ala Pro Val Arg Gly Leu Phe Leu Ala Leu Val Val
1               5                   10                  15

Val Leu Arg Thr Ala Val Ala Phe Ala Pro Val Pro Arg Leu Thr Trp
            20                  25                  30
```

```
Glu His Gly Glu Val Gly Leu Val Gln Phe His Lys Pro Gly Ile Phe
             35                  40                  45
Asn Tyr Ser Ala Leu Leu Met Ser Glu Asp Lys Asp Thr Leu Tyr Val
 50                  55                  60
Gly Ala Arg Glu Ala Val Phe Ala Val Asn Ala Leu Asn Ile Ser Glu
 65                  70                  75                  80
Lys Gln His Glu Val Tyr Trp Lys Val Ser Glu Asp Lys Lys Ser Lys
                 85                  90                  95
Cys Ala Glu Lys Gly Lys Ser Lys Gln Thr Glu Cys Leu Asn Tyr Ile
                100                 105                 110
Arg Val Leu Gln Pro Leu Ser Ser Thr Ser Leu Tyr Val Cys Gly Thr
                115                 120                 125
Asn Ala Phe Gln Pro Thr Cys Asp His Leu Asn Leu Thr Ser Phe Lys
130                 135                 140
Phe Leu Gly Lys Ser Glu Asp Gly Lys Gly Arg Cys Pro Phe Asp Pro
145                 150                 155                 160
Ala His Ser Tyr Thr Ser Val Met Val Gly Gly Glu Leu Tyr Ser Gly
                165                 170                 175
Thr Ser Tyr Asn Phe Leu Gly Ser Glu Pro Ile Ile Ser Arg Asn Ser
                180                 185                 190
Ser His Ser Pro Leu Arg Thr Glu Tyr Ala Ile Pro Trp Leu Asn Glu
                195                 200                 205
Pro Ser Phe Val Phe Ala Asp Val Ile Gln Lys Ser Pro Asp Gly Pro
                210                 215                 220
Glu Gly Glu Asp Asp Lys Val Tyr Phe Phe Phe Thr Glu Val Ser Val
225                 230                 235                 240
Glu Tyr Glu Phe Val Phe Lys Leu Met Ile Pro Arg Val Ala Arg Val
                245                 250                 255
Cys Lys Gly Asp Gln Gly Gly Leu Arg Thr Leu Gln Lys Lys Trp Thr
                260                 265                 270
Ser Phe Leu Lys Ala Arg Leu Ile Cys Ser Lys Pro Asp Ser Gly Leu
                275                 280                 285
Val Phe Asn Ile Leu Gln Asp Val Phe Val Leu Arg Ala Pro Gly Leu
                290                 295                 300
Lys Glu Pro Val Phe Tyr Ala Val Phe Thr Pro Gln Leu Asn Asn Val
305                 310                 315                 320
Gly Leu Ser Ala Val Cys Ala Tyr Thr Leu Ala Thr Val Glu Ala Val
                325                 330                 335
Phe Ser Arg Gly Lys Tyr Met Gln Ser Ala Thr Val Glu Gln Ser His
                340                 345                 350
Thr Lys Trp Val Arg Tyr Asn Gly Pro Val Pro Thr Pro Arg Pro Gly
                355                 360                 365
Ala Cys Ile Asp Ser Glu Ala Arg Ala Ala Asn Tyr Thr Ser Ser Leu
                370                 375                 380
Asn Leu Pro Asp Lys Thr Leu Gln Phe Val Lys Asp His Pro Leu Met
385                 390                 395                 400
Asp Asp Ser Val Thr Pro Ile Asp Asn Arg Pro Lys Leu Ile Lys Lys
                405                 410                 415
Asp Val Asn Tyr Thr Gln Ile Val Val Asp Arg Thr Gln Ala Leu Asp
                420                 425                 430
Gly Thr Phe Tyr Asp Val Met Phe Ile Ser Thr Asp Arg Gly Ala Leu
                435                 440                 445
```

```
His Lys Ala Val Ile Leu Thr Lys Glu Val His Val Ile Glu Glu Thr
    450                 455                 460
Gln Leu Phe Arg Asp Ser Glu Pro Val Leu Thr Leu Leu Ser Ser
465                 470                 475                 480
Lys Lys Gly Arg Lys Phe Val Tyr Ala Gly Ser Asn Ser Gly Val Val
                485                 490                 495
Gln Ala Pro Leu Ala Phe Cys Glu Lys His Gly Ser Cys Glu Asp Cys
                500                 505                 510
Val Leu Ala Arg Asp Pro Tyr Cys Ala Trp Ser Pro Ala Ile Lys Ala
                515                 520                 525
Cys Val Thr Leu His Gln Glu Glu Ala Ser Ser Arg Gly Trp Ile Gln
530                 535                 540
Asp Met Ser Gly Asp Thr Ser Ser Cys Leu Asp Lys Ser Lys Glu Ser
545                 550                 555                 560
Phe Asn Gln His Phe Phe Lys His Gly Gly Thr Ala Glu Leu Lys Cys
                565                 570                 575
Phe Gln Lys Ser Asn Leu Ala Arg Val Val Trp Lys Phe Gln Asn Gly
                580                 585                 590
Glu Leu Lys Ala Ala Ser Pro Lys Tyr Gly Phe Val Gly Arg Lys His
            595                 600                 605
Leu Leu Ile Phe Asn Leu Ser Asp Gly Asp Ser Gly Val Tyr Gln Cys
            610                 615                 620
Leu Ser Glu Glu Arg Val Arg Asn Lys Thr Val Ser Gln Leu Leu Ala
625                 630                 635                 640
Lys His Val Leu Glu Val Lys Met Val Pro Arg Thr Pro Ser Pro
                645                 650                 655
Thr Ser Glu Asp Ala Gln Thr Glu Gly Ser Lys Ile Thr Ser Lys Met
                660                 665                 670
Pro Val Ala Ser Thr Gln Gly Ser Ser Pro Thr Pro Ala Leu Trp
                675                 680                 685
Ala Thr Ser Pro Arg Ala Ala Thr Leu Pro Pro Lys Ser Ser Ser Gly
            690                 695                 700
Thr Ser Cys Glu Pro Lys Met Val Ile Asn Thr Val Pro Gln Leu His
705                 710                 715                 720
Ser Glu Lys Thr Val Tyr Leu Lys Ser Ser Asp Asn Arg Leu Leu Met
                725                 730                 735
Ser Leu Leu Leu Phe Ile Phe Val Leu Phe Leu Cys Leu Phe Ser Tyr
                740                 745                 750
Asn Cys Tyr Lys Gly Tyr Leu Pro Gly Gln Cys Leu Lys Phe Arg Ser
            755                 760                 765
Ala Leu Leu Leu Gly Lys Lys Thr Pro Lys Ser Asp Phe Ser Asp Leu
            770                 775                 780
Glu Gln Ser Val Lys Glu Thr Leu Val Glu Pro Gly Ser Phe Ser Gln
785                 790                 795                 800
Gln Asn Gly Asp His Pro Lys Pro Ala Leu Asp Thr Gly Tyr Glu Thr
                805                 810                 815
Glu Gln Asp Thr Ile Thr Ser Lys Val Pro Thr Asp Arg Glu Asp Ser
            820                 825                 830
Gln Arg Ile Asp Glu Leu Ser Ala Arg Asp Lys Pro Phe Asp Val Lys
            835                 840                 845
Cys Glu Leu Lys Phe Ala Asp Ser Asp Ala Asp Gly Asp
850                 855                 860
```

```
<210> SEQ ID NO 7
<211> LENGTH: 2583
<212> TYPE: DNA
<213> ORGANISM: Rattus norvegicus

<400> SEQUENCE: 7
atgaagatgt gtgcccccgt caggggctg ttcttggccc tggtggctgt gtggaggacc      60
gcggtggcat tcgcccctgt gcctcggatc acctgggagc acggagaggt aggtctggtg     120
aaccttcacg agccaggcat ctttaactac tcttccttgc tgatgacaag ccacaaggat     180
cctcctgtct ctgcctcccc aattggggct gcagtgaacc ggctctgaca tgttcccccc     240
tcacaggtat actggaaggt ctctgaagac aaaaaatcca agtgcgcaga aaggggaaa     300 tcaaagcaga cggagtgcct taactacatc cgagtgctgc aaccgcttag cagcacttcc     360
ctctacgtgt gtgggaccaa tgcgttccag cccacctgtg accacctgaa cttgacctct     420
ttcaagtttc tggggaaaag cgaagatggc aaaggaagat gccccttcga ccccgcccat     480
agctacacat ccgtcatggt cggggggagag ctctactctg ggacttcata taatttcttg     540
ggcagcgaac ccatcatctc tcgaaactct tcccacagtc cctgaggac agagtacgcc      600 atcccttggc taaacgagcc tagcttcgtc tttgctgacg tgatccacaa gagcccagat     660
ggtacagagg ctgaggatga caaggtctac ttcttcttta cggaggtgtc cgtggagtac     720
gagttcgtct tcaagttgat gatcccgcga gttgccaggg tgtgcaaggg cgaccagggc     780
ggcctgcgga cttttgcaaaa aaagtggacc tccttcctaa aggccagact gatctgctcc     840
aggccagaca gtggcctggt cttcaacatt cttcaagatg tgtttgtgct gagggccccg     900
ggcctcaagg aacctgtgtt ctatgcggtc ttcacccac agctgaacaa cgtgggtctg     960
tcagcggtct gtgcctacac gctgtccacg gtggaggccg tcttctcccg aggaaagtac    1020
atgcagagtg ccacagtgga gcagtctcac accagtgggg tacgctacaa tggcccagtg    1080
cccactcccc ggcctggagc gtgtatcgac agtgaggccc gggcagccaa ctacaccagc    1140
tccttgaatc tcccagacaa aacgctgcag tttgtcaaag accacccttt gatggacgac    1200
tcggtgacgc caatagacaa caggccgaaa ctgatcaaaa agatgtcaa ctacacccag    1260 atagtggtag acaggaccca ggccctggat gggaccttct acgacgtcat gttcctcagc    1320
acagaccggg gcgctctgca taaagctgtc atccttgcaa aagaggtaca cgtggttgag    1380
gagacccaac tcttccagga cttcgaaccg gtcctgtctc tgctgctatc atcaaagaag    1440
gggaggaagt ttgtctatgc tggctccaac tcaggagtgg tccaagctcc cctggccttc    1500
tgcggaaagc acagtagctg tgaagactgt gtgctagcac gggaccccta ctgcgcctgg    1560
agcccagcca tcaaggcctg tgttaccttg caccaggcag agggctctag caggggctgg    1620
attcaggaca tgagtggcga cacgtcctcg tgcctggata gagtaaaga aagtttccat    1680 cagcatttt tcaagcacgg cggcacagca gaactcaagt gttttccaaaa gtccaacctg    1740 gcccgggtgg tgtggaagtt ccagaacggc gagttgaagg ctgtgagtcc caagtatggc    1800
tttgtgggca ggaagcacct gctcatcttt aacctgtcag acggagacag cggtgtgtac    1860
cagtgcctgt cagaggaaag ggtcaggaat aaaacggtct cccagctgct cgccaagcac    1920
atcctggaag tgaaaatggt agctcggatc cccccatcac ctacctcaca gactgctcag    1980
acagaaggta gtaggatcac atccaaaatg cctgtggcgt ctaccagggg gtcctctccc    2040 cctacccgg ctctgtgggc aacctccccc agggctgcca cctacctcc caagtcctcc    2100 tccaccggca cgtcctgtga accaaaaatg gtcatcaaca cggtcccaca gctccactcg    2160
```

```
gagaagacag tgtatctcaa gtccagtgac aaccgcctgc tcatgtctct cctcctcttc   2220
ctctttgtcc tcttcctctg cctcttttcc tacaactgct acaagggcta cctgcccgga   2280
cagtgcttaa agttccgctc agccctgctg ctcgcaaaga aaaaacccaa gtcagagttc   2340
tctgacctgg agcagagtgt gaaggagacg ctggtagaac ctgggagctt ctcgcagcag   2400
aacggcgacc agcccaagcc agccttggat accggctatg aaaccgagca ggacactatc   2460
accagcaagg tccccaccga tcgagaggac tcgcaacgta tcgacgagct ctccgccagg   2520
gacaaaccgt ttgatgtcaa gtgtgaactc aagtttgcag actcggatgc cgacggggac   2580
tga                                                                2583
```

<210> SEQ ID NO 8
<211> LENGTH: 860
<212> TYPE: PRT
<213> ORGANISM: Rattus norvegicus
<220> FEATURE:
<221> NAME/KEY: misc_feature
<222> LOCATION: (76)..(76)
<223> OTHER INFORMATION: Xaa can be any naturally occurring amino acid

<400> SEQUENCE: 8

```
Met Lys Met Cys Ala Pro Val Arg Gly Leu Phe Leu Ala Leu Val Ala
1               5                   10                  15

Val Trp Arg Thr Ala Val Ala Phe Ala Pro Val Pro Arg Ile Thr Trp
            20                  25                  30

Glu His Gly Glu Val Gly Leu Val Asn Leu His Glu Pro Gly Ile Phe
        35                  40                  45

Asn Tyr Ser Ser Leu Leu Met Thr Ser His Lys Asp Pro Pro Val Ser
    50                  55                  60

Ala Ser Pro Ile Gly Ala Ala Val Asn Arg Leu Xaa His Val Pro Pro
65                  70                  75                  80

Ser Gln Val Tyr Trp Lys Val Ser Glu Asp Lys Lys Ser Lys Cys Ala
                85                  90                  95

Glu Lys Gly Lys Ser Lys Gln Thr Glu Cys Leu Asn Tyr Ile Arg Val
            100                 105                 110

Leu Gln Pro Leu Ser Ser Thr Ser Leu Tyr Val Cys Gly Thr Asn Ala
        115                 120                 125

Phe Gln Pro Thr Cys Asp His Leu Asn Leu Thr Ser Phe Lys Phe Leu
    130                 135                 140

Gly Lys Ser Glu Asp Gly Lys Gly Arg Cys Pro Phe Asp Pro Ala His
145                 150                 155                 160

Ser Tyr Thr Ser Val Met Val Gly Gly Glu Leu Tyr Ser Gly Thr Ser
                165                 170                 175

Tyr Asn Phe Leu Gly Ser Glu Pro Ile Ile Ser Arg Asn Ser Ser His
            180                 185                 190

Ser Pro Leu Arg Thr Glu Tyr Ala Ile Pro Trp Leu Asn Glu Pro Ser
        195                 200                 205

Phe Val Phe Ala Asp Val Ile His Lys Ser Pro Asp Gly Thr Glu Ala
    210                 215                 220

Glu Asp Asp Lys Val Tyr Phe Phe Thr Glu Val Ser Val Glu Tyr
225                 230                 235                 240

Glu Phe Val Phe Lys Leu Met Ile Pro Arg Val Ala Arg Val Cys Lys
                245                 250                 255

Gly Asp Gln Gly Gly Leu Arg Thr Leu Gln Lys Lys Trp Thr Ser Phe
            260                 265                 270
```

```
Leu Lys Ala Arg Leu Ile Cys Ser Arg Pro Asp Ser Gly Leu Val Phe
        275                 280                 285

Asn Ile Leu Gln Asp Val Phe Val Leu Arg Ala Pro Gly Leu Lys Glu
        290                 295                 300

Pro Val Phe Tyr Ala Val Phe Thr Pro Gln Leu Asn Asn Val Gly Leu
305                 310                 315                 320

Ser Ala Val Cys Ala Tyr Thr Leu Ser Thr Val Glu Ala Val Phe Ser
                325                 330                 335

Arg Gly Lys Tyr Met Gln Ser Ala Thr Val Glu Gln Ser His Thr Lys
                340                 345                 350

Trp Val Arg Tyr Asn Gly Pro Val Pro Thr Pro Arg Pro Gly Ala Cys
        355                 360                 365

Ile Asp Ser Glu Ala Arg Ala Ala Asn Tyr Thr Ser Ser Leu Asn Leu
        370                 375                 380

Pro Asp Lys Thr Leu Gln Phe Val Lys Asp His Pro Leu Met Asp Asp
385                 390                 395                 400

Ser Val Thr Pro Ile Asp Asn Arg Pro Lys Leu Ile Lys Lys Asp Val
                405                 410                 415

Asn Tyr Thr Gln Ile Val Val Asp Arg Thr Gln Ala Leu Asp Gly Thr
                420                 425                 430

Phe Tyr Asp Val Met Phe Leu Ser Thr Asp Arg Gly Ala Leu His Lys
        435                 440                 445

Ala Val Ile Leu Ala Lys Glu Val His Val Val Glu Glu Thr Gln Leu
        450                 455                 460

Phe Gln Asp Phe Glu Pro Val Leu Ser Leu Leu Ser Ser Lys Lys
465                 470                 475                 480

Gly Arg Lys Phe Val Tyr Ala Gly Ser Asn Ser Gly Val Val Gln Ala
                485                 490                 495

Pro Leu Ala Phe Cys Gly Lys His Ser Ser Cys Glu Asp Cys Val Leu
                500                 505                 510

Ala Arg Asp Pro Tyr Cys Ala Trp Ser Pro Ala Ile Lys Ala Cys Val
        515                 520                 525

Thr Leu His Gln Ala Glu Gly Ser Ser Arg Gly Trp Ile Gln Asp Met
        530                 535                 540

Ser Gly Asp Thr Ser Ser Cys Leu Asp Lys Ser Lys Glu Ser Phe His
545                 550                 555                 560

Gln His Phe Phe Lys His Gly Gly Thr Ala Glu Leu Lys Cys Phe Gln
                565                 570                 575

Lys Ser Asn Leu Ala Arg Val Val Trp Lys Phe Gln Asn Gly Glu Leu
        580                 585                 590

Lys Ala Val Ser Pro Lys Tyr Gly Phe Val Gly Arg Lys His Leu Leu
        595                 600                 605

Ile Phe Asn Leu Ser Asp Gly Asp Ser Gly Val Tyr Gln Cys Leu Ser
        610                 615                 620

Glu Glu Arg Val Arg Asn Lys Thr Val Ser Gln Leu Leu Ala Lys His
625                 630                 635                 640

Ile Leu Glu Val Lys Met Val Ala Arg Ile Pro Pro Ser Pro Thr Ser
                645                 650                 655

Gln Thr Ala Gln Thr Glu Gly Ser Arg Ile Thr Ser Lys Met Pro Val
                660                 665                 670

Ala Ser Thr Gln Gly Ser Ser Pro Pro Thr Pro Ala Leu Trp Ala Thr
        675                 680                 685
```

| | | | | | | | | | | | |
|---|---|---|---|---|---|---|---|---|---|---|---|
|Ser|Pro|Arg|Ala|Ala|Thr|Leu|Pro|Pro|Lys|Ser|Ser Thr Gly Thr|
| |690| | | |695| | | |700| | |

Ser Cys Glu Pro Lys Met Val Ile Asn Thr Val Pro Gln Leu His Ser
705                 710                 715                 720

Glu Lys Thr Val Tyr Leu Lys Ser Ser Asp Asn Arg Leu Leu Met Ser
            725                 730                 735

Leu Leu Leu Phe Leu Phe Val Leu Phe Cys Leu Phe Ser Tyr Asn
        740                 745                 750

Cys Tyr Lys Gly Tyr Leu Pro Gly Gln Cys Leu Lys Phe Arg Ser Ala
            755                 760                 765

Leu Leu Leu Ala Lys Lys Pro Lys Ser Glu Phe Ser Asp Leu Glu
770                 775                 780

Gln Ser Val Lys Glu Thr Leu Val Glu Pro Gly Ser Phe Ser Gln Gln
785                 790                 795                 800

Asn Gly Asp Gln Pro Lys Pro Ala Leu Asp Thr Gly Tyr Glu Thr Glu
                805                 810                 815

Gln Asp Thr Ile Thr Ser Lys Val Pro Thr Arg Glu Asp Ser Gln
            820                 825                 830

Arg Ile Asp Glu Leu Ser Ala Arg Asp Lys Pro Phe Asp Val Lys Cys
            835                 840                 845

Glu Leu Lys Phe Ala Asp Ser Asp Ala Asp Gly Asp
850                 855                 860

<210> SEQ ID NO 9
<211> LENGTH: 2589
<212> TYPE: DNA
<213> ORGANISM: Pan troglodytes

<400> SEQUENCE: 9

```
atgaggatgt gcaccccat taggggctg ctcatggccc ttgcagtgat gtttgggaca      60
gcgatggcat ttgcacccat accccggatc acctgggagc acagagaggt gcgcctggtg    120
cagtttcatg agccagacat ctacaactac tcagccttgc tgctgagcga ggacaaggac    180
accttgtaca taggtgcccg ggaggcggtc ttcgctgtga acgcactcaa catctccgag    240
aagcagcatg aggtgtattg gaaggtctca gaagacaaaa aagcaaaatg tgcagaaaag    300
gggaaatcaa aacagacaga gtgcctcaac tacatccggg tgctgcagcc actcagcgcc    360 acttccctt acgtgtgtgg gaccaacgca ttccagccgg cctgtgacca cctgaactta    420
acatccttta gtttctggg gaaaaatgaa gatggcaaag gaagatgtcc ctttgaccca    480
gcacacagct acacatccgt catggttgat ggagaacttt attcggggac gtcgtataat    540 ttttgggaa gtgaacccat catctcccga aattcttccc acagtcctct gaggacagaa    600
tacgcaatcc cttggctgaa cgagcctagt ttcgtgtttg ctgatgtgat ccgaaaaagc    660
ccagacagcc ccgacggcga ggatgacagg gtctacttct tcttcacgga ggtgtctgtg    720
gagtatgagt ttgtgttcag ggtgctgatc ccacggatag caagagtatg caagggggac    780
cagggcggcc tgaggaccct gcagaagaaa tggacctcct tcctgaaagc ccgactcatc    840 tgctccggc cagacagcgg cttggtcttc aatgtgctgc gggatgtctt cgtgctcagg    900
tccccgggcc tgaaggtgcc tgtgttctat gcactcttca ccccacagct gaacaacgtg    960
gggctgtcgg cagtgtgcgc ctacaacctg tccacagccg aggaggtctt ctcccacggg   1020
aagtacatgc agagcaccac agtggagcag tcccacacca gtgggtgcg ctataatggc   1080 ccggtaccca agccgcggcc tggagcgtgc atcgacagcg aggcacgggc cgccaactac   1140
```

```
accagctcct tgaatttgcc agacaagacg ctgcagttcg ttaaagacca cccttttgatg    1200 gatgactcgg taaccccaat agacaacagg cccaggttaa tcaagaaaga tatgaactac    1260
acccagatcg tggtggaccg gacccaggcc ctggatggga ctgtctatga tgtcatgttt    1320
gtcagcacag accggggagc tctgcacaaa gccatcagcc tcgagcacgc tgttcacatc    1380
atcgaggaga cccagctctt ccaggacttt gagccagtcc agaccctgct gctgtcttca    1440
aagaagggca caggtttgt ctatgctggc tccaactcgg gcgtggtcca ggccccgctg     1500
gccttctgtg ggaagcacgg cacctgcgag gactgtgtgc tggcgcggga ccctactgc    1560 gcctggaacc cgcccacagc gacctgcgtg gctctgcacc agaccgagag ccccagcagg    1620
ggtttgattc aggagatgag cggcgatgct tctgtgtgcc cggataaaag taaggaagt    1680 taccggcagc attttttcaa gcacggtggc acagcggaac tgaaatgctc ccaaaaatcc    1740
aacctggccc gggtcttttg aagttccag aatggcgtgt tgaaggccga gagccccaag    1800
tacggtctta tgggcagaaa aaacttgctc atcttcaact tgtcagaagg agacagtggg    1860
gtgtaccagt gcctgtcaga ggagagggtt aagaacaaaa cggtcttcca agtggtcgcc    1920
aagcacgtcc tggaagtgaa ggtggttcca agcccgtag tggcccccac cttgtcagtt     1980
gttcagacag aaggtagtag gattgccacc aaagtgttgg tggcatccac ccaagggtct    2040
tctcccccaa ccccagccgt gcaggccacc tcctccgggg ccatcaccct tcctcccaag    2100
cctgcgccca ctggcacatc ctgcgaacca agatcgtca tcaacacggt cccccagctc     2160
cactcggaga aaaccatgta tcttaagtcc agcgacaacc gcctcctcat gtccctcttc    2220
ctcctcttct ttgttctctt cctctgcctc tttttctaca actgctataa gggatacctg    2280
cccagacagt gcttgaaatt ccgctcggcc ctactaattg ggaagaagaa gcccaagtca    2340
gatttctgtg accgtgagca gagcctgaag gagacgttag tagagccagg gagcttctcc    2400
cagcagaatg gggagcaccc caagccagcc ctggacaccg gctatgagac cgagcaagac    2460
accatcacca gcaaagtccc cacgcatagg gaggactcac agaggatcga cgacctttct    2520
gccagggaca agccctttga cgtcaagtgt gagctgaagt tcgctgactc agacgcagat    2580
ggagactga                                                             2589
```

<210> SEQ ID NO 10
<211> LENGTH: 862
<212> TYPE: PRT
<213> ORGANISM: Pan troglodytes

<400> SEQUENCE: 10

```
Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val Arg Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
            100                 105                 110
```

Arg Val Leu Gln Pro Leu Ser Ala Thr Ser Leu Tyr Val Cys Gly Thr
115                 120                 125

Asn Ala Phe Gln Pro Ala Cys Asp His Leu Asn Leu Thr Ser Phe Lys
130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
210                 215                 220

Asp Gly Glu Asp Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Arg Pro Asp Ser Gly Leu
    275                 280                 285

Val Phe Asn Val Leu Arg Asp Val Phe Val Leu Arg Ser Pro Gly Leu
    290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Val Glu Gln Ser His
            340                 345                 350

Thr Lys Trp Val Arg Tyr Asn Gly Pro Val Pro Lys Pro Arg Pro Gly
        355                 360                 365

Ala Cys Ile Asp Ser Glu Ala Arg Ala Ala Asn Tyr Thr Ser Ser Leu
370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Met Asn Tyr Thr Gln Ile Val Val Asp Arg Thr Gln Ala Leu Asp
            420                 425                 430

Gly Thr Val Tyr Asp Val Met Phe Val Ser Thr Asp Arg Gly Ala Leu
        435                 440                 445

His Lys Ala Ile Ser Leu Glu His Ala Val His Ile Ile Glu Glu Thr
    450                 455                 460

Gln Leu Phe Gln Asp Phe Glu Pro Val Gln Thr Leu Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
            500                 505                 510

Val Leu Ala Arg Asp Pro Tyr Cys Ala Trp Asn Pro Pro Thr Ala Thr
        515                 520                 525

```
Cys Val Ala Leu His Gln Thr Glu Ser Pro Ser Arg Gly Leu Ile Gln
    530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Thr Ala Glu Leu Lys Cys
                565                 570                 575

Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
        595                 600                 605

Leu Leu Ile Phe Asn Leu Ser Glu Gly Asp Ser Gly Val Tyr Gln Cys
    610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Val Ala Pro
                645                 650                 655

Thr Leu Ser Val Val Gln Thr Glu Gly Ser Arg Ile Ala Thr Lys Val
            660                 665                 670

Leu Val Ala Ser Thr Gln Gly Ser Ser Pro Pro Thr Pro Ala Val Gln
        675                 680                 685

Ala Thr Ser Ser Gly Ala Ile Thr Leu Pro Pro Lys Pro Ala Pro Thr
    690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Leu Phe Phe Val Leu Phe Leu Cys Leu Phe Phe
            740                 745                 750

Tyr Asn Cys Tyr Lys Gly Tyr Leu Pro Arg Gln Cys Leu Lys Phe Arg
        755                 760                 765

Ser Ala Leu Leu Ile Gly Lys Lys Pro Lys Ser Asp Phe Cys Asp
    770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
                805                 810                 815

Thr Glu Gln Asp Thr Ile Thr Ser Lys Val Pro Thr Ala Arg Glu Asp
            820                 825                 830

Ser Gln Arg Ile Asp Asp Leu Ser Ala Arg Asp Lys Pro Phe Asp Val
        835                 840                 845

Lys Cys Glu Leu Lys Phe Ala Asp Ser Asp Ala Asp Gly Asp
    850                 855                 860
```

<210> SEQ ID NO 11
<211> LENGTH: 6408
<212> TYPE: DNA
<213> ORGANISM: Homo sapiens

<400> SEQUENCE: 11

```
atgcctgctc tgggcccagc tcttctccag gctctctggg ccgggtgggt cctcacccte    60 cagccccttc caccaactgc attcactccc aatggcacgt atctgcagca cctggcaagg   120
gaccccacct caggcaccct ctacctgggg gctaccaact tcctgttcca gctgagccct   180
gggctgcagc tggaggccac agtgtccacc ggccctgtgc tagacagcag ggactgcctg   240
```

-continued

| | |
|---|---|
| ccacctgtga tgcctgatga gtgccccag gcccagccta ccaacaaccc gaatcagctg | 300 |
| ctcctggtga gcccagggc cctggtggta tgcgggagcg tgcaccaggg ggtctgtgaa | 360 |
| cagcggcgcc tggggcagct cgagcagctg ctgctgcggc cagagcggcc tggggacaca | 420 |
| caatatgtgg ctgccaatga tcctgcggtc agcacggtgg ggctggtagc ccagggcttg | 480 |
| gcagggagc ccctcctgtt tgtggggcga ggatacacca gcagggtgt gggggtggc | 540 |
| attccaccca tcacaacccg ggccctgtgg ccgcccgacc cccaagctgc cttctcctat | 600 |
| gaggagacag ccaagctggc agtgggccgc ctctccgagt acagccacca cttcgtgagt | 660 |
| gcctttgcac gtggggccag cgcctacttc ctgttcctgc ggcgggacct gcaggctcag | 720 |
| tctagagctt ttcgtgccta tgtatctcga gtgtgtctcc gggaccagca ctactactcc | 780 |
| tatgtggagt tgcctctggc ctgcgaaggt ggccgctacg ggctgatcca ggctgcagct | 840 |
| gtggccacgt ccagggaggt ggcgcatggg gaggtgctct ttgcagcttt ctcctcggct | 900 |
| gcaccccca ctgtgggccg gccccatcg gcggctgctg gggcatctgg agcctctgcc | 960 |
| ctctgtgcct tcccctgga tgaggtggac cggcttgcta atcgcacgcg agatgcctgc | 1020 |
| tacacccggg aggtcgtgc tgaggatggg accgaggtgg cctacatcga gtatgatgtc | 1080 |
| aattctgact gtgcacagct gccagtgac accctggatg cttatccctg tggctcagac | 1140 |
| cacacgccca gccccatggc cagccgggtc ccgctggaag ccacaccaat tctggagtgg | 1200 |
| ccagggattc agctaacagc tgtggcagtc accatgaag atggacacac catcgctttc | 1260 |
| ctgggtgata gtcaagggca gctgcacagg gtctacttgg gcccagggag cgatggccac | 1320 |
| ccatactcca cacagagcat ccagcagggg tctgcagtga gcagagacct cacctttgat | 1380 |
| gggaccttg agcacctgta tgtcatgacc cagagcacac ttctgaaggt tcctgtggct | 1440 |
| tcctgtgctc agcacctgga ctgtgcatct tgccttgctc acaggaccc atactgtggg | 1500 |
| tggtgcgtgc tccttggcag gtgcagtcgc cgttctgagt gctcgagggg ccagggccca | 1560 |
| gagcagtggc tatggagctt ccagcctgag ctgggctgtc tgcaagtggc agccatgagt | 1620 |
| cctgccaaca tcagccgaga ggagacgagg gaggttttcc tatcagtgcc agacctgcca | 1680 |
| cccctgtggc caggggagtc atattcctgc cactttgggg aacatcagag tcctgccctg | 1740 |
| ctgactggtt ctggtgtgat gtgcccctcc ccagaccta gtgaggcccc agtgctgccg | 1800 |
| agaggagccg actacgtatc cgtgagcgtg gagctcagat ttggcgctgt tgtgatcgcc | 1860 |
| aaaacttccc tctctttcta tgactgtgtg gcggtcactg aactccgccc atctgcgcag | 1920 |
| tgccaggcct gtgtgagcag ccgctggggg tgtaactggt gtgtctggca gcacctgtgc | 1980 |
| acccacaagg cctcgtgtga tgctgggccc atggttgcaa gccatcagag cccgcttgtc | 2040 |
| tccccagacc ctcctgcaag aggtggaccc agccctccc cacccacagc ccccaaagcc | 2100 |
| ctggccaccc ctgctcctga caccttccc gtggagcctg gggctccctc cacagccaca | 2160 |
| gcttcggaca tctcacctgg ggctagtcct tccctgctca gccctggg gccatgggca | 2220 |
| ggttctggct ccatatcttc ccctggctcc acagggtcgc ctctccatga ggagccctcc | 2280 |
| cctcccagcc cccaaaatgg acctggaacc gctgtccctg ccccactga cttcagaccc | 2340 |
| tcagccacac ctgaggacct cttggcctcc ccgctgtcac cgtcagaggt agcagcagtg | 2400 |
| ccccctgcag accctggccc cgaggctctt catcccacag tgccctgga cctgccccct | 2460 |
| gccactgttc ctgccaccac tttcccaggg gccatgggct ccgtgaagcc cgccctggac | 2520 |
| tggctcacga gagaaggcgg cgagctgccc gaggcggacg agtggacggg gggtgacgca | 2580 |
| cccgccttct ccacttccac cctcctctca ggtgatggag actcagcaga gcttgagggc | 2640 |

```
cctcccgccc ccctcatcct cccgtccagc ctcgactacc agtatgacac ccccgggctc    2700
tgggagctgg aagaggcgac cttgggggca agctcctgcc cctgtgtgga gagcgttcag    2760
ggctccacgt tgatgccggt ccatgtggag cgggaaatcc ggctgctagg caggaacctg    2820
caccttttcc aggatggccc aggagacaat gagtgtgtga tggagctgga gggcctcgag    2880
gtggtggttg aggcccgggt cgagtgtgag ccacctccag atacccagtg ccatgtcacc    2940
tgccagcagc accagctcag ctatgaggct ctgcagccgg agctccgtgt ggggctgttt    3000
ctgcgtcggg ccggccgtct gcgtgtggac agtgctgagg ggctgcatgt ggtactgtat    3060
gactgttccg tgggacatgg agactgcagc cgctgccaaa ctgccatgcc ccagtatggc    3120
tgtgtgtggt gtgaggggga gcgtccacgt tgtgtgaccc gggaggcctg tggtgaggct    3180
gaggctgtgg ccacccagtg cccagcgccc ctcatccact cggtggagcc actgactggg    3240
cctgtagacg gaggcacccg tgtcaccatc aggggctcca acctgggcca gcatgtgcag    3300
gatgtgctgg gcatggtcac ggtgctggga gtgccctgtg ctgtggatgc ccaggagtac    3360
gaggtctcca gcagcctcgt gtgcatcacc ggggccagtg ggaggaggt ggccggcgcc    3420 acagcggtgg aggtgccggg aagaggacgt ggtgtctcag aacacgactt tgcctaccag    3480
gatccgaagg tccattccat cttcccggcc cgcggcccca gagctggggg cacccgtctc    3540
accctgaatg gctccaagct cctgactggg cggctggagg acatccgagt ggtggttgga    3600
gaccagcctt gtcacttgct gccggagcag cagtcagaac aactgcggtg tgagaccagc    3660
ccacgcccca cgcctgccac gctccctgtg gctgtgtggt ttggggccac ggagcggagg    3720
cttcaacgcg gacagttcaa gtataccttg gaccccaaca tcacctctgc tggccccacc    3780
aagagcttcc tcagtggagg acgtgagata tgcgtccgtg gccagaatct ggacgtggta    3840
cagacgccaa gaatccgggt gaccgtggtc tcgagaatgc tgcagcccag ccaggggctt    3900
ggacggaggc gtcgcgtggt cccggagacg gcatgttccc ttggaccctc ctgcagtagc    3960
cagcaatttg aggagccgtg ccatgtcaac tcctcccagc tcatcacgtg ccgcacacct    4020
gccctcccag gctgcctga ggaccctgg gtccgggtgg aatttatcct tgacaacctg    4080
gtctttgact ttgcaacact gaaccccaca ccttttctcct atgaggccga ccccacccctg    4140 cagccactca accctgagga ccccaccatg ccattccggc acaagcctgg gagtgtgttc    4200
tccgtggagg gggagaacct ggaccttgca atgtccaagg aggaggtggt ggctatgata    4260
ggggatggcc cctgtgtggt gaagacgctg acgcggcacc acctgtactg cgagcccccc    4320
gtggagcagc ccctgccacg gcaccatgcc ctccagagag cacctgactc tttgcctgag    4380
ttcacggtgc agatggggaa cttgcgcttc tccctgggtc acgtgcagta tgacggcgag    4440
agccctgggg cttttcctgt ggcagcccag gtgggcttgg gggtgggcac ctctcttctg    4500
gctctgggtg tcatcatcat tgtcctcatg tacaggagga gagcaagca ggccctgagg    4560 gactataaga aggttcagat ccagctggag aatctggaga gcagtgtgcg ggaccgctgc    4620
aagaaggaat tcacagacct catgactgag atgaccgatc tcaccagtga cctcctgggc    4680
agcggcatcc ccttcctcga ctacaaggtg tatgcggaga ggatcttctt ccctgggcac    4740
cgcgagtcgc ccttgcaccg ggacctgggt gtgcctgaga gcagacggcc cactgtggag    4800
caagggctgg ggcagctctc taacctgctc aacagcaagc tcttcctcac caagttcatc    4860
cacacgctgg agagccagcg caccttttca gctcgggacc gtgcctacgt ggcatctctg    4920
ctcaccgtgg cactgcatgg gaagcttgag tatttcactg acatcctccg cactctgctc    4980
agtgacctgg ttgcccagta tgtggccaag aaccccaagc tgatgctgcg caggacagag    5040
```

-continued

```
actgtggtgg agaagctgct caccaactgg atgtccatct gtctgtatac cttcgtgagg    5100
gactccgtag gggagcctct gtacatgctc tttcgaggga ttaagcacca agtggataag    5160
gggccagtgg acagtgtgac aggcaaggcc aaatacacct tgaacgacaa ccgcctgctc    5220
agagaggatg tggagtaccg tcccctgacc ttgaatgcac tattggctgt ggggcctggg    5280
gcaggagagg cccagggcgt gcccgtgaag gtcctagact gtgacaccat ctcccaggca    5340
aaggagaaga tgctggacca gctttataaa ggagtgcctc tcacccagcg gccagaccct    5400 cgcaccttg atgttgagtg gcggtctggg gtggccgggc acctcattct ttctgacgag     5460
gatgtcactt ctgaggtcca gggtctgtgg aggcgcctga acacactgca gcattacaag    5520
gtcccagatg gagcaactgt ggccctcgtc ccctgcctca ccaagcatgt gctccgggaa    5580
aaccaggatt atgtccctgg agagcggacc ccaatgctgg aggatgtaga tgagggggc     5640 atccggccct ggcacctggt gaagccaagt gatgagccgg agccgcccag gcctcggagg    5700
ggcagccttc ggggcgggga gcgtgagcgc gccaaggcca tccctgagat ctacctgacc    5760
cgcctgctgt ccatgaaggg caccctgcag aagttcgtgg atgacctgtt ccaggtgatt    5820
ctcagcacca gccgccccgt gccgctcgct gtgaagtact tctttgacct gctggatgag    5880
caggcccagc agcatggcat ctccgaccag gacaccatcc acatctggaa gaccaacagc    5940
ttgcctctga ggttctggat caatataata aaaaacccgc agtttgtgtt cgacgtgcaa    6000
acatctgata acatggatgc ggtgctcctt gtcattgcac agaccttcat ggacgcctgc    6060
accctggccg accacaagct gggccgggac tccccgatca caaaacttct gtatgcacgg    6120
gacattcccc ggtacaagcg gatggtggaa aggtactatg cagacatcag acagactgtc    6180
ccagccagcg accaagagat gaactctgtc ctggctgaac tgtcctggaa ctactccgga    6240
gacctcgggg cgcgagtggc cctgcatgaa ctctacaagt acatcaacaa gtactatgac    6300
cagatcatca ctgccctgga ggaggatggc acggcccaga gatgcagct ggactatcgg      6360 ctccagcaga ttgcagctgc tgtggaaaac aaggtcacag atctatag                  6408
```

<210> SEQ ID NO 12
<211> LENGTH: 2135
<212> TYPE: PRT
<213> ORGANISM: Homo sapiens

<400> SEQUENCE: 12

```
Met Pro Ala Leu Gly Pro Ala Leu Leu Gln Ala Leu Trp Ala Gly Trp
1               5                   10                  15

Val Leu Thr Leu Gln Pro Leu Pro Pro Thr Ala Phe Thr Pro Asn Gly
                20                  25                  30

Thr Tyr Leu Gln His Leu Ala Arg Asp Pro Thr Ser Gly Thr Leu Tyr
            35                  40                  45

Leu Gly Ala Thr Asn Phe Leu Phe Gln Leu Ser Pro Gly Leu Gln Leu
        50                  55                  60

Glu Ala Thr Val Ser Thr Gly Pro Val Leu Asp Ser Arg Asp Cys Leu
65                  70                  75                  80

Pro Pro Val Met Pro Asp Glu Cys Pro Gln Ala Gln Pro Thr Asn Asn
                85                  90                  95

Pro Asn Gln Leu Leu Leu Val Ser Pro Gly Ala Leu Val Val Cys Gly
            100                 105                 110

Ser Val His Gln Gly Val Cys Glu Gln Arg Arg Leu Gly Gln Leu Glu
        115                 120                 125
```

```
Gln Leu Leu Leu Arg Pro Glu Arg Pro Gly Asp Thr Gln Tyr Val Ala
    130                 135                 140

Ala Asn Asp Pro Ala Val Ser Thr Val Gly Leu Val Ala Gln Gly Leu
145                 150                 155                 160

Ala Gly Glu Pro Leu Leu Phe Val Gly Arg Gly Tyr Thr Ser Arg Gly
                165                 170                 175

Val Gly Gly Gly Ile Pro Pro Ile Thr Thr Arg Ala Leu Trp Pro Pro
                180                 185                 190

Asp Pro Gln Ala Ala Phe Ser Tyr Glu Glu Thr Ala Lys Leu Ala Val
                195                 200                 205

Gly Arg Leu Ser Glu Tyr Ser His His Phe Val Ser Ala Phe Ala Arg
    210                 215                 220

Gly Ala Ser Ala Tyr Phe Leu Phe Leu Arg Arg Asp Leu Gln Ala Gln
225                 230                 235                 240

Ser Arg Ala Phe Arg Ala Tyr Val Ser Arg Val Cys Leu Arg Asp Gln
                245                 250                 255

His Tyr Tyr Ser Tyr Val Glu Leu Pro Leu Ala Cys Glu Gly Gly Arg
            260                 265                 270

Tyr Gly Leu Ile Gln Ala Ala Val Ala Thr Ser Arg Glu Val Ala
    275                 280                 285

His Gly Glu Val Leu Phe Ala Ala Phe Ser Ser Ala Ala Pro Pro Thr
    290                 295                 300

Val Gly Arg Pro Pro Ser Ala Ala Ala Gly Ala Ser Gly Ala Ser Ala
305                 310                 315                 320

Leu Cys Ala Phe Pro Leu Asp Glu Val Asp Arg Leu Ala Asn Arg Thr
                325                 330                 335

Arg Asp Ala Cys Tyr Thr Arg Glu Gly Arg Ala Glu Asp Gly Thr Glu
                340                 345                 350

Val Ala Tyr Ile Glu Tyr Asp Val Asn Ser Asp Cys Ala Gln Leu Pro
            355                 360                 365

Val Asp Thr Leu Asp Ala Tyr Pro Cys Gly Ser Asp His Thr Pro Ser
    370                 375                 380

Pro Met Ala Ser Arg Val Pro Leu Glu Ala Thr Pro Ile Leu Glu Trp
385                 390                 395                 400

Pro Gly Ile Gln Leu Thr Ala Val Ala Val Thr Met Glu Asp Gly His
                405                 410                 415

Thr Ile Ala Phe Leu Gly Asp Ser Gln Gly Leu His Arg Val Tyr
                420                 425                 430

Leu Gly Pro Gly Ser Asp Gly His Pro Tyr Ser Thr Gln Ser Ile Gln
            435                 440                 445

Gln Gly Ser Ala Val Ser Arg Asp Leu Thr Phe Asp Gly Thr Phe Glu
    450                 455                 460

His Leu Tyr Val Met Thr Gln Ser Thr Leu Leu Lys Val Pro Val Ala
465                 470                 475                 480

Ser Cys Ala Gln His Leu Asp Cys Ala Ser Cys Leu Ala His Arg Asp
                485                 490                 495

Pro Tyr Cys Gly Trp Cys Val Leu Leu Gly Arg Cys Ser Arg Arg Ser
            500                 505                 510

Glu Cys Ser Arg Gly Gln Gly Pro Glu Gln Trp Leu Trp Ser Phe Gln
    515                 520                 525

Pro Glu Leu Gly Cys Leu Gln Val Ala Ala Met Ser Pro Ala Asn Ile
530                 535                 540
```

```
Ser Arg Glu Glu Thr Arg Glu Val Phe Leu Ser Val Pro Asp Leu Pro
545                 550                 555                 560

Pro Leu Trp Pro Gly Glu Ser Tyr Ser Cys His Phe Gly Glu His Gln
            565                 570                 575

Ser Pro Ala Leu Leu Thr Gly Ser Gly Val Met Cys Pro Ser Pro Asp
        580                 585                 590

Pro Ser Glu Ala Pro Val Leu Pro Arg Gly Ala Asp Tyr Val Ser Val
    595                 600                 605

Ser Val Glu Leu Arg Phe Gly Ala Val Val Ile Ala Lys Thr Ser Leu
    610                 615                 620

Ser Phe Tyr Asp Cys Val Ala Val Thr Glu Leu Arg Pro Ser Ala Gln
625                 630                 635                 640

Cys Gln Ala Cys Val Ser Ser Arg Trp Gly Cys Asn Trp Cys Val Trp
                645                 650                 655

Gln His Leu Cys Thr His Lys Ala Ser Cys Asp Ala Gly Pro Met Val
                660                 665                 670

Ala Ser His Gln Ser Pro Leu Val Ser Asp Pro Pro Ala Arg Gly
            675                 680                 685

Gly Pro Ser Pro Ser Pro Thr Ala Pro Lys Ala Leu Ala Thr Pro
690                 695                 700

Ala Pro Asp Thr Leu Pro Val Glu Pro Gly Ala Pro Ser Thr Ala Thr
705                 710                 715                 720

Ala Ser Asp Ile Ser Pro Gly Ala Ser Pro Ser Leu Ser Pro Trp
                725                 730                 735

Gly Pro Trp Ala Gly Ser Gly Ser Ile Ser Ser Pro Gly Ser Thr Gly
            740                 745                 750

Ser Pro Leu His Glu Glu Pro Ser Pro Ser Pro Gln Asn Gly Pro
            755                 760                 765

Gly Thr Ala Val Pro Ala Pro Thr Asp Phe Arg Pro Ser Ala Thr Pro
    770                 775                 780

Glu Asp Leu Leu Ala Ser Pro Leu Ser Pro Ser Glu Val Ala Ala Val
785                 790                 795                 800

Pro Pro Ala Asp Pro Gly Pro Glu Ala Leu His Pro Thr Val Pro Leu
            805                 810                 815

Asp Leu Pro Pro Ala Thr Val Pro Ala Thr Thr Phe Pro Gly Ala Met
                820                 825                 830

Gly Ser Val Lys Pro Ala Leu Asp Trp Leu Thr Arg Glu Gly Gly Glu
            835                 840                 845

Leu Pro Glu Ala Asp Glu Trp Thr Gly Gly Asp Ala Pro Ala Phe Ser
850                 855                 860

Thr Ser Thr Leu Leu Ser Gly Asp Gly Asp Ser Ala Glu Leu Glu Gly
865                 870                 875                 880

Pro Pro Ala Pro Leu Ile Leu Pro Ser Ser Leu Asp Tyr Gln Tyr Asp
                885                 890                 895

Thr Pro Gly Leu Trp Glu Leu Glu Glu Ala Thr Leu Gly Ala Ser Ser
            900                 905                 910

Cys Pro Cys Val Glu Ser Val Gln Gly Ser Thr Leu Met Pro Val His
            915                 920                 925

Val Glu Arg Glu Ile Arg Leu Leu Gly Arg Asn Leu His Leu Phe Gln
    930                 935                 940

Asp Gly Pro Gly Asp Asn Glu Cys Val Met Glu Leu Glu Gly Leu Glu
945                 950                 955                 960
```

```
Val Val Val Glu Ala Arg Val Glu Cys Glu Pro Pro Asp Thr Gln
            965                 970                 975

Cys His Val Thr Cys Gln Gln His Gln Leu Ser Tyr Glu Ala Leu Gln
            980                 985                 990

Pro Glu Leu Arg Val Gly Leu Phe Leu Arg Arg Ala Gly Arg Leu Arg
        995                 1000                1005

Val Asp Ser Ala Glu Gly Leu His Val Val Leu Tyr Asp Cys Ser
    1010                1015                1020

Val Gly His Gly Asp Cys Ser Arg Cys Gln Thr Ala Met Pro Gln
    1025                1030                1035

Tyr Gly Cys Val Trp Cys Glu Gly Glu Arg Pro Arg Cys Val Thr
    1040                1045                1050

Arg Glu Ala Cys Gly Glu Ala Glu Ala Val Ala Thr Gln Cys Pro
    1055                1060                1065

Ala Pro Leu Ile His Ser Val Glu Pro Leu Thr Gly Pro Val Asp
    1070                1075                1080

Gly Gly Thr Arg Val Thr Ile Arg Gly Ser Asn Leu Gly Gln His
    1085                1090                1095

Val Gln Asp Val Leu Gly Met Val Thr Val Ala Gly Val Pro Cys
    1100                1105                1110

Ala Val Asp Ala Gln Glu Tyr Glu Val Ser Ser Ser Leu Val Cys
    1115                1120                1125

Ile Thr Gly Ala Ser Gly Glu Glu Val Ala Gly Ala Thr Ala Val
    1130                1135                1140

Glu Val Pro Gly Arg Gly Arg Gly Val Ser Glu His Asp Phe Ala
    1145                1150                1155

Tyr Gln Asp Pro Lys Val His Ser Ile Phe Pro Ala Arg Gly Pro
    1160                1165                1170

Arg Ala Gly Gly Thr Arg Leu Thr Leu Asn Gly Ser Lys Leu Leu
    1175                1180                1185

Thr Gly Arg Leu Glu Asp Ile Arg Val Val Val Gly Asp Gln Pro
    1190                1195                1200

Cys His Leu Leu Pro Glu Gln Gln Ser Glu Gln Leu Arg Cys Glu
    1205                1210                1215

Thr Ser Pro Arg Pro Thr Pro Ala Thr Leu Pro Val Ala Val Trp
    1220                1225                1230

Phe Gly Ala Thr Glu Arg Arg Leu Gln Arg Gly Gln Phe Lys Tyr
    1235                1240                1245

Thr Leu Asp Pro Asn Ile Thr Ser Ala Gly Pro Thr Lys Ser Phe
    1250                1255                1260

Leu Ser Gly Gly Arg Glu Ile Cys Val Arg Gly Gln Asn Leu Asp
    1265                1270                1275

Val Val Gln Thr Pro Arg Ile Arg Val Thr Val Ser Arg Met
    1280                1285                1290

Leu Gln Pro Ser Gln Gly Leu Gly Arg Arg Arg Val Val Pro
    1295                1300                1305

Glu Thr Ala Cys Ser Leu Gly Pro Ser Cys Ser Ser Gln Gln Phe
    1310                1315                1320

Glu Glu Pro Cys His Val Asn Ser Ser Gln Leu Ile Thr Cys Arg
    1325                1330                1335

Thr Pro Ala Leu Pro Gly Leu Pro Glu Asp Pro Trp Val Arg Val
    1340                1345                1350
```

```
Glu Phe Ile Leu Asp Asn Leu Val Phe Asp Phe Ala Thr Leu Asn
    1355                1360                1365

Pro Thr Pro Phe Ser Tyr Glu Ala Asp Pro Thr Leu Gln Pro Leu
1370                1375                1380

Asn Pro Glu Asp Pro Thr Met Pro Phe Arg His Lys Pro Gly Ser
    1385                1390                1395

Val Phe Ser Val Glu Gly Glu Asn Leu Asp Leu Ala Met Ser Lys
1400                1405                1410

Glu Glu Val Val Ala Met Ile Gly Asp Gly Pro Cys Val Val Lys
    1415                1420                1425

Thr Leu Thr Arg His His Leu Tyr Cys Glu Pro Val Glu Gln
1430                1435                1440

Pro Leu Pro Arg His His Ala Leu Arg Glu Ala Pro Asp Ser Leu
    1445                1450                1455

Pro Glu Phe Thr Val Gln Met Gly Asn Leu Arg Phe Ser Leu Gly
1460                1465                1470

His Val Gln Tyr Asp Gly Glu Ser Pro Gly Ala Phe Pro Val Ala
    1475                1480                1485

Ala Gln Val Gly Leu Gly Val Gly Thr Ser Leu Leu Ala Leu Gly
1490                1495                1500

Val Ile Ile Ile Val Leu Met Tyr Arg Arg Lys Ser Lys Gln Ala
    1505                1510                1515

Leu Arg Asp Tyr Lys Lys Val Gln Ile Gln Leu Glu Asn Leu Glu
1520                1525                1530

Ser Ser Val Arg Asp Arg Cys Lys Lys Glu Phe Thr Asp Leu Met
    1535                1540                1545

Thr Glu Met Thr Asp Leu Thr Ser Asp Leu Leu Gly Ser Gly Ile
1550                1555                1560

Pro Phe Leu Asp Tyr Lys Val Tyr Ala Glu Arg Ile Phe Phe Pro
    1565                1570                1575

Gly His Arg Glu Ser Pro Leu His Arg Asp Leu Gly Val Pro Glu
1580                1585                1590

Ser Arg Arg Pro Thr Val Glu Gln Gly Leu Gly Gln Leu Ser Asn
    1595                1600                1605

Leu Leu Asn Ser Lys Leu Phe Leu Thr Lys Phe Ile His Thr Leu
1610                1615                1620

Glu Ser Gln Arg Thr Phe Ser Ala Arg Asp Arg Ala Tyr Val Ala
    1625                1630                1635

Ser Leu Leu Thr Val Ala Leu His Gly Lys Leu Glu Tyr Phe Thr
1640                1645                1650

Asp Ile Leu Arg Thr Leu Leu Ser Asp Leu Val Ala Gln Tyr Val
    1655                1660                1665

Ala Lys Asn Pro Lys Leu Met Leu Arg Arg Thr Glu Thr Val Val
1670                1675                1680

Glu Lys Leu Leu Thr Asn Trp Met Ser Ile Cys Leu Tyr Thr Phe
    1685                1690                1695

Val Arg Asp Ser Val Gly Glu Pro Leu Tyr Met Leu Phe Arg Gly
1700                1705                1710

Ile Lys His Gln Val Asp Lys Gly Pro Val Asp Ser Val Thr Gly
    1715                1720                1725

Lys Ala Lys Tyr Thr Leu Asn Asp Asn Arg Leu Leu Arg Glu Asp
1730                1735                1740
```

Val Glu Tyr Arg Pro Leu Thr Leu Asn Ala Leu Leu Ala Val Gly
1745                1750                1755

Pro Gly Ala Gly Glu Ala Gln Gly Val Pro Val Lys Val Leu Asp
1760                1765                1770

Cys Asp Thr Ile Ser Gln Ala Lys Glu Lys Met Leu Asp Gln Leu
1775                1780                1785

Tyr Lys Gly Val Pro Leu Thr Gln Arg Pro Asp Pro Arg Thr Leu
1790                1795                1800

Asp Val Glu Trp Arg Ser Gly Val Ala Gly His Leu Ile Leu Ser
1805                1810                1815

Asp Glu Asp Val Thr Ser Glu Val Gln Gly Leu Trp Arg Arg Leu
1820                1825                1830

Asn Thr Leu Gln His Tyr Lys Val Pro Asp Gly Ala Thr Val Ala
1835                1840                1845

Leu Val Pro Cys Leu Thr Lys His Val Leu Arg Glu Asn Gln Asp
1850                1855                1860

Tyr Val Pro Gly Glu Arg Thr Pro Met Leu Glu Asp Val Asp Glu
1865                1870                1875

Gly Gly Ile Arg Pro Trp His Leu Val Lys Pro Ser Asp Glu Pro
1880                1885                1890

Glu Pro Pro Arg Pro Arg Arg Gly Ser Leu Arg Gly Gly Glu Arg
1895                1900                1905

Glu Arg Ala Lys Ala Ile Pro Glu Ile Tyr Leu Thr Arg Leu Leu
1910                1915                1920

Ser Met Lys Gly Thr Leu Gln Lys Phe Val Asp Asp Leu Phe Gln
1925                1930                1935

Val Ile Leu Ser Thr Ser Arg Pro Val Pro Leu Ala Val Lys Tyr
1940                1945                1950

Phe Phe Asp Leu Leu Asp Glu Gln Ala Gln Gln His Gly Ile Ser
1955                1960                1965

Asp Gln Asp Thr Ile His Ile Trp Lys Thr Asn Ser Leu Pro Leu
1970                1975                1980

Arg Phe Trp Ile Asn Ile Ile Lys Asn Pro Gln Phe Val Phe Asp
1985                1990                1995

Val Gln Thr Ser Asp Asn Met Asp Ala Val Leu Leu Val Ile Ala
2000                2005                2010

Gln Thr Phe Met Asp Ala Cys Thr Leu Ala Asp His Lys Leu Gly
2015                2020                2025

Arg Asp Ser Pro Ile Asn Lys Leu Leu Tyr Ala Arg Asp Ile Pro
2030                2035                2040

Arg Tyr Lys Arg Met Val Glu Arg Tyr Tyr Ala Asp Ile Arg Gln
2045                2050                2055

Thr Val Pro Ala Ser Asp Gln Glu Met Asn Ser Val Leu Ala Glu
2060                2065                2070

Leu Ser Trp Asn Tyr Ser Gly Asp Leu Gly Ala Arg Val Ala Leu
2075                2080                2085

His Glu Leu Tyr Lys Tyr Ile Asn Lys Tyr Tyr Asp Gln Ile Ile
2090                2095                2100

Thr Ala Leu Glu Glu Asp Gly Thr Ala Gln Lys Met Gln Leu Gly
2105                2110                2115

Tyr Arg Leu Gln Gln Ile Ala Ala Ala Val Glu Asn Lys Val Thr
    2120                2125                2130

Asp Leu
    2135

<210> SEQ ID NO 13
<211> LENGTH: 6360
<212> TYPE: DNA
<213> ORGANISM: Mus musculus

<400> SEQUENCE: 13

| | | | | | |
|---|---|---|---|---|---|
| atgtctgtcc | tcggcccagt | tcttctccag | gtgttctggg | ccgggtgtgt | cgtcaccctg | 60 |
| cggtcccctc | tgccagctgc | tttcactgcc | aatggcacac | atctacaaca | cttggcaagg | 120 |
| gaccccacca | caggtaccct | ctatgtaggg | gccaccaact | tcctgttcca | gttgagccct | 180 |
| gggctgcagc | tggaagccgt | ggtgtccacg | ggccctgtga | atgacagccg | ggattgcctg | 240 |
| ccacctgtga | tacctgatga | atgtccccaa | gcccagccta | ctaacaaccc | taaccagctg | 300 |
| ctcctggtga | gcccagaggc | tctggtggtg | tgtgggagcg | tacaccaggg | catctgtgag | 360 |
| ctacggagcc | tggacagat | caggcagctg | ctgctacggc | cagagcgacc | tggggacacc | 420 |
| cagtatgtgg | ctgcaaatga | ccctgcagtc | agtacagtgg | ggctggtggc | ccagggattg | 480 |
| gtaggggagc | ccctcctgtt | tgtggggcgg | gggtacacca | gcaggggtgt | aggtggtggg | 540 |
| attcctccca | ttacaacccg | agccctgcga | ccaccggacc | cccaagctgc | cttctcttat | 600 |
| gaagaaacag | ccaagttagc | agtgggccgc | ctgtccgagt | acagccacca | cttcgtgagt | 660 |
| gcctttgtac | gcggggccag | tgcatacttc | ctgttcttgc | ggcgagacct | gaaggcccct | 720 |
| tctagagctt | tccgtgccta | tgtgtctcga | gtgtgccttc | aggaccagca | ctactactct | 780 |
| tatgtggaat | gccccctggc | ctgccagggt | ggtcgttacg | gtcttatcca | ggctgcagct | 840 |
| gtagccacgt | ccaaggaggt | ggcccgtggg | gacgtactct | ttgcagcttt | ctcctcagtg | 900 |
| gctcctccca | ctgtggattg | gccccctgtca | gcatctactg | gggcatctgg | aacctctgtg | 960 |
| ctctgtgcct | tcccctgga | tgaggtagac | cagcttgcta | attacactcg | agatgcctgt | 1020 |
| tatactcggg | aaggccgtgc | tgagaacggg | accaaggttg | ctgacattgc | atacgatgtc | 1080 |
| ctttccgact | gtgcgcagct | accagtggac | accccggatg | ctttttccatg | tggctctgac | 1140 |
| cacacaccca | gtcccatggt | cagctgtgtc | cctttggaag | ccacgccaat | tctggagcta | 1200 |
| ccaggggttc | agctaacagc | tgtggctgtc | accatggagg | atggacacac | tattgctttc | 1260 |
| ctgggtgaca | gtcaaggaca | gttgcatagg | gtctacttag | gccctggaag | aagtgctgcc | 1320 |
| ccatattcta | aacagagcat | ccagccgggg | tctcctgtga | acagagatct | tacctttgat | 1380 |
| ggtacctttg | agcatctcta | tgtagcaact | cagactactc | ttgtgaaggt | tcctgtggct | 1440 |
| ccttgtgctc | agcatctgga | ctgtgactct | tgccttgctc | acagggaccc | ttattgcgga | 1500 |
| tggtgtgtgc | tcctgggcag | gtgtagtcgc | cggtcggagt | gctcaaggga | ccagggccca | 1560 |
| gagcagtggc | tgtggagctt | ccagccggaa | ctgggctgtc | ttcgagtggt | ggccgtgagc | 1620 |
| cctgccaata | tcagtcggga | agagaggagg | gaggtttttct | tgtcagtgcc | aggcctgcca | 1680 |
| tctctctggc | caggggagtc | atatttctgc | tactttggag | accaacagag | tcctgctcta | 1740 |
| ctgaccagtt | ctggtgtgat | gtgtccctcc | ccagacccca | gtgaggctcc | agtgctgcag | 1800 |
| agaggagccg | accatatctc | tgtgaacgtg | gagctcaggt | ttggtgccgt | ggtgatcgcc | 1860 |
| agcacctccc | tctccttcta | tgactgcgtg | gcagttactg | cgtcttcccc | atctgcaccg | 1920 |
| tgccgggcct | gtgtgagcag | ccgctggggc | tgtaactggt | gtgtgtggca | gcagctgtgc | 1980 |

```
acacacaagg cctcgtgtga cgctgggcct atggtggcaa gccaacagag cccactcctt    2040
cccctaatcc ctcctgcaag ggatgaactc accccttccc cacccacagt cccccaaacc    2100
acggtcactc ctaccccaa cagcttccca atagagccta gggctccctc cacagcctca     2160
gatgtcctac ctggggccaa gccttccgg ctcagcctct ggggcccatg gcaggtcct      2220
ggccccatac tttcccctac ttccacagag tcacctcttc atgagaagcc ccttcctcct    2280
gacccccta ccatacctgg aaccactgtc cctgccccca ctggcttggg accatcgacc     2340
acacctgagg acctcttggc ctcctaccca ttcccctcag atgcagctgc agtgtcccct    2400
gcagagcctg gccctgaggc tctgccttcc atggtggctc tggaccagcc ccctggcact    2460
gttccagaca ctactttccc aggggcccct ggctccatga agcccgttct ggattggctc    2520
accaaaggag gcggcgagct gcccgaggcg gatgagtgga tggggggtga cacgcccgcc    2580
ttctccactt ccacactcct ctcaggtgat ggagactcag cagagcacga gggccctcct    2640
gccccctca tcctcctgtc cagcctcgac taccagtacg acaccccgg gctctgggag      2700
ctgggagagg tgaatcagag ggtgagctcc tgcccctgtg tggagaccgt ccagggctcc    2760
ttgctgatac cggtccatgt ggaacgcgaa gtccagcttc gaggcaggaa cctgtggctt    2820
ttccaggatg gcccgaggag cagcgagtgt gtgctggagc tagggagtcg ggaggtggct    2880
gtggaggctc aggtggagtg tgcgccgcct ccagatgtct ggtgccacat caagtgccag    2940
cagcatcagt tcagctatga agctttgaag ccagaactgc aggtggggct gttcctgcgt    3000
tgggcaggcg gtctgcgcgt ggacagtgcc gatgggctgc atgtggtgtt gtatgactgc    3060
tctgtgggac atggggactg cagccgctgc caaactgcca tgcctcagta cgactgtgtg    3120
tggtgtgagg gggagcgtcc gcgttgtgtg gcccgggaag cctgtaatga agccgagact    3180
gtggccactc agtgccccgc acctctcatt cactcggtgg atccactgac tggacctata    3240
gatggaggca cccgtgtcac tatcaggggc tccaacctgg gccaacatgt gcaggatgtc    3300
ctggacatgt tcagagtggc cggagttccc tgcgctgtgg atgctgggga gtatgatgtc    3360
tctagtagtc ttgtgtgcat cactggagcc agcggggagg aggtgactgg cactgtggca    3420
gtggaggtgc ctggaagagg acacggtgtc tcagagttca gctttgccta tcaggatcca    3480
aaagtacact ccatcttccc agcccgtggc cctagagctg gaggtacccg ccttaccctg    3540
catggttcta agctcctgac tggacggcta gaggacatcc gtgtggtggt tggagaccag    3600
ccttgccacc tgctcctgga gcagcagtct gagcagctac actgtgagac cggcccatac    3660
cctgtgcctg ctgaacttcc agtgactgtc ttgtttgggg ccactgagcg gaggcttcag    3720
cacggccaat tcaagtatac atcagacccc aatgtcacct cagtgggccc ctccaagagc    3780
ttcttcagcg gaggacgtga gatatgggtc cgcggccagg atcttgatgt ggtacagagg    3840
ccaagaatcc gagtgaccgt ggtcccaaga cagcatggcc aggggcttgc acagaagcaa    3900
cacgtggtcc ctgagaaatt tgaggagccg tgtctcgtga actcctccca cctcctcatg    3960
tgccgcactc ccgctctccc tggcccaccc tgggactctg ggtccaggt ggagtttatc     4020
ctcgacaaca tggtctttga ctttgctgca ctgagcccca cacccttctc ctatgaggct    4080
gatcccaccc tgcgttccct gaaccccgag gatcccagca cgccgttccg gcacaagcca    4140
gggagtgtgt tctctgtgga gggggagaat ctggacctcg ccatgtctaa agaagaggtg    4200
gtggccatga taggggacgg gccctgcgtg gtaaagacac tgacccggaa ccacctgtac    4260
tgtgagcccc ctgtggagca gccctgcca catccccatg ccctccgaga ggctccagat    4320
gctttgcctg agttcacggt acagatgggc aacctgcgct tctccttggg tcatgtgcag    4380
```

```
tacgatggcg agagccccgt ggcttttcct gtggcagccc aagtgggctt gggagtgggc    4440
acgtctctcc tggctctggg tgtcatcatc attgtcctca tatacaggag aagagcaag     4500
caggccctga gggactataa aaagtgcag atccagctgg agaacctgga gagcagtgta    4560
cgggaccgct gtaagaagga gtttacagac ctcatgacgg agatgacgga tctcaccagt    4620
gacctccttg gcagcggtat ccccttcctt gactacaaag tgtatgctga gagggtcttc    4680
ttccctgggt accgggagtc ccccttgcac agggacctcg gtgtgcctga cagcaggcga    4740
cccaccgtgg aacagggcct ggggcagctc tccaacctgc taaacagcaa gctcttcctt    4800
accaagttca tccacacact ggagagtcag cgcaccttct ctgctcggga ccgtgcctac    4860
gtggcatctc tgctcactgt tgcacttcac gggaagcttg aatacttcac ggacatactg    4920
cggactctgc tcagtgacct ggtagctcag tatgttgcca agaaccccaa gctgatgctg    4980
cgcaggacag agaccgtggt agaaaagctg ctcaccaact ggatgtccat ctgcctctac    5040
acctttgtga gggactctgt gggagagcct ctgtatatgc tcttcagagg gattaagcat    5100
caagtggaca agggtcccgt ggacagtgtg actggcaaag ccaaatacac tctgaatgac    5160
aaccgcctgc tcagagagga tgtggagtac cgtcccttga ccttgaatgc tcttctggct    5220
gtggggcctg ggcaggaga agcccagtgt gtacctgtga aagtcctgga ctgtgacacc    5280
atctcccagg ccaaggagaa gatgctagac cagctttaca agggagtgcc tcttgcccag    5340
cggcccgact cttgcacctt ggatgttgaa tggcggtctg gagtggctgg gcaccttatc    5400
ctttctgatg aggacgtcac ttccgaactc cagggtctgt ggaggcgtct gaatacactg    5460
caacattaca aggtcccaga tggagcaacg gtggcccttg tcccctgcct caccaagcat    5520
attcttaggg aaaaccagga ttatgtccct ggggaacgga ccccaatgct ggaggatgta    5580
gatgaggggg gcatccggcc ctggcacctg gtaaagccga gtgatgaacc agagcctccc    5640
aggccgagga ggggcagcct tcggggtggg gagcgtgagc gagccaaggc tatccctgag    5700
atctacctga cacgcctgct atccatgaag ggcacactgc agaagtttgt ggatgacctg    5760
ttccaggtga ttctcagcac cagccgccct gtgcctctgg ctgtgaagta cttctttgac    5820
ttgctggatg aacaagctca gcagcatggc atctctgatc aggatactat ccacatctgg    5880
aagaccaaca gcctgccgct aaggttctgg atcaacatca tcaagaaccc acagtttgtg    5940
ttcgatgtgc agacttcgga taacatggat gctgtgctcc tggtcattgc acagaccttc    6000
atggatgctt gcaccctggc cgaccacaag ctgggccggg attctcccat caacaaactt    6060
ctgtatgctc gagatattcc ccgttacaaa cagatggtgg aaaggtacta tgcagacatc    6120
agacagactg tcccggccag tgaccaagag atgaactcag tcttggcgga gctgtcccgg    6180
aactgctctg ccgaccttgg ggcgcgagtg gctctgcatg aactctacaa gtatatcaac    6240
aagtactatg accagatcat cactgccctg aggaggatg gcactgccca aagatgcag     6300
ctgggctacc ggctccagca gatcgccgct gctgtggaaa acaaggtcac ggatctataa    6360
```

<210> SEQ ID NO 14
<211> LENGTH: 2119
<212> TYPE: PRT
<213> ORGANISM: Mus musculus

<400> SEQUENCE: 14

Met Ser Val Leu Gly Pro Val Leu Leu Gln Val Phe Trp Ala Gly Cys
1               5                   10                  15

Val Val Thr Leu Arg Ser Pro Leu Pro Ala Ala Phe Thr Ala Asn Gly
            20                  25                  30

-continued

```
Thr His Leu Gln His Leu Ala Arg Asp Pro Thr Thr Gly Thr Leu Tyr
         35                  40                  45
Val Gly Ala Thr Asn Phe Leu Phe Gln Leu Ser Pro Gly Leu Gln Leu
 50                  55                  60
Glu Ala Val Val Ser Thr Gly Pro Val Asn Asp Ser Arg Asp Cys Leu
 65                  70                  75                  80
Pro Pro Val Ile Pro Asp Glu Cys Pro Gln Ala Gln Pro Thr Asn Asn
                 85                  90                  95
Pro Asn Gln Leu Leu Val Ser Pro Glu Ala Leu Val Val Cys Gly
            100                 105                 110
Ser Val His Gln Gly Ile Cys Glu Leu Arg Ser Leu Gly Gln Ile Arg
            115                 120                 125
Gln Leu Leu Leu Arg Pro Glu Arg Pro Gly Asp Thr Gln Tyr Val Ala
    130                 135                 140
Ala Asn Asp Pro Ala Val Ser Thr Val Gly Leu Val Ala Gln Gly Leu
145                 150                 155                 160
Val Gly Glu Pro Leu Leu Phe Val Gly Arg Gly Tyr Thr Ser Arg Gly
                165                 170                 175
Val Gly Gly Gly Ile Pro Pro Ile Thr Thr Arg Ala Leu Arg Pro Pro
            180                 185                 190
Asp Pro Gln Ala Ala Phe Ser Tyr Glu Glu Thr Ala Lys Leu Ala Val
        195                 200                 205
Gly Arg Leu Ser Glu Tyr Ser His His Phe Val Ser Ala Phe Val Arg
    210                 215                 220
Gly Ala Ser Ala Tyr Phe Leu Phe Leu Arg Arg Asp Leu Lys Ala Pro
225                 230                 235                 240
Ser Arg Ala Phe Arg Ala Tyr Val Ser Arg Val Cys Leu Gln Asp Gln
                245                 250                 255
His Tyr Tyr Ser Tyr Val Glu Leu Pro Leu Ala Cys Gln Gly Gly Arg
            260                 265                 270
Tyr Gly Leu Ile Gln Ala Ala Val Ala Thr Ser Lys Glu Val Ala
    275                 280                 285
Arg Gly Asp Val Leu Phe Ala Ala Phe Ser Ser Val Ala Pro Pro Thr
    290                 295                 300
Val Asp Trp Pro Leu Ser Ala Ser Thr Gly Ala Ser Gly Thr Ser Val
305                 310                 315                 320
Leu Cys Ala Phe Pro Leu Asp Glu Val Asp Gln Leu Ala Asn Tyr Thr
                325                 330                 335
Arg Asp Ala Cys Tyr Thr Arg Glu Gly Arg Ala Glu Asn Gly Thr Lys
            340                 345                 350
Val Ala Asp Ile Ala Tyr Asp Val Leu Ser Asp Cys Ala Gln Leu Pro
            355                 360                 365
Val Asp Thr Pro Asp Ala Phe Pro Cys Gly Ser Asp His Thr Pro Ser
    370                 375                 380
Pro Met Val Ser Cys Val Pro Leu Glu Ala Thr Pro Ile Leu Glu Leu
385                 390                 395                 400
Pro Gly Val Gln Leu Thr Ala Val Ala Val Thr Met Glu Asp Gly His
                405                 410                 415
Thr Ile Ala Phe Leu Gly Asp Ser Gln Gly Gln Leu His Arg Val Tyr
            420                 425                 430
Leu Gly Pro Gly Arg Ser Ala Ala Pro Tyr Ser Lys Gln Ser Ile Gln
            435                 440                 445
```

-continued

```
Pro Gly Ser Pro Val Asn Arg Asp Leu Thr Phe Asp Gly Thr Phe Glu
    450                 455                 460
His Leu Tyr Val Ala Thr Gln Thr Thr Leu Val Lys Val Pro Val Ala
465                 470                 475                 480
Pro Cys Ala Gln His Leu Asp Cys Asp Ser Cys Leu Ala His Arg Asp
                485                 490                 495
Pro Tyr Cys Gly Trp Cys Val Leu Leu Gly Arg Cys Ser Arg Arg Ser
                500                 505                 510
Glu Cys Ser Arg Asp Gln Gly Pro Glu Gln Trp Leu Trp Ser Phe Gln
                515                 520                 525
Pro Glu Leu Gly Cys Leu Arg Val Val Ala Val Ser Pro Ala Asn Ile
530                 535                 540
Ser Arg Glu Glu Arg Arg Glu Val Phe Leu Ser Val Pro Gly Leu Pro
545                 550                 555                 560
Ser Leu Trp Pro Gly Glu Ser Tyr Phe Cys Tyr Phe Gly Asp Gln Gln
                565                 570                 575
Ser Pro Ala Leu Leu Thr Ser Ser Gly Val Met Cys Pro Ser Pro Asp
                580                 585                 590
Pro Ser Glu Ala Pro Val Leu Gln Arg Gly Ala Asp His Ile Ser Val
                595                 600                 605
Asn Val Glu Leu Arg Phe Gly Ala Val Val Ile Ala Ser Thr Ser Leu
610                 615                 620
Ser Phe Tyr Asp Cys Val Ala Val Thr Ala Ser Ser Pro Ser Ala Pro
625                 630                 635                 640
Cys Arg Ala Cys Val Ser Ser Arg Trp Gly Cys Asn Trp Cys Val Trp
                645                 650                 655
Gln Gln Leu Cys Thr His Lys Ala Ser Cys Asp Ala Gly Pro Met Val
                660                 665                 670
Ala Ser Gln Gln Ser Pro Leu Leu Pro Leu Ile Pro Pro Ala Arg Asp
                675                 680                 685
Glu Leu Thr Pro Phe Pro Pro Thr Val Pro Gln Thr Thr Val Thr Pro
690                 695                 700
Thr Pro Asn Ser Phe Pro Ile Glu Pro Arg Ala Pro Ser Thr Ala Ser
705                 710                 715                 720
Asp Val Leu Pro Gly Ala Lys Pro Ser Arg Leu Ser Leu Trp Gly Pro
                725                 730                 735
Trp Ala Gly Pro Gly Pro Ile Leu Ser Pro Thr Ser Thr Glu Ser Pro
                740                 745                 750
Leu His Glu Lys Pro Leu Pro Pro Asp Pro Thr Ile Pro Gly Thr
                755                 760                 765
Thr Val Pro Ala Pro Thr Gly Leu Gly Pro Ser Thr Thr Pro Glu Asp
                770                 775                 780
Leu Leu Ala Ser Tyr Pro Phe Pro Ser Asp Ala Ala Val Ser Pro
785                 790                 795                 800
Ala Glu Pro Gly Pro Glu Ala Leu Pro Ser Met Val Ala Leu Asp Gln
                805                 810                 815
Pro Pro Gly Thr Val Pro Asp Thr Thr Phe Gly Ala Pro Gly Ser
                820                 825                 830
Met Lys Pro Val Leu Asp Trp Leu Thr Lys Gly Gly Gly Glu Leu Pro
                835                 840                 845
Glu Ala Asp Glu Trp Met Gly Gly Asp Thr Pro Ala Phe Ser Thr Ser
850                 855                 860
```

```
Thr Leu Leu Ser Gly Asp Gly Asp Ser Ala Glu His Glu Gly Pro Pro
865                 870                 875                 880

Ala Pro Leu Ile Leu Leu Ser Ser Leu Asp Tyr Gln Tyr Asp Thr Pro
                885                 890                 895

Gly Leu Trp Glu Leu Gly Glu Val Asn Gln Arg Val Ser Ser Cys Pro
            900                 905                 910

Cys Val Glu Thr Val Gln Gly Ser Leu Leu Ile Pro Val His Val Glu
        915                 920                 925

Arg Glu Val Gln Leu Arg Gly Arg Asn Leu Trp Leu Phe Gln Asp Gly
    930                 935                 940

Pro Arg Ser Ser Glu Cys Val Leu Glu Leu Gly Ser Arg Glu Val Ala
945                 950                 955                 960

Val Glu Ala Gln Val Glu Cys Ala Pro Pro Asp Val Trp Cys His
                965                 970                 975

Ile Lys Cys Gln Gln His Gln Phe Ser Tyr Glu Ala Leu Lys Pro Glu
                980                 985                 990

Leu Gln Val Gly Leu Phe Leu Arg Trp Ala Gly Gly Leu Arg Val Asp
            995                 1000                1005

Ser Ala Asp Gly Leu His Val Val Leu Tyr Asp Cys Ser Val Gly
    1010                1015                1020

His Gly Asp Cys Ser Arg Cys Gln Thr Ala Met Pro Gln Tyr Asp
    1025                1030                1035

Cys Val Trp Cys Glu Gly Glu Arg Pro Arg Cys Val Ala Arg Glu
    1040                1045                1050

Ala Cys Asn Glu Ala Glu Thr Val Ala Thr Gln Cys Pro Ala Pro
    1055                1060                1065

Leu Ile His Ser Val Asp Pro Leu Thr Gly Pro Ile Asp Gly Gly
    1070                1075                1080

Thr Arg Val Thr Ile Arg Gly Ser Asn Leu Gly Gln His Val Gln
    1085                1090                1095

Asp Val Leu Asp Met Val Arg Val Ala Gly Val Pro Cys Ala Val
    1100                1105                1110

Asp Ala Gly Glu Tyr Asp Val Ser Ser Ser Leu Val Cys Ile Thr
    1115                1120                1125

Gly Ala Ser Gly Glu Glu Val Thr Gly Thr Val Ala Val Glu Val
    1130                1135                1140

Pro Gly Arg Gly His Gly Val Ser Glu Phe Ser Phe Ala Tyr Gln
    1145                1150                1155

Asp Pro Lys Val His Ser Ile Phe Pro Ala Arg Gly Pro Arg Ala
    1160                1165                1170

Gly Gly Thr Arg Leu Thr Leu His Gly Ser Lys Leu Leu Thr Gly
    1175                1180                1185

Arg Leu Glu Asp Ile Arg Val Val Val Gly Asp Gln Pro Cys His
    1190                1195                1200

Leu Leu Leu Glu Gln Gln Ser Glu Gln Leu His Cys Glu Thr Gly
    1205                1210                1215

Pro Tyr Pro Val Pro Ala Glu Leu Pro Val Thr Val Leu Phe Gly
    1220                1225                1230

Ala Thr Glu Arg Arg Leu Gln His Gly Gln Phe Lys Tyr Thr Ser
    1235                1240                1245

Asp Pro Asn Val Thr Ser Val Gly Pro Ser Lys Ser Phe Phe Ser
    1250                1255                1260
```

```
Gly Gly Arg Glu Ile Trp Val Arg Gly Gln Asp Leu Asp Val Val
1265                 1270                1275

Gln Arg Pro Arg Ile Arg Val Thr Val Pro Arg Gln His Gly
1280                 1285                1290

Gln Gly Leu Ala Gln Lys Gln His Val Val Pro Glu Lys Phe Glu
1295                 1300                1305

Glu Pro Cys Leu Val Asn Ser Ser His Leu Leu Met Cys Arg Thr
1310                 1315                1320

Pro Ala Leu Pro Gly Pro Trp Asp Ser Gly Val Gln Val Glu
1325                 1330                1335

Phe Ile Leu Asp Asn Met Val Phe Asp Phe Ala Ala Leu Ser Pro
1340                 1345                1350

Thr Pro Phe Ser Tyr Glu Ala Asp Pro Thr Leu Arg Ser Leu Asn
1355                 1360                1365

Pro Glu Asp Pro Ser Thr Pro Phe Arg His Lys Pro Gly Ser Val
1370                 1375                1380

Phe Ser Val Glu Gly Glu Asn Leu Asp Leu Ala Met Ser Lys Glu
1385                 1390                1395

Glu Val Val Ala Met Ile Gly Asp Gly Pro Cys Val Val Lys Thr
1400                 1405                1410

Leu Thr Arg Asn His Leu Tyr Cys Glu Pro Pro Val Glu Gln Pro
1415                 1420                1425

Leu Pro His Pro His Ala Leu Arg Glu Ala Pro Asp Ala Leu Pro
1430                 1435                1440

Glu Phe Thr Val Gln Met Gly Asn Leu Arg Phe Ser Leu Gly His
1445                 1450                1455

Val Gln Tyr Asp Gly Glu Ser Pro Val Ala Phe Pro Val Ala Ala
1460                 1465                1470

Gln Val Gly Leu Gly Val Gly Thr Ser Leu Leu Ala Leu Gly Val
1475                 1480                1485

Ile Ile Ile Val Leu Ile Tyr Arg Arg Lys Ser Lys Gln Ala Leu
1490                 1495                1500

Arg Asp Tyr Lys Lys Val Gln Ile Gln Leu Glu Asn Leu Glu Ser
1505                 1510                1515

Ser Val Arg Asp Arg Cys Lys Lys Glu Phe Thr Asp Leu Met Thr
1520                 1525                1530

Glu Met Thr Asp Leu Thr Ser Asp Leu Leu Gly Ser Gly Ile Pro
1535                 1540                1545

Phe Leu Asp Tyr Lys Val Tyr Ala Glu Arg Val Phe Phe Pro Gly
1550                 1555                1560

Tyr Arg Glu Ser Pro Leu His Arg Asp Leu Gly Val Pro Asp Ser
1565                 1570                1575

Arg Arg Pro Thr Val Glu Gln Gly Leu Gly Gln Leu Ser Asn Leu
1580                 1585                1590

Leu Asn Ser Lys Leu Phe Leu Thr Lys Phe Ile His Thr Leu Glu
1595                 1600                1605

Ser Gln Arg Thr Phe Ser Ala Arg Asp Arg Ala Tyr Val Ala Ser
1610                 1615                1620

Leu Leu Thr Val Ala Leu His Gly Lys Leu Glu Tyr Phe Thr Asp
1625                 1630                1635

Ile Leu Arg Thr Leu Leu Ser Asp Leu Val Ala Gln Tyr Val Ala
1640                 1645                1650
```

-continued

Lys Asn Pro Lys Leu Met Leu Arg Arg Thr Glu Thr Val Val Glu
1655                 1660                1665

Lys Leu Leu Thr Asn Trp Met Ser Ile Cys Leu Tyr Thr Phe Val
1670                 1675                1680

Arg Asp Ser Val Gly Glu Pro Leu Tyr Met Leu Phe Arg Gly Ile
1685                 1690                1695

Lys His Gln Val Asp Lys Gly Pro Val Asp Ser Val Thr Gly Lys
1700                 1705                1710

Ala Lys Tyr Thr Leu Asn Asp Asn Arg Leu Leu Arg Glu Asp Val
1715                 1720                1725

Glu Tyr Arg Pro Leu Thr Leu Asn Ala Leu Leu Ala Val Gly Pro
1730                 1735                1740

Gly Ala Gly Glu Ala Gln Cys Val Pro Val Lys Val Leu Asp Cys
1745                 1750                1755

Asp Thr Ile Ser Gln Ala Lys Glu Lys Met Leu Asp Gln Leu Tyr
1760                 1765                1770

Lys Gly Val Pro Leu Ala Gln Arg Pro Asp Ser Cys Thr Leu Asp
1775                 1780                1785

Val Glu Trp Arg Ser Gly Val Ala Gly His Leu Ile Leu Ser Asp
1790                 1795                1800

Glu Asp Val Thr Ser Glu Leu Gln Gly Leu Trp Arg Arg Leu Asn
1805                 1810                1815

Thr Leu Gln His Tyr Lys Val Pro Asp Gly Ala Thr Val Ala Leu
1820                 1825                1830

Val Pro Cys Leu Thr Lys His Ile Leu Arg Glu Asn Gln Asp Tyr
1835                 1840                1845

Val Pro Gly Glu Arg Thr Pro Met Leu Glu Asp Val Asp Glu Gly
1850                 1855                1860

Gly Ile Arg Pro Trp His Leu Val Lys Pro Ser Asp Glu Pro Glu
1865                 1870                1875

Pro Pro Arg Pro Arg Arg Gly Ser Leu Arg Gly Gly Glu Arg Glu
1880                 1885                1890

Arg Ala Lys Ala Ile Pro Glu Ile Tyr Leu Thr Arg Leu Leu Ser
1895                 1900                1905

Met Lys Gly Thr Leu Gln Lys Phe Val Asp Asp Leu Phe Gln Val
1910                 1915                1920

Ile Leu Ser Thr Ser Arg Pro Val Pro Leu Ala Val Lys Tyr Phe
1925                 1930                1935

Phe Asp Leu Leu Asp Glu Gln Ala Gln Gln His Gly Ile Ser Asp
1940                 1945                1950

Gln Asp Thr Ile His Ile Trp Lys Thr Asn Ser Leu Pro Leu Arg
1955                 1960                1965

Phe Trp Ile Asn Ile Ile Lys Asn Pro Gln Phe Val Phe Asp Val
1970                 1975                1980

Gln Thr Ser Asp Asn Met Asp Ala Val Leu Leu Val Ile Ala Gln
1985                 1990                1995

Thr Phe Met Asp Ala Cys Thr Leu Ala Asp His Lys Leu Gly Arg
2000                 2005                2010

Asp Ser Pro Ile Asn Lys Leu Leu Tyr Ala Arg Asp Ile Pro Arg
2015                 2020                2025

Tyr Lys Gln Met Val Glu Arg Tyr Tyr Ala Asp Ile Arg Gln Thr
2030                 2035                2040

-continued

| | | | | | | | | | | | | |
|---|---|---|---|---|---|---|---|---|---|---|---|---|
| Val | Pro 2045 | Ala | Ser | Asp | Gln 2050 | Glu | Met | Asn | Ser | Val 2055 | Leu | Ala | Glu | Leu |
| Ser | Arg 2060 | Asn | Cys | Ser | Ala 2065 | Asp | Leu | Gly | Ala | Arg 2070 | Val | Ala | Leu | His |
| Glu | Leu 2075 | Tyr | Lys | Tyr | Ile 2080 | Asn | Lys | Tyr | Tyr | Asp 2085 | Gln | Ile | Ile | Thr |
| Ala | Leu 2090 | Glu | Glu | Asp | Gly 2095 | Thr | Ala | Gln | Lys | Met 2100 | Gln | Leu | Gly | Tyr |
| Arg | Leu 2105 | Gln | Gln | Ile | Ala 2110 | Ala | Ala | Val | Glu | Asn 2115 | Lys | Val | Thr | Asp |
| Leu | | | | | | | | | | | | | | |